US006376492B1

(12) United States Patent
Lind et al.

(10) Patent No.: US 6,376,492 B1
(45) Date of Patent: Apr. 23, 2002

(54) COMPOUNDS AND METHODS FOR INHIBITION OF HIV AND RELATED VIRUSES

(75) Inventors: Peter Thomas Lind; Rolf Noréen, both of Huddinge (SE); John Michael Morin, Brownsburg, IN (US); Robert John Ternansky, Carlsbad, CA (US)

(73) Assignee: Medivir AB, Huddinge (SE)

( * ) Notice: Subject to any disclaimer, the term of this patent is extended or adjusted under 35 U.S.C. 154(b) by 0 days.

(21) Appl. No.: 09/567,857

(22) Filed: May 9, 2000

Related U.S. Application Data

(60) Continuation of application No. 09/114,935, filed on Jul. 14, 1998, now abandoned, which is a division of application No. 08/601,030, filed on May 3, 1996, now Pat. No. 5,849,769.

(51) Int. Cl.[7] .................... A61K 31/252; A61K 31/495; C07D 401/00; C07D 239/02; C07D 413/00
(52) U.S. Cl. ........................ 514/252; 514/255; 514/256; 544/238; 544/241; 544/297; 544/322; 544/333; 544/359; 544/392; 544/403
(58) Field of Search ................................. 514/252, 255, 514/256; 544/238, 241, 297, 322, 333, 359, 392, 403

(56) References Cited

U.S. PATENT DOCUMENTS

| | | |
|---|---|---|
| 5,308,866 A | 5/1994 | Lesieur et al. ............... 514/469 |
| 5,380,750 A | 1/1995 | Lesieur et al. ............... 514/443 |
| 5,385,944 A | 1/1995 | Lesieur et al. ............... 514/585 |
| 5,389,683 A | 2/1995 | Lesieur et al. ............... 514/595 |
| 5,420,158 A | 5/1995 | Yous et al. .................. 514/510 |

FOREIGN PATENT DOCUMENTS

| | | |
|---|---|---|
| DE | 123466 | 12/1976 |
| DE | 2833073 | 3/1979 |
| EP | 0527687 | 2/1993 |
| EP | 0530087 | 3/1993 |
| EP | 0562956 | 9/1993 |
| EP | 0591057 | 4/1994 |
| EP | 0662471 | 7/1995 |
| GB | 2003866 | 3/1979 |

OTHER PUBLICATIONS

Chemical Abstracts 116:235102, 1992.
Chemical Abstracts 113:23837, 1989.
Chemical Abstracts 109:106992, 1988.
Chemical Abstracts 108:94583, 1987.
Chemical Abstracts 100:29502, 1983.
Chemical Abstracts 98:143211, 1983.
Chemical Abstracts 95:203851, 1981.
Chemical Abstracts 93:234301, 1980.
Chemical Abstracts 92:70288, 1979.
Chemical Abstracts 91:82986, 1979.
Chemical Abstracts 91:50948, 1979.
Chemical Abstracts 88:37969, 1977.
Chemical Abstracts 87:177464, 1977.
Chemical Abstracts 87:17148, 1977.
Chemical Abstracts 82:72917, 1974.
Chemical Abstracts 79:126522, 1973.
Chemical Abstracts 78:119098, 1973.
H. Willitzer et al., Pharmazie 33, H. 1 (1978), pp. 30–38.
V.P. Arya et al. Synthesis of Adamantane Derivatives with Potential Antiviral Activity, Indian Journal of Chemistry, vol. 10, (Jul. 1992), pp. 686–689.

*Primary Examiner*—Richard L. Raymond
*Assistant Examiner*—Tamthom N. Truong
(74) *Attorney, Agent, or Firm*—Birch Stewart Kolasch & Birch, LLP.

(57) ABSTRACT

The present invention is directed to compounds, compositions and methods of inhibiting and treating HIV and related viruses, and methods for cocrystallizing reverse transcriptase in vitro, inhibition of the replication of HIV and related viruses thereof.

31 Claims, No Drawings

COMPOUNDS AND METHODS FOR INHIBITION OF HIV AND RELATED VIRUSES

This application is a continuation of application Ser. No. 09/114,935, filed on Jul. 14, 1998, abandoned which, is a divisional of application Ser. No. 08/601,030, filed on May 3, 1996. Now U.S. Pat. No. 5,849,769 application Ser. No. 08/601/030 is the national phase of PCT International Application No. PCT/US94/09406 filed on Aug. 24, 1994 under 35 U.S.C. §371. The entire contents of each of the above-identified applications are hereby incorporated by reference.

FIELD OF THE INVENTION

The present invention relates to compounds and pharmaceutically acceptable salts thereof and methods for treating infections by HIV and related viruses and/or the treatment of Acquired Immune Deficiency Syndrome (AIDS) Also disclosed are pharmaceutical compositions containing the compounds and the method of use of the present compounds alone or in combination with other agents, for the treatment and inhibition of ATDS and viral infection from HIV.

BACKGROUND OF THE INVENTION

A retrovirus designated Human Immunodeficiency Virus (HIV) is believed to be the causative agent of the complex disease termed Acquired Immune Deficiency Syndrome (AIDS) and is a member of the lentivirus family of retroviruses (M. A. Gonda, F. Wong-Staal N R. C. Gallo, "Sequence Homology and Morphological Similarity of HTLV III and Visna Virus, A Pathogenic Lentivirus", *Science*, 227, 173, (1985); and P. Sonigo and N. Alizon, et al., "Nucleotide Sequence of the Visna Lentivirus: Relationship to the AIDS Virus", *Cell*, 42, 369, (1985)). The HIV virus (also referred to as the AIDS virus) was previously known as or referred to as LAV, HTLV-III, or ARV, and is now designated by HIV-1. Other closely related variants of HIV-1 include HIV-2 and SIV (simian immunodeficiency virus), and mutants thereof. The complex disease AIDS includes progressive destruction of the immune system and degeneration of the central and peripheral nervous system. The HIV virus appears to preferentially attack helper T-cells (T-lymphocytes or OKT4-bearing T-cells) and also other human cells, e.g., certain cells within the brain. The helper T-cells are invaded by the virus and the T-cell becomes an HIV virus producer. The helper T-cells are quickly destroyed and their number in the human being is depleted to such an extent that the body's B-cells as well as other T-cells normally stimulated by helper T-cells no longer function normally or produce sufficient lymphokines and antibodies to destroy the invading virus or other invading microbes.

While the HIV virus does not necessarily cause death per se, it does cause the human's immune system to be so severely depressed that the human falls prey to various other diseases such as herpes, *Pneumocystis carinii*, toxoplasmosis, cytomegalovirus, Kaposi's sarcoma, and Epstein-Barr virus related lymphomas among others. These secondary infections are separately treated using other medications as is conventional. Early during infection, humans with HIV virus seem to live on with little or no symptoms, but have persistent infections. Later in the disease, humans suffer mild immune system depression with various symptoms such as weight loss, malaise, fever, and swollen lymph nodes. These syndromes have been called persistent generalized lymphadenopathy syndrome (PGL) and AIDS related complex (ARC) and develop into AIDS.

In all cases, those infected with the AIDS virus are believed to be persistently infective to others. Further, AIDS and AIDS related complex is after some time fatal.

A description of the mechanism by which the virus infects its host is given in an article by R. Yarchoan, and S. Broder, "Development of Antiretroviral Therapy for the Acquired Immunodeficiency Syndrome and Related Disorders", *New England Journal of Medicine*, 316, 557–564 (Feb. 26, 1987).

Considerable efforts are being directed toward the control of HIV by means of inhibition of the reverse transcriptase of HIV, required for replication of thee virus. (V. Merluzzi et al., "Inhibition of the HIV-1 Replication by a Nonnucleoside Reverse Transcriptase Inhibitor", *Science*, 25, 1411 (1990)). For example, a currently used therapeutic compound, AZT, is an inhibitor of the viral reverse transcriptase (U.S. Pat. No. 4,724,232). Unfortunately, many of the now used compounds suffer from toxicity problems, lack of bioavailability or are short lived in vivo, viral resistance, or combinations thereof. Therefore, new compounds are being investigated. For example, a PCT application published on Feb. 18, 1993, (WO 93/03022; International Application No. PCT/SE92/00533) discloses thiourea compounds which show promise in the treatment and inhibition of HIV and AIDS.

Certain compounds falling within the scope of the definition of the methods of the present invention have been published in roles other than for the treatment of HIV. These compounds are excluded by proviso from the compound claims. The Chemical Abstract registry numbers or sources for these compounds are as follows:

| a) | i) 87977-01-3; |
| | ii) 75808-56-9; |
| | iii) 78329-62, 112822-56-7, -49-8, 51-2, -48, 7, -48-6, -50-1 and -46-5; |
| | iv) 65094-08-8; |
| | v) 39960-40-2 and -10-6, 64442-48-2 and -47-3; |
| | vi) U.S. Pat. No. 3,705,903; |
| | vii) 85180-12-7; |
| | viii) 55474-82-3; |
| | ix) 49551-06-6, -08-8, -08-4, -81-7, -67-9, -65-7, -58-8, -31-7, -63-3 and -60-2, and 49552-03-6; |
| | x) U.S. Pat. No. 4,057,636; |
| b) | 100973-52-2, 92852-25-0; |
| c) | 141403-37-4 |

Therefore, it is an object of the invention to provide compounds and pharmaceutically acceptable salts thereof to inhibit and/or treat HIV and AIDS.

Another object of the present invention is to provide therapeutic formulations that are of value in the inhibition and/or treatment of infection by HIV and the treatment or inhibition of the acquired immune deficiency syndrome.

Another object is to provide methods for the inhibition and/or treatment of infection by HIV and the resulting acquired immune deficiency syndrome.

Other objects, features, and advantages will become apparent to those skilled in the art from the following description and claims.

DESCRIPTION OF THE INVENTION

The present invention provides compounds useful for the inhibition and/or treatment of HIV and AIDS, either as compounds, pharmaceutically acceptable salts, pharmaceutical composition Ingredients, whether or not in combination with other anti-virals, immunomodulators, antibiotics, or vaccines. Methods of treating or inhibiting AIDS, methods of inhibiting replication of HIV, and methods of treating or inhibiting HIV in humans are also disclosed.

The compounds used in the methods of the present invention are those of the formula (IA) below

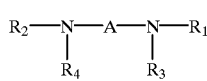

(1A)

wherein A is

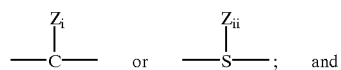; and wherein $R^a$ is H, $OR^b$, CN, $NO_2$, $N(R^b)_2$, $SR^b$, $SO_2R^b$, $SO_2N(R^b)_2$, $COR^b$, $CO_2R^b$, $CON(R^b)_2$, $PO(R^b)2$, $PO(OR^b)_2$, $PO(NR^b)_2$, wherein $R^b$ is hydrogen, $C_1-C_6$ alkyl, $C_1-C_6$ substituted alkyl, $C_2-C_6$ alkenyl, $C_2-C_6$ substituted alkenyl, $C_2-C_8$ alkynyl, $C_2-C_8$ substituted alkynyl, $C_1-C_6$ alkoxy, $C_1-C_6$ substituted alkoxy, $C_{4-10}$ aralkyl, $C_{1-10}$ alkaryl, $C_{1-10}$ alkylthio, $C_{4-10}$ aralkylthio, $C_{1-10}$ alkylsulfinyl, $C_{4-10}$ alkylsulfinyl, $C_{1-10}$ alkylsulfonyl, $C_{4-10}$ alkylsulfonyl, carboxy, $C_{1-10}$ alkylthiocarbonyl, $C_{4-10}$ aralkylcarbonyl, $C_{4-10}$ aralkylthiocarbonyl, $C_{4-10}$ aralkoxycarbonyl, $C_{4-10}$ aralkoxycarbonyl, $C_{1-4}$ alkyl, $C_{4-10}$ aralkoxy, $C_{1-12}$ dialkylamino-$C_{1-6}$ aralkanoylamino $C_{4-10}$ aralkylamino or $C_1-C_4$ alkanoyloxy;

$R_1$ is a stable saturated or unsaturated, substituted or unsubstituted, 3 to 8 membered organic monocyclic ring having 0 to 4 hetero atoms selected from S, O, and N; or $R_1$ is a stable, saturated or unsaturated, substituted or unsubstituted, 7 to 10 membered organic bicyclic ring having 0 to 5 hetero atoms selected from S, O, and N;

$R_2$ is a group of the formula

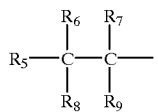

wherein $R_5$ is $R_1$ as defined above; or $R_5$ is a group of the formula $(R_{10})_y$—X— wherein y is 1 or 2; X is N, S, O and $R_{10}$ is $R_1$ as defined; or $R_{10}$ is hydrogen, $C_1-C_6$alkyl, $C_2-C_6$ alkenyl, or $C_2-C_6$ alkynyl, substituted $C_1-C_6$alkyl, substituted $C_2-C_6$ alkenyl, or substituted $C_2-C_6$ alkynyl; or $R_5$ is hydrogen, halo, cyano, carboxy, amino, thio, hydroxy, $C_1-C_6$ alkoxy, $C_1-C_6$ substituted alkoxy, $C_1-C_6$ alkyl, $C_2-C_8$ alkenyl, $C_2-C_8$ alkynyl, or $C_2-C_8$ alkenoxy;

$R_6$, $R_7$, $R_8$, and $R_9$ are independently $C_3-C_8$ cycloalkyl, hydrogen, $C_1-C_6$ alkyl, $C_2-C_6$ alkenyl, $C_2-C_6$ alkynyl, substituted $C_1-C_6$alkyl, substituted $C_2-C_6$ alkenyl, or substituted $C_2-C_6$ alkynyl, $C_1-C_6$ substituted alkoxy, halo, amino, nitro, cyano, $C_1-C_5$ alkoxy, hydroxy, carboxy, hydroxymethyl, aminomethyl, carboxymethyl, $C_1-C_4$ alkylthio, $C_1-C_4$ alkanoyloxy, carbamoyl, or a halo substituted $C_1-C_6$ alkyl; or two of which, along with the carbons to which they are attached, combine to form a stable, saturated or unsaturated, substituted or unsubstituted, 3 to 7 membered organic monocylic ring having 0 to 4 hetero atoms selected from S, O, or N; or $R_6$ and $R_8$, or $R_7$ and $R_9$, along with the carbon to which they are attached, form a stable, saturated or unsaturated, substituted or unsubstituted, 3 to 7 membered organic monocyclic ring having 0 to 4 hetero atoms selected from S, O, or N;

$R_3$ and $R_4$ are independently hydrogen, hydroxy, $C_1-C_6$ alkyl, $C_2-C_6$ alkenyl, $C_2-C_6$ alkynyl, substituted $C_1-C_6$alkyl, substituted $C_2-C_6$ alkenyl, or substituted $C_2-C_6$ alkynyl, substituted alkoxy, amino, cyano, nitro, $C_1-C_6$ alkoxy, $C_1-C_6$ substituted alkoxy, carboxy, hydroxymethyl, aminomethyl, carboxymethyl, $C_1-C_4$ alkylthio, $C_1-C_4$ alkanoyloxy, halo-substituted ($C_1-C_6$)alkyl, or carbamoyl; or salts thereof;

It should also be understood that when the term "HIV" is used, it includes HIV-1, components, mutant variations, subtypes, and serotypes thereof, and related viruses, components, mutant variations, subtypes, and serotypes thereof. When the term "inhibit" is used, its ordinary meaning is intended, which is to prohibit, hold in check, or discourage, and is not to be construed to be limited to a particular process, procedure, or mechanism of action.

The terms "stable, saturated or unsaturated, substituted or unsubstituted, 3 to 8 membered", or "3 to 7 membered organic monocyclic ring having 0 to 4 hetero atoms selected from S, O, and N" include those wherein the nitrogen and sulfur hetero atoms are optionally oxidized, and the nitrogen hetero atom optionally quaternized. The substituted ring may have 1–8 substituents independently selected from aryl, substituted aryl, halo, $C_1-C_6$ alkyl, $C_1-C_5$ alkoxy, $C_1-C_6$ alkenyl, $C_2-C_8$ alkynyl, $C_2-C_8$ alkenoxy, amino, nitro, cyano, carboxy, hydroxymethyl, aminomethyl, carboxymethyl, $C_1-C_4$ alkylthio, hydroxy, $C_1-C_4$ alkanoyloxy, carbamoyl, halo-substituted $C_1-C_6$ alkyl, $C_1-C_6$ alkoxy-substituted $C_1-C_6$ alkyl, a group of the formula

wherein $R_x$ is $C_1-C_6$ alkyl, aryl, substituted aryl, or amino; or a group of the formula

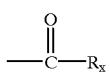

wherein $R_x$ is as defined above.

The term "stable, saturated or unsaturated, substituted or unsubstituted, 7 to 10 membered organic bicyclic rings having 0 to 5 hetero atoms selected from S, O, and N" includes those wherein the nitrogen and sulfur hetero atoms are optionally oxidized, and the nitrogen hetero atom(s) optionally quaternized. The bicyclic rings may be substituted 1 to 8 times, the substituents independently selected from those above listed for the monocyclic rings.

Examples of such monocyclic and bicyclic rings are cyclo($C_3-C_8$)alkyl, cyclo($C_3-C_8$)alkenyl; isothiazolyl, substituted isothiazolyl, tetrazolyl, substituted tetrazolyl, triazolyl, substituted triazolyl, pyridyl, substituted pyridyl, imidazolyl, substituted imidazolyl, phenyl, substituted phenyl, naphthyl, substituted naphthyl, benzoxazolyl, substituted benzoxazolyl, benzimidazolyl, substituted benzimidazolyl,thiazolyl, substituted thiazolyl, oxazolyl, substituted oxazolyl, benzothiazolyl, substituted benzothiazolyl, pyrazinyl, substituted pyrazinyl, pyridazinyl, substituted pyridazinyl, thiadiazolyl, substituted thiadiazolyl, benzotriazolyl, substituted benzotriazolyl, pyrrolyl, substituted pyrrolyl, indolyl, substituted indolyl, benzothienyl, substituted benzothienyl, thienyl, substituted thienyl, benzofuryl, substituted benzofuryl, furyl, substituted furyl, quinolinyl, substituted quinolinyl, isoquinolinyl, substituted isoquinolinyl, pyrazolyl, and substituted pyrazolyl. Other examples of such ring systems may be found in J. Fletcher, O. Dermer, R. Fox, *Nomenclature of Organic Compounds*, pp. 20–63 (1974), and in the Examples herein.

The term "$C_1$–$C_6$ alkyl" includes such groups as methyl, ethyl, n-propyl, isopropyl, n-butyl, s-butyl, t-butyl, n-pentyl, n-hexyl, 3-methylpentyl, and the like.

The term "halo" and "halogen" refer to chloro, bromo, fluoro, and iodo.

"$C_1$–$C_6$ alkoxy" refers to those groups such as methoxy, ethoxy, propoxy, t-butoxy, and the like.

"$C_2$–$C_6$ alkenyl" refers to those groups such as vinyl, 1-propene-2-yl, 1-butene-4-yl, 1-pentene-5-yl, 1-butene-1-yl, and the like.

"$C_1$–$C_{10}$ alkylthio" refers to those groups such as methylthio, ethylthio, t-butylthio, and the like.

"$C_1$–$C_4$ alkanoyloxy" refers to those groups such as acetoxy, propionoxy, formyloxy, butyryloxy, and the like.

The term "$C_2$–$C_8$ alkenoxy" includes groups such as ethenyloxy, propenyloxy, iso-butoxy ethenyl, and the like.

The term "$C_2$–$C_8$ alkynyl" includes groups such as ethynyl, propynyl, pentynyl, butynyl, and the like.

The term halo-substituted $C_1$–$C_6$ alkyl includes alkyls substituted 1, 2, or 3 times by a halogen, including groups such as trifluoromethyl, 2-dichloroethyl, 3,3-difluoropropyl, and the like.

The term "amine" includes groups such as $NH_2$, $NHCH_2$ and $N(CH)_2$ and the like which may be optionally substituted with halogen, amino, $C_1$–$C_7$ acyloxy, $C_1$–$C_6$ alkyl, $C_1$–$C_6$ alkoxy, nitro, carboxy, carbanoyl, carbanoyloxy, cyano or methylsulphonylamino and the like.

The terms "carboxyl", "carboxymethyl" and "carbamoyl" include the corresponding pharmaceutically acceptable $C_1$–$C_6$ alkyl and aryl esters.

The term "aryl" includes 3 to 8 membered stable saturated or unsaturated organic monocyclic rings having 0 to 4 hetero atoms selected from S, O, and N; and 7 to 10 membered organic stable, saturated or unsaturated, bicyclic rings having 0 to 5 hetero atoms selected from S, O, N; both of which may be substituted by halo, $C_1$–$C_6$ alkyl, $C_1$–$C_6$ alkoxy, $C_2$–$C_6$ alkenyl, $C_2$–$C_6$ alkynyl, substituted $C_1$–$C_6$alkyl, $C_1$–$C_6$ substituted alkoxy, substituted $C_2$–$C_6$ alkenyl, or substituted $C_2$–$C_6$ alkynyl, substituted alkoxy, amino, nitro, cyano, carboxy, hydroxymethyl, aminomethyl, carboxymethyl, $C_1$–$C_4$ alkylthio, hydroxy, $C_1$–$C_4$ alkanoyloxy, carbamoyl, or halo-substituted $C_1$–$C_6$ alkyl.

The terms substituted alkyl, substituted alkenyl, substituted alkynyl and substituted alkoxy are these substitutents substituted with halogen, hydroxy, amino, $C_1$–$C_7$ acyloxy, nitro, carboxy, carbanoyl, carbanoyloxy, cyano, methylsulfonylamino, or $C_1$–$C_6$ alkoxy, and may be substituted once or twice with the same or different group.

Preferred definitions are when $R_3$ and $R_4$ are hydrogen; and $R_1$ is a heteroaromatic monocyclic or bicyclic ring as defined above and has the N'-linkage at the 3 position, or more preferably at the 2 position, relative to a hetero atom Examples of $R_1$ are thiazolyl, (4-methyl)thiazolyl, (4,5-dimethyl)thiazolyl, (4-cyano)thiazolyl, (4-trifluoromethyl) thiazolyl, benzothiazolyl, (6-fluoro)benzothiazolyl, (6-chloro)pyraziny, (4-ethyl) thiazolyl, 4-(3-pyridyl) thiazolyl, 4-(3-nitrophenyl)thiazolyl, pyridyl, (6-bromo) pyridyl, (6-chloro)pyridyl, (6-methyl)pyridyl, (5-methyl) pyridyl, (6-trifluoromethyl)pyridyl, (5-trifluoromethyl) pyridyl, (6-ethyl)pyridyl, (5-ethyl)pyridyl, (6-bromo) pyrazinyl, 3-(6-bromo)pyridazinyl, (5-cyano)pyridyl, (5-cyano)pyridyl, (5-cyano)pyrazinyl, (6-cyano)pyrazinyl, 3-(6-cyano)pyridazinyl, 1,3,4-thiadiazoyl, benzimidazolyl, imidazolyl, (5-bromo)pyridyl, (5-chloro)pyridyl, (5-chloro) pyrazinyl, (5-bromo)pyrazinyl, (6-chloro)pyridazinyl, 2-(3-[6-bromo]pyridazinyl), 2-(3-[6-chloro]pyridazinyl) 2-(3-[6-cyano]pyridazinyl), 2-(3-ethyl)pyridyl, 3-(6-methoxy) pyridazinyl, 2-(5-nitro)pyridyl, 2-(5,6-dichloro-4-azabenzimidazolyl), 4-(6-aminopyrimidinyl), 4-pyrimidinyl, 2-(3-pyridazlnyl), 2-(3-(6-methyl) pyridazinyl, 2-pyrazinyl, 2-(5-methyl)pyrazinyl); and $R_2$ are (4-methyl) -3-pentenyl, (±)-cis-N-(3,4-benzo-cis-bicyclo-[3.1.0]-hexen-6-yl),

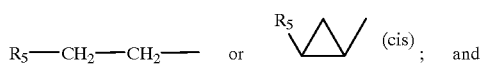

The preferred optional substituents for $R_1$ comprise mono, di, or tri halo, preferably bromo or chloro, especially para to the N'-linkage.

The preferred optional substituents to $R_5$ are halo or $C_1$–$C_6$ alkoxy, especially 2,6-difluoro and 2,6-dihalo-3-$C_1$–$C_6$ alkoxy.

Preferred $R_5$ groups include phenyl, 2-methoxyphenyl, 3-methoxyphenyl, 4-methoxyphenyl, 2-ethoxyphenyl, 2-methylphenyl, 3-methylphenyl, 2-fluorophenyl, 2,6-difluorophenyl, 2-fluoro-6-methoxyphenyl, 2-fluoro-6-ethoxyphenyl, 2,3,5,6-tetrafluorophenyl, 2-chlorophenyl, 3-chlorophenyl, 1-cyclohexenyl, 2-naphthyl, 2,5-dimethoxyphenyl:, 2-azidophenyl, 2,3,4-trifluorophenyl, 2-fluoro-6-chlorophenyl, 2,6-dimethoxyphenyl, 2,3,6-trichlorophenyl, 2,6-dichlorophenyl, 2,3,5-trichlorophenyl, 3,5-dichlorophenyl, 3-fluorophenyl, 2,4-dimethoxyphenyl, 2-pyridyl, 2-(6-methoxy)pyridyl, 2-(6-ethoxy)pyridyl, 2-(6-fluoro)pyridyl, 2-(5-fluoro)pyridyl, 2-(4-fluoro)pyridyl, 2-(3-fluoro)pyridyl, 2-(6-chloro)pyridyl, 2-(5-chloro) pyridyl, 2-(4-chloro)pyridyl, 2-( 3-chloro)-pyridyl, 2-(5-methoxy-6-fluoro)pyridyl, 2-(3-methoxy-6-fluoro)pyridyl, 2-(6-methoxy-3-fluoro)pyridyl, 2-(5-ethoxy-6-fluoro) pyridyl, 2-(3-ethoxy-6-fiuoro)pyridyl, 2-(6-ethoxy-3-fluoro) pyridyl, 2-(5,6-difiuoro)pyridyl, 2-(3,6-difluoro)pyridyl, 2-(5,6-dichloro)-pyridyl, 2-(3,6-dichloro)pyridyl, 2-(6-methoxy)pyridyl, 2-(6-ethoxy)pyridyl, 2-[1,3-pyrimidyl], 2-pyrazinyl, 3-pyridazinyl, 2,6-difluoro-3-methoxyphenyl, 2,6-difluoro-3-ethoxyphenyl, 2,6-difluoro-4-methoxyphenyl, 2,6-difluoro-4-ethoxyphenyl, 2-(3-ethoxy) pyridyl, 2-(3-methoxy)pyridyl, 2,6-difluorophenyl, 2,6-difluoro-3-N-methyl-carboxamidephenyl, 2-fluoro-6-chlorophenyl, 3-bromo-6-methoxyphenyl, 3-ethoxyphenyl, 3-bromo-6-ethoxyphenyl, 3-(2-fluoro)pyridyl, (2-vinyl) phenyl, (3-vinyl)phenyl, (3-methoxy-carbonyl)phenyl, 5,6-dimethylbenzotriazolyl, 2,3-difluoro-6-methoxyphenyl, 2,6-difluoro-3-cyanophenyl, 3-ethynylphenyl, and 2,5-diethoxyphenyl.

A further aspect of the invention provides novel compounds within the above Formula 1A, wherein A is as defined above;

$R_1$ is a stable, unsaturated, substituted or unsubstituted heterocycle having i) a 3 to 8 membered monocyclic ring with up to 4 hetero atoms or ii) a 7 to 10 membered bicyclic ring with up to 5 hetero atoms wherein the N'-bonded ring has at least one of the hetero atoms and wherein the hetero atoms are selected from N, O and S;

$R_2$ is a group of the formula

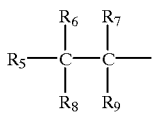

wherein $R_5$ is a stable, saturated or unsaturated, substituted or unsubstituted, i) 3 to 8 membered organic monocyclic ring having 0 to 4 hetero atoms or ii) a 7 to 10 membered organic bicyclic ring having 0 to 5 hetero atoms, the hetero atoms being selected from S, O and N;

and $R_6$, $R_7$, $R_8$ and $R_9$ are independently $C_3-C_8$ cycloalkyl, hydrogen, $C_1-C_6$ alkyl, $C_2-C_6$ alkenyl, $C_2-C_6$ alkynyl, substituted $C_1-C_6$ alkyl, substituted $C_2-C_6$ alkenyl, or substituted $C_2-C_6$ alkynyl, $C_1-C_6$ substituted alkoxy, halo, amino, nitro, cyano, $C_1-C_5$ alkoxy, hydroxy, hydroxymethyl, aminomethyl, carboxymethyl, $C_1-C_4$ alkylthio, $C_1-C_4$ alkanoyloxy, carbamoyl, or a halo substituted $C_1-C_6$ alkyl; or two of which, along with the carbons to which they are attached, combine to form a stable, saturated or unsaturated, substituted or unsubstituted, 3 to 7 membered organic monocyclic ring having 0 to 4 hetero atoms selected from S, O, or N; or $R_6$ and $R_8$, or $R_7$ and $R_9$, along with the carbon to which they are attached, form a stable, saturated or unsaturated, substituted or unsubstituted, 3 to 7 membered organic monocyclic ring having 0 to 4 hetero atoms selected from S, O, or N; or a pharmaceutically acceptable salt thereof, with the provisos that:

a) if $R_6-R_9$ are all hydrogen, then the following combinations are excluded:

|  | A | $R_1$ | $R_5$ |
|---|---|---|---|
| i | O | 6-chloropyridazin-3-yl | morpholine |
| ii | O | 1-oxy,2,2,5,5 tetramethyl-pyrrol-3-yl | isoindole |
| iii | O | (substituted) 4-carboxy-fur-3-yl | piperazine, (substituted) phenyl |
| iv | O | benzimidazol-2-yl | phenyl |
| v | O | purin-6-yl | imidazole, (substituted) phenyl |
| vi | O | (substituted) oxazol-2-yl | phenyl |
| vii | O | benzothien-3-yl | morpholine |
| viii | NH | pyrimidin-2-yl | phenyl |
| ix | NH | imidazol-2-yl | (substituted) phenyl |
| x | NCN | pyrid-3-yl | phenyl | b) if $R_7$ is methyl or together with $R_6$ forms cyclopropyl and the remainder of $R_6-R_9$, are hydrogen, then the following combination is excluded:

| A | $R_1$ | $R_5$ |
|---|---|---|
| O | pyrid-2-yl | phenyl; and | c) if $R_7$ is alkylthio, and the remainder of $R_6-R_9$ are hydrogen, then the following combination is excluded

| A | $R_1$ | $R_5$ |
|---|---|---|
| O | pyrid-3-yl | phenyl. |

The definitions above also apply to these compound aspects of the invention with She exception that aryl and substituted aryl are excluded as possible optional substituents to group $R_1$.

Further, preferred compounds of the invention are those in which $R_1$, and $R_6-R_9$ are as defined above and $R_5$ is substituted or unsubstituted $C_2-C_6$ alkenyl, $C_2-C_6$ alkynyl or wherein $R_5$ is —$OR_{10}$ or —$C(O)R_{10}$ where $R_{10}$ is $R_5$ as defined above, or substituted or unsubstituted $C_2-C_6$ alkenyl or $C_2-C_6$ alkynyl.

It is believed that none of the compounds excluded by the provisos except proviso x) have been known in a therapeutic role and thus, a further aspect of the invention includes the compounds embraced by the provisos for use in therapy.

As mentioned above, the invention includes pharmaceutically acceptable salts of the compounds defined by the above formula (I). Although generally neutral, a particular compound of this invention can possess a sufficiently acidic, a sufficiently basic, or both, functional groups, and accordingly react with any of a number of nontoxic inorganic bases, and nontoxic inorganic and organic acids, to form a pharmaceutically acceptable salt. Acids commonly employed to form acid addition salts are inorganic acids such as hydrochloric acid, hydrobromic acid, hydroiodic acid, sulfuric acid, phosphoric acid and the like, and organic acids such as p-toluene sulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, g-hydroxybutyrate, glycollate, tartrate, methanesulfonate, propanesulfonate, naphthalene-1-sulfonate, naphthalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and One like. Such bases useful in preparing the salts of this invention thus include sodium hydroxide, potassium hydroxide, ammonium hydroxide, potassium bicarbonate, calcium hydroxide, calcium carbonate, and the like.

The pharmaceutically acceptable salts of the invention are typically formed by reacting a compound as defined with an equimolar or excess amount of acid or base. The reactants are generally combined in a mutual solvent such as diethyl ether or benzene, for acid addition salts, or water or alcohols for base addition salts, and the salts normally precipitate out of solution within about one hour to about ten days and can be isolated by filtration or other conventional methods. The salts of the compounds of the invention will convert to the compound Per se after administration and are thus prodrugs. All prodrugs are administered in an amount sufficient to generate an effective amount of the compound to contact the virus and interact with it (e.g. inhibit replication thereof).

The compounds of the present invention also include racemates, racemic mixtures, and individual enantiomers or diastereomers. All asymmetric forms, individual isomers and combinations thereof are within the scope of the present invention.

As noted, the optically active diastereomers of the compounds of Formula 1 are considered part of this invention and such optically active isomers may be prepared from their respective optically active precursors by the procedures described herein, or by resolving the racemic mixtures. The resolution can be carried out in the presence of a resolving agent, by chromatography, by repeated crystallization or by some combination of these techniques which are known to those skilled in the art. Further details regarding resolutions can be found in Jacques, et al., *Enantiomers, Racemates, and Resolutions*, John Wiley & Sons 1981.

The compounds of the present Invention, or their precursors, are prepared using procedures known to those of ordinary skill in the art. More particularly, the compounds of Formula (1) are prepared according to the general procedures shown below in Schemes I–IV, and VII, as described below.

In Scheme I, a derivative of an isocyanate

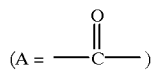

or isoselenocyanate

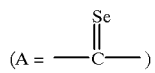

is reacted with with an amino group (2) in approximately 1:1 molar ratio, in an inert organic solvent, such as N,N-dimethyl formamide and stirred at an appropriate temperature of between about 0–150° C. for a period of time between 1 and 72 hours. The time and temperature used depends upon he reactivity of the individual reagents. The product (3) may be isolated by conventional techniques.

Scheme II is run under the same general reaction conditions as Scheme I. Where

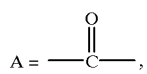

Schemes I and II are processes analogous to that described in *Advanced org. Chem.* 3rd Ed., J. March, p 802, 1985, J. Wiley & Sons and references cited therein, incorporated herein by reference. Wherein

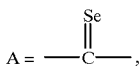

Schemes I and II are processes analogous to that described in *Ber. Deutsch Chem. Ges.*, 100, 1459, 1967; *J. Chem. Soc. Chem. Commun.*, 372, 1968; *J. Prakt. Chem.*, 315, 155, 1973 and references cited therein, incorporated herein by reference. Wherein A=SO$_2$, Schemes I and II are processes analogous to that described in *J. Am. Chem. Soc.*, 94, 6135,.1972 and *Org.*

Prep. Proced. Int., 16, 49, 1984 and references cited therein, incorporated herein by reference.

SCHEME I

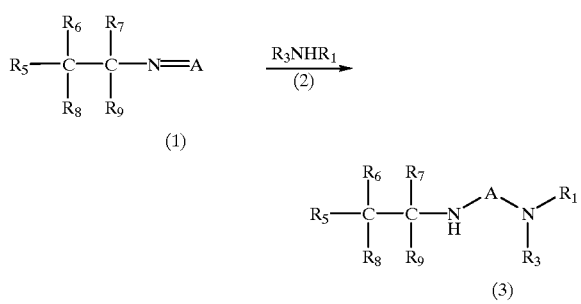

SCHEME II

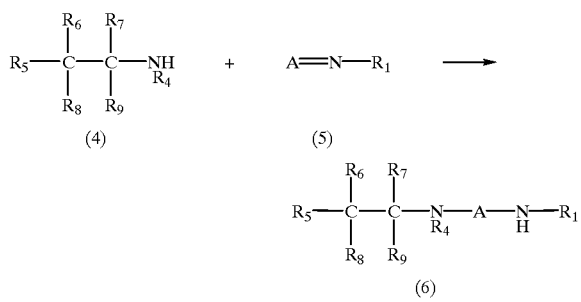

In Scheme III, a derivative of an amine (7) and an amine (8) are added in an inert solvent, such as N,N-dimethyl formamide, tetrahydrofuran, ethyl acetate, or benzene, to an appropriately substituted derivative (9) wherein L$_1$ and L$_2$ represent leaving groups. The reaction is stirred at an appropriate temperature of between about 0–150° C. for a period of time between 1 and 72 hours. The time, temperature, and sequence of addition used depends upon the reactivity of the individual reagents. The product (10) may be isolated by conventional techniques.

Wherein

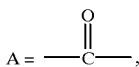

Scheme III is a process analogous to that described in *J. Org. Chem.*, 56, 891, 1991 and references cited therein, incorporated herein by reference.

Wherein

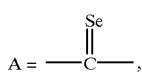

Scheme III is a process analogous to that described in *Bull. Chem. Soc. Jpn.*, 62, 2419, 1989 and references cited therein, incorporated herein by reference.
Wherein

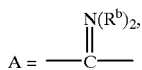

Scheme III is a process analogous to that described in *J. Org. Chem.*, 24, 1157, 1959; *J. Org. Chem.*, 38, 155, 1973; *J. Med. Chem.*, 20, 901, 1977; *Tetrahedron Lett.*, 30, 7313, 1989; *Org. Prep. Proced. Int.*, 17, 256, 1985; *J. Heterocyclic Chem.*, 24, 275, 1987; *Org. Prep. Proced. Int.*, 23, 721, 1991 and references cited herein, incorporated herein by reference.
Wherein

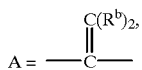

Scheme III is a process analogous to that described in Angew. Chem. Int. Ed., 26, 1165, 1987; *Liebigs Ann. Chem.*, 207, 1990; European Patent 58492, 1982; *Syn. Commun.*, 19, 943, 1989; *J. Heterocyclic Chem.*, 26, 1335, 1989; Belgium Patent 894093, 1982; *Syn. Commun.*, 21, 1213, 1991; *Synthesis*, 195, 1990; U.S. Pat. No. 4,968,808; *j. Org. Chem.*, 32, 2661, 1967; *Synthesis*, 76, 1987 and references cited therein, incorporated herein by reference. Wherein A=SO$_2$, Scheme III is a process analogous to that described in *Synthesis*, 192, 1983; *J. Org. Chem.*, 45, 5371, 5373, 1980; Org. Syn. Coll. Vol. VI, 78, 1988; *J. Prakt. Chem.*, 29, 328, 1965; *Arch. Pharm.*, 321, 375, 1988; *J. Chem. Soc.*, 4367, 1960; *Synthesis*, 576, 1972 and references cited therein, incorporated herein by reference.

SCHEME III

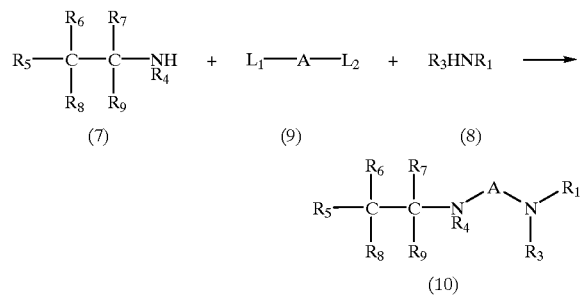

In Scheme IV, a thiourea derivative (11) is converted to the corresponding derivative (10). Wherein

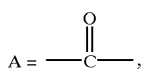

Scheme IV is a process analogous to that describe in *J. Org. Chem.*, 26, 2925, 1961 and *Tetrahedron Lett.*, 27, 3911, 1986 and references cited therein, incorporated herein by reference. Wherein

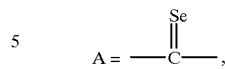

Scheme IV is a process analogous to that described in *Eur. J. Med. Chem.*, 16, 317, 1981 and references cited therein, incorporated herein by reference. Wherein

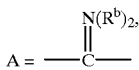

Scheme IV is a process analogous to that described in *J. Org. Chem.*, 49, 4123, 1984; J. Med. Chem., 20, 901, 1977; *Tetrahedron Lett.*, 30, 7313; 1989; *Syn. Commun.*, 13, 67, 1983; and *Curr. Sci.*, 37, 645, 1968 and references cited therein, incorporated herein by reference.

SCHEME IV

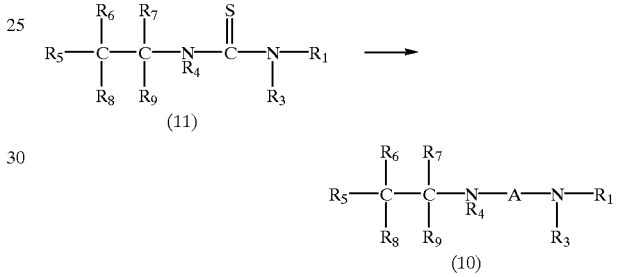

In Scheme V, a carbodiimide derivative (12) is reacted with a nucleophile to form the corresponding product (13). Wherein

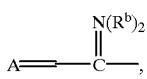

scheme V is a process analogous to that described in U.S. Pat. No. 4,414,211, 1980; *J. Chem. Soc. C*, 1429, 1970; *J. Chem. Soc. P. T.* 1, 1241, 1977; *J. Med. Chem.*, 32, 228, 1989 and references cited therein, incorporated herein by reference. Wherein

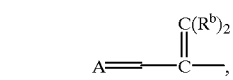

Scheme V is a process analogous to that described in *Monat. fur Chem.*, 97, 695, 1966 and *Chem. Ztq.*, 112, 107, 1988 and references cited therein, incorporated herein by reference.

SCHEME V

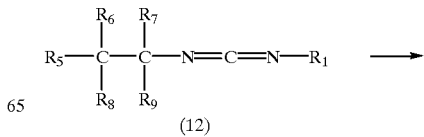

(13)

$$R_5-\underset{\underset{R_8}{|}}{\overset{\overset{R_6}{|}}{C}}-\underset{\underset{R_9}{|}}{\overset{\overset{R_7}{|}}{C}}-\underset{H}{N}-A-\underset{H}{N}-R_1$$

In Schemes VI and VII, derivatives 14 and 15, wherein L represents a leaving group, is reacted with a nucleophile to afford the corresponding derivatives 16 and 17, respectively. Wherein $$A=\!\!=\!\!\overset{\overset{O}{\|}}{C}-,$$

Schemes VI and VII are processes analogous to that described in *Org. Syn. Coll.* Vol. V, 966, 1973 and references cited therein, incorporated herein by reference. Wherein $$A=\!\!=\!\!\overset{\overset{N(R^b)_2}{\|}}{C}-,$$

Schemes VI and VII are processes analogous to that described in *J. Org. Chem.*, 51, 1882, 1986; *Syn. Comm.*, 20, 217, 1990, *Tetrahedron Lett.*, 1879, 1970, *Org. Prep. Proced. int.*, 17, 256, 1985; *J. Heterocyclic Chem.*, 24, 275, 1987; *Org. Prep. Proced. Int.*, 23, 721, 1991 and references cited therein, incorporated herein by reference. Wherein $$A=\!\!=\!\!\overset{\overset{C(R^b)_2}{\|}}{C}-,$$

Scheme VI and VII is a process analogous to that described in Ann. Chem., 2096, 1979 and references cited therein, incorporated herein by reference.

SCHEME VI

(14) → (16)

SCHEME VII

(15) →

(17)

Compounds wherein $Z_{ii}$ is $S(=O)_2$ can be prepared by reacting an amine of the formula $R_2NH_2$ with diaminosulfone, for instance under reflux in 1,2-dimethoxymethane, to form a compound of the formula $R_2NHS(=O)_2NH_2$. This, in turn, is subjected to reaction with a compound of the formula $H_2NR_1$, for instance, in DMF or 1,2-dimethoxyethane, to form $R_2NHS(=O)_2NHR_1$. This process is, thus, analogous to that described in Arya et al., *Ind. J. Chem. B*, 1976, 14B, 766.

Alternatively, compounds wherein $Z_{ii}$ is sulphone can be prepared by reacting an amine of the formula $R_2NH_2$ with a dihalosulphone, e.g. $SO_2Cl_2$, for instance under reflux with $SbCl_5$ and acetonitrile to produce a compound of the formula $R_2NHS(=O)_2$halo which can be reacted with the appropriate $R_1$ amine, for example 2-amino, 6-chloropyridyl in acetonitrile and triethylamine. This process is analogous to *Liebigs Ann. Chem.* 729 (1969) 40.

Compounds wherein $Z_{ii}$ is So can be prepared by reducing compounds prepared by the above two methods using conventional reduction techniques. Alternatively, a sulfinyl compound can be prepared by the methodology in *Liebigs Ann. Chem.* 1979, 1756, where $SOCl_2$ is reacted with several molar equivalents of an aryl leaving group such as pyridyl to form a dipyrid-1-ylsulphinyl intermediate. This, in turn, can be transaminated with appropriate $R_1$ and $R_2$ amines as described in *Tetrah. Lett.* 1985, 26, 3821, to produce a compound of the structure $R_2NHSONHR_1$.

Tests with the above compounds of Formula 1 have indicated activity as inhibitors of HIV. While not being bound by theory, it is believed that the compounds act as reverse transcriptase inhibitors, and thereby act to inhibit replication of the virus.

The HIV inhibition activity of the present invention is generally between 1 and 3 logs greater against HIV-1 strains than against HIV-2 strains. This enables the compounds and compositions of the present invention to be used to selectively inhibit HIV-1 growth in cell cultures where co-infection with HIV-1 and HIV-2 is suspected. Suppression of one strain or the other is necessary to enable appropriate choice of antiviral agent to combat each strain. In practice, selective inhibition of HIV-1 in a co-infected cell culture entails administering a concentration of a compound of the present invention which is intermediate the respective $IC_{50}$ or more preferably the $IC_{90}$ for that compound against HIV-1 and HIV-2. The cell culture is subject to an appropriate incubation time, which is selected to be sufficiently long to disable the infectivity of the HIV-1 virions, but not sufficiently long as to encourage the development of resistant mutants, for example between 24 and 48 hours. The supernatent is subject to limiting dilution, preferably in a conventional resuscitation buffer to sequester any remaining compound, until it is statistically likely that only a single infectious dose of HIV-2 virons is left. This is then reinoculated in order to determine, for example, the resistance profile or anti-viral susceptibility of the HIV-2 strain uninfluenced by the co-infection with HIV-1.

The following is a description of the test systems used in analyzing compounds in effectiveness against HIV.

Tests A, B, C, and D (XTT)

MT4 cells in a medium of RPMI 1640, 5% FCS, penicillin/streptomycin are adjusted to $2\times10^5$ cells/ml and seeded into microplates (96 wells/plate) 100 ml cell suspension/well giving 2×10⁴ cells/well. The compound to be tested is made into a 10 mg/ml mixture in DMSO and stored at −20° C. The compound in DMSO is diluted with medium containing 10% DMSO in a 10-fold dilution series to give 1 mg/ml, 10 mg/ml, and 100 mg/mn solutions. Further dilutions to 400, 40, 4 and 0.4 mg/ml are made in medium containing microplates. Fifty ml of the 400, 40, and 4 mg/ml are transferred to the cell-containing microplates with a multi-channel pipette (final concentration: 100, 10, and 1 mg/ml). Finally, 50 ml of virus suspension is added to each well (with a repetitive "Eppendorf" multipipett). Each plate has at least six wells with the following: [Test A: HIV virus; Test B: HIV(II) virus; Test C: SIV virus; Test D: No virus]; with no drug (virus control) and six wells without virus (medium control). The plate is put into a plastic bag and incubated for six days in $CO_2$ atmosphere. To each well in the plate is added 50 ml of XTT ((2,3-bis[2-methoxy-4-nitro-5-sulfophenyl]-5-[(phenylamin o)carbonyl]-2H-tetrazolium hydroxide), (1 mg/ml 0.01–0.02 mM N-metyl-phenazonium methosulfate). After six hours of incubation in $CO_2$ atmosphere the plates are covered with adhesive plate sealers and gently mixed on a vortex. Optical densities are determined at a wavelength of 450 nm and a reference wavelength of 650 nm. The percent reduction of cytotoxocity caused by the virus infection is calculated as follows:

$$\frac{OD_{450}\ compound - OD_{450}\ inf\ cells}{OD_{450}\ uninf\ cells - OD_{450}\ inf\ cells} \times 100$$

Tests E, F, G, H (HIV-IRT, HIV-2RT, SIVRT, no Virus)

MT-4/H9-cells are adjusted to 2×10⁵ cels/ml medium (RPMI 1640, 5% FCS, penicillin/streptomycin) and seeded into microplates (96 wells/plate) 100 ml cell suspension/well giving 2×10⁴ cells/well. The compound to be tested is made 10 mg/ml in DMSO=stock solution (stored at −20° C.). The compound dissolved in DMSO is diluted 25 times in medium to give 400 mg/ml. Further dilutions to 40 mg/ml and 4 mg/ml are made in microplates.

50 ml of the dilutions 400 mg/ml, 40 mg/ml and 4 mg/ml are transferred to the "cell-containing" microplate with a multichannel pipette. (Final concentration: 100, 10 and 1 mg/ml).

Finally 50 ml of virus suspension is added to each well (with a repetitive "Eppendorf multipett"). [Test E-HIV-1; Test F-HIV-2; Test G-SIV; Test H-no virus].

Each plate has at least four wells with virus but no drug (virus control) and two wells without virus (medium control). The plate is put into a plastic bag to avoid evaporation and incubated for six days in $CO_2$-atmosphere. 10 ml supernatant from each well is transferred with a multichannel pipette into a new microplate to which 40 ml VDB, (50 mM Tris-HCl pH=7.6, 35 mM KCl, 4 mM DTT, 1 mM EDTA, 1.3% Triton X-100), have been added to each well. The addition of 50 ml RT-reaction mix, (10 ml culture supernatant, 40 ml VDB and 50 ml reaction mixture giving a final concentration of: 100 mM Tris-HCl pH=7.6, 100 mM KCl, 4 mM $MgCl_2$, 4 mM DTT, 275 mg/ml BSA/ml, 5 mg $(rA)_n(dT)_{12-18}$/ml and 0.3 mM $^3H$ dTTP (specific activity 18.000 cpm/pmol)) gives a final volume of 100 ml/well. After 60 minutes of incubation the whole assay volume is transferred by use of a cell harvester to a filter mat prewetted with 5% TCA. The filter is washed in 5% TCA and rinsed once in ethanol. After drying the filter mat at 60° C. for 30 min. each filter (96/mat) is punched out and put into counting vials 2 ml of scintillation fluid is added and the samples are counted (1 min) or the whole filter mat is put into a plastic bag, 10 ml of scintillation fluid is added and the filter mat is counted in a Beckman Betaplare counter. Percent reduction of RT activity is determined by comparing RT activity for virus control with the RT activity measured for each dilution of the compound.

Test I (HIVRT (rAdt))

The compounds were tested for direct inhibitory activity on HIV-RT in a volume of 100 ml recombinant HIV-RT (diluted in virus disruption buffer to give 200.000 cpm)

100 MM Tris-HCl pH 7.6, 100 mM KCl, 4 mM $MgCl_2$, 4 mM DTT, 275 mg/ml BSA, 0.5 mg $(rA)n(dT)_{12-18}$ and 0.3 mM $^3H$-=dTTP (specific activity 18.000 cpm/mol). After 60 minutes of incubation 40 ml in duplicate were spotted on paper discs and washed in 5% TCA. After rinsing the paper discs in ethanol they were dried and counted in scintillation fluid.

The following illustrate activities of compounds in the above-described tests. The numbers represent % inhibition.

| Test | 100 µg/ml | 10 µg/ml | 1 µg/ml | 0.1 µg/ml | 0.01 µg/ml | 0.001 µg/ml | 0.1 µg/ml | IC50 µg/ml |
|---|---|---|---|---|---|---|---|---|

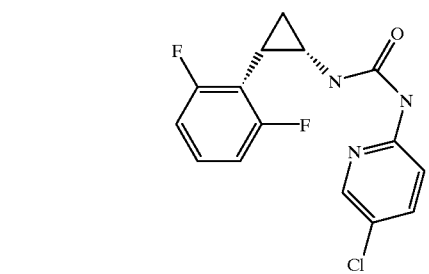

| I | | 100 | 98 | 89 | 55 | 6 | | 0.0008 |
| I | | 100 | 97 | 93 | 62 | 16 | | 0.0005 |
| A | 3 | 100 | 86 | 82 | 80 | 7 | | |
| A | 100 | 100 | 90 | 100 | 81 | 8 | | |

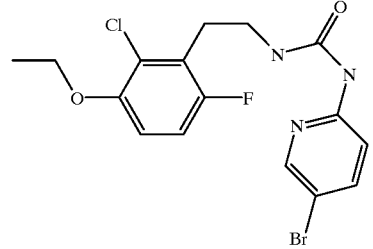

| I | | 98 | 96 | 82 | 41 | 13 | | 0.002 |
| I | | 100 | 100 | 83 | 45 | 18 | | 0.0014 |
| A | 100 | 100 | 98 | 92 | 96 | 5 | | |
| A | 100 | 83 | 99 | 89 | 82 | 47 | | |

-continued

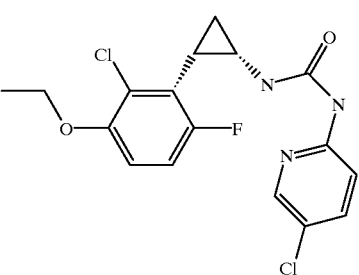

| | | | 99 | 96 | 82 | 46 | 19 | 0.0011 |
| I | | | 97 | 96 | 80 | 30 | 5 | 0.002 |
| A | 24 | 88 | 87 | 100 | 100 | 0 | | |
| A | 30 | 100 | 100 | 100 | 100 | 19 | | |

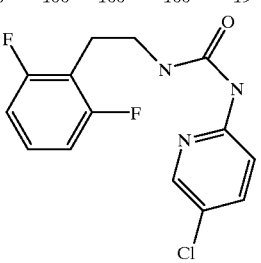

| I | | | 100 | 100 | 91 | 58 | 17 | 0.0006 |
| A | 0 | 100 | 87 | 92 | 51 | 0 | | |
| A | 0 | 93 | 98 | 100 | 94 | 6 | | |

| Example | Test | IC$_{50}$ ($\mu$g/ml) |
| --- | --- | --- |
| 56 | I | 0.0023, 0.0022 |
| 57 | I | 0.0004, 0.0005, 0.0004 |
| 58 | I | 0.038 |
| 26 | I | 0.009, 0.01 |
| 27 | I | 0.0005, 0.0006 |
| 23 | I | 0.005, 0.014 |
| 34 | I | 0.0004 |
| 33 | I | 0.0005 |
| 21 | I | 0.05 |
| 64 | I | 0.0013 |

A feature of this invention also disclosed is a method of administering to a human in need thereof the compounds described, their pharmaceutically acceptable salts or prodrugs thereof to treat or inhibit HIV/AIDS, to inhibit the replication of the HIV/AIDS virus in infected human cells and to inhibit AIDS from developing n humans infected with the HIV/AIDS virus or carrying antibodies to the HIV/AIDS virus.

The present invention also discloses the compounds of the invention and their salts for use in the treatment of the condition referred to above, as well as the use of such compounds in the preparation of pharmaceutical formulations for the treatment of such conditions.

In general for the treatment as described above, a suitable effective dose of the compound or its pharmaceutically acceptable salt will be in the range or 0.5 to 250 mg per kilogram bodyweight of recipient per day. Administration may be by any suitable route including oral, rectal, nasal, topical (including buccal and sublingual), vaginal or parenteral (including subcutaneous, intramuscular, intravenous and intradermal) administration. It will be appreciated that the preferred route may vary with, for example, the condition, age, and weight of the recipient.

The administered ingredients may be used as a therapy in conjunction with other therapeutic agents, (other anti-virals, anti-bacterials, compounds useful for preventing resulting secondary or contemporaneous afflictions associated with HIV/AIDS) such as AZT, ddI, ddC, 9-[[2-hydroxy-1-(hydroxymethyl)ethoxy]methyl]guanine, 9-(2-hydroxyethoxymethyl)guanine(acyclovir), 2-amino-9-(2-hydroxyethoxymethyl)purine, suramin, ribavarin, antimoniotungstate (HPA-23), interferon, e.g., a interferon, interleukin II, and phosphonoformate (Foscarnet) or in conjunction with other immune modulators including bone marrow or lymphocyte transplants or other medications such as levamisol or thymosin which would increase lymphocyte numbers and/or function as is appropriate.

While it is possible for the administered ingredients to be administered alone, it is preferable to present them as part of a pharmaceutical formulation. The formulations of the present invention comprise at least one administered ingredient, as above-defined together with one or more acceptable carriers thereof and optionally other therapeutic ingredients. The carrier(s) must be "acceptable" in the sense of being compatible with the other ingredients of the formulation and not deleterious to the recipient thereof.

The formulations include those suitable for oral, rectal, nasal, topical (including buccal and sublingual), vaginal or parenteral (including subcutaneous, intramuscular, intravenous and intradermal) administration. The formulations may conveniently be presented in unit dosage form, e.g., tablets and sustained release capsules, and may be prepared by any methods well known in the art of pharmacy.

Such methods include the step of bringing into association the to be administered ingredients with the carrier which constitutes one or more accessory ingredients. In general, the formulations are prepared by uniformly and intimately bringing into association the active ingredients with liquid carriers or finely divided solid carriers or both, and then if necessary shaping the product.

Formulations of the present invention suitable for oral administration may be presented as discrete units such as capsules, cachets or tablets each containing a predetermined amount of he active ingredient; as a powder or granules; as a solution or a suspension in an aqueous liquid or a non-aqueous liquid; or as an oil-in-water liquid emulsion or a water-in-oil liquid emulsion and as a bolus, etc.

With regard to compositions for oral administration (e.g. tablets and capsules), the term "suitable vehicle" means common excipients such as binding agents, for example, syrup, acacia, gelatin, sorbitol, tragacanth, polyvinylpyrrolidone (Povidone), methylcellulose, ethylcellulose, sodium carboxy-methylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; disintegrators such as microcrystalline cellulose, corn starch, sodium starch glycolate, alginic acid; and lubricants such as magnesium stearate and other metallic stearates, stearic acid, silicone fluid, talc, waxes, oils and colloidal silica. Flavoring agents such as peppermint, oil of wintergreen, cherry flavoring or the like can also be used. It may be desirable to add a coloring agent to make the dosage form more aesthetically pleasing in appearance or to help identify the product. The tablets may also be coated by methods well known in the art.

A tablet may be made by compression or molding, optionally with one or more accessory ingredients. Compressed tablets may be prepared by compressing in a suitable machine the active ingredient in a free-flowing form such as a powder or granules optionally mixed with a binder, lubricant, inert diluent, preservative, surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Formulations suitable for topical administration include lozenges comprising the ingredients in a flavored basis, usually sucrose and acacia or tragacanth; pastilles comprising the active ingredient in an inert basis such as gelatin and glycerin, or sucrose and acacia; and mouthwashes comprising he ingredient to be administered in a suitable liquid carrier.

Formulations suitable for topical administration to the skin may be presented as ointments, creams, gels and pastes comprising the ingredient to be administered and a pharmaceutically acceptable carrier. An exemplary topical delivery system is a transdermal patch containing the ingredient to be administered.

Formulations for rectal administration may be presented as a suppository with a suitable base comprising, for example, cocoa butter or a salicylate.

Formulations suitable for nasal administration wherein the carrier is a solid include a coarse powder having a particle size, for example, in the range 20 to 500 microns which is administered in the manner in which snuff is taken, i.e., by rapid inhalation through the nasal passage from a container of the powder held close up to the nose. Suitable formulations wherein the carrier is a liquid, for administration, as for example, a nasal spray or as nasal drops, include aqueous or oily solutions of the active ingredient.

Formulations suitable for vaginal administration may be presented as pessaries, tampons, creams, gels, pastes, foams, or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, or example water for injections, immediately prior to use. Extemporaneous injection solutions and suspensions may be prepared from sterile powders, granules, and tablets of the kind previously described.

Preferred unit dosage formulations are those containing a daily dose or unit, daily sub-dose, as herein above recited, or an appropriate fraction thereof, of the administered ingredient.

The antiviral compounds of Formula I can be used as surface disinfectants. Solutions containing as little as 0.1 percent by weight of the antiviral compound maybe effective for disinfecting purposes. Preferably, such solutions also can contain a detergent or other cleansing agent. The solutions maybe useful for disinfecting objects such as glassware, dental and surgical instruments, and surfaces such as walls, floors, and tables in areas where maintenance of sterile conditions is important, for example, hospitals, food-preparation areas, and the like.

In practicing the method for treating or inhibiting HIV and/or AIDS, the antiviral can be administered in a single daily dose or in multiple doses per day. The treatment regime may require administration over extended periods of time, e.g., for several days or for several months or years. The amount administered per dose or the total amount administered will depend on such factors as the nature and severity of the infection, the age and general health of the patient, the tolerance of both the patient and the microorganism or microorganisms involved in the infection to the antiviral compound.

The following formulation examples represent specific pharmaceutical formulations employing compounds comprehended by the present method. The formulations may employ as active compounds any of the compounds of Formula I or a pharmaceutically acceptable salt thereof. The examples are illustrative only and are not intended to limit the scope of the invention in any way.

Formulation 1

Hard gelatin capsules are prepared using he following ingredients:

|  | Quantity (mg/capsule) |
| --- | --- |
| Compound | 1250 |
| Starch dried | 200 |
| Magnesium stearate | 10 |

The above ingredients are mixed and filled into hard gelatin capsules in 460 mg quantities.

Formulation 2

A tablet formula is prepared using the ingredients below:

|  | Quantity (mg/tablet) |
| --- | --- |
| Compound | 250 |
| Cellulose, microcrystalline | 400 |
| Silicon dioxide, fumed | 10 |
| Stearic acid | 5 |
| Magnesium stearate | 10 |

The components are blended and compressed to form tablets each weighing 675 mg.

Formulation 3

An aerosol solution is prepared containing the following components:

|  | Weight |
| --- | --- |
| Compound | 0.25 |
| Ethanol | 29.75 |
| Propellant 22 (Chlorodifluoromethane) | 70.00 |

The active compound is mixed with ethanol and the mixture added to a portion of the propellant 22, cooled to −30° C. and transferred to a filling device. The required amount is then placed in a stainless steel container and diluted with the remainder of the propellant. The valve units are then fitted to the container.

Formulation 4

Tablets each containing 60 mg of active ingredient are made up as follows:

| | |
|---|---|
| Compound | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 40–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules each containing 80 mg of medicament are made as follows:

| | |
|---|---|
| Compound | 80 mg |
| Starch | 59 mg |
| Microcrystalline cellulose | 59 mg |
| Silicone fluid | 2 mg |

The active ingredient, cellulose, starch and magnesium stearate are blended, passed through a No. 45 mesh U.S. sieve, and filled into hard gelatin capsules in 200 mg quantities.

Formulation 6

Suppositories each containing 225 mg of medicament are made as follows:

| | |
|---|---|
| Compound | 225 mg |
| Saturated fatty acid glycerides | 2 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

An intravenous formulation is prepared as follows:

| | |
|---|---|
| Compound | 100 mg |
| Isotonic saline | 1000 ml |

The solution of the above ingredients is administered intravenously at a rate of 1 ml/minute to a mammal in need of treatment.

It should be understood that in addition to the ingredients particularly mentioned above the formulations of this invention may include other agents conventional in the art having regard to the type of formulation in question.

The compounds of the present invention are also useful as laboratory tools for monitoring mutation of reverse transcriptase in vitro. For example, the compounds of Formula 1A stabilize the reverse transcriptase enzyme in vitro and allow for convenient cocrystallization. In its native state, reverse transcriptase is difficult to crystallize, a necessary initial step for X-ray crystallographic determination of the spatial structure of the enzyme. Repeated monitoring of the fine structure of this enzyme is necessary due to its rapid mutation in vivo, which in turn, leads to rapid viral resistance against conventional anti-HIV agents such as AZT and ddI. The rapid determination of the mutated structures is a key step to effective multiple therapy and slowing down the development of HIV resistant strains.

The limited success in growing reverse transcriptase crystals by conventional techniques has prompted a search for alternative methodologies and a certain amount of success has been accomplished with triple complexing of HIV reverse transcriptase with Fab fragments and DNA (A. Jacobo Molina et al. Proc. Nat'l. Acad, Sci. USA 90:6320 (1993)). However, the need for rapid and robust preparation of transcriptases for structural determination motivates the search for simpler and more effective cocrystallizing stabilizers.

Accordingly, a further aspect of the invention provides a method for stabilizing HIV-1 reverse transcriptase for crystallization comprising the steps or contacting a, preferably pure, solution of the transcriptase with a stabilizing amount of a compound of Formula 1A and cocrystallizing the resulting complex by conventional techniques such as the equilibrated hanging drop method or vapour diffusion method. Alternatively, ready seeded incipient crystals of transcriptase can be stabilized by conventional soak techniques to produce crystals having superior regularity and a longer working life.

Preferably, the compound of Formula 1A is present in a slight molar excess, for example a twofold molar excess, over the concentration of the transcriptase, however the concentration of the compound of the invention can vary within broad margins, for example between 1:10 (stabilizer:transcriptase) to 10:1.

Conventional crystallizing buffers, pH and osmolality regulators, etc. may be used in the mother liquor as are exemplified in A. J. McPherson et al., *Methods Biochem. Anal.* 23:249–345 (1979).

TEST II Co-crystallization of HIV Reverse Transcriptase

A crystallization buffer comprising 14% PEG, 0.1M Tris, pH 8.5, 0.36 mM HIV-1 reverse transcriptase (216 fragment)

and 0.4 mM of the compound N-(2-imidazo-4-yl)ethyl)-N'-(5-bromopyrid-2-yl)-urea (Example 36) is subject to hanging drop crystallization (T. Unge et al. Aids Res. & Human Retroviruses 6:1297 (1990). The resulting crystals are significantly larger (elongate prisms 2–4 mm long) and macroscopically more regular than those crystallized without the compound of the present invention. Preliminary results indicate that the useful exposure life is in excess of 10 hours, making the crystals amenable to X-ray crystallography to at least 3.5 Å, a threefold improvement.

Alternatively, co-crystallization can be effected by vapour diffusion, wherein a purified HIV-1 reverse transcriptase is prepared, e.a., in a crystallizing buffer consisting of 25 mM bis tris propane, pH 7, 50 mM ammonium sulphate, 0.1% (w/v) β-octyl glucoside, 5% (v/v) polyethylene glycol 8 000 and 0.1% sodium azide. A twofold molar excess of the compound of the invention over the concentration of transcriptase is added and allowed to complex. Crystals are crown by vapour diffusion against a solution which is double in the concentration of all components except the transcriptase. Preliminary results suggest that the resulting crystals can have dimensions in excess of 3.0×0.6×0.4 mm and a useful exposure lifetime of greater than 10 hours, enabling X-ray crystallography down to 3.5 Å. This method should be contrasted against crystals grown without co-crystallization which are irregular and only amenable to X-ray crystallography to 9.4 Å resolution (T. Unge et al. Aids Res. & Human Retroviruses 6:1297 (1990)).

The following examples further illustrate the compounds of the present invention and methods for the synthesis. The examples are not intended to be limiting to the scope of the invention in any respect and should not be so construed. In the descriptions of the preparations, the reference to example numbers are those found in Patent Application WO 93/03022 having a publication date of February 13, 1993, hereby incorporated by reference.

Preparation 1

(+,−)-N-(cis-2-(2,6-Difluorophenyl)-cyclopropyl)-N'-(5-ch loropyrid-2-yl)-thiourea The title compound was obtained starting from 2,6-difluorobenzaldehyde (purchased from Aldrich) which was converted to cis-2,6-difluorophenylcyclopropylamine according to the procedure in Example 375 and then condensed with the product from Example 393 according to the procedure in Example 370; $^1$H-NMR (250 MHz, DNSO-D6). d 1.3–1.4 (q, 1H) 1.6–1.7 (q, 1H) 2.3–2.4 (q, 1H), 3.8–3.9 (m, 1H) 7.2–7.3 (m,3H) 7.4–7.5 (m,1H) 7.7 (d, 1H) 7.8–7.9 (m, 1H) 10.7010.8 (s,1H) 11.0–11.1 (d, 1H).

Preparation 2

(+)-N-[cis-2-(2-chloro-3-ethoxy-6-fluorophenyl)-cyclopropyl]-N'-(5-chloro-2-pyridyl)thiourea The starting material (±)-cis-2-(2-chloro-3-ethoxy-6-fluorophenyl)cyclopropylamine was prepared from 2-chloro-4-fluorophenol in a manner analogous to Examples 362, 375 and 348. 5-Chloropyrid-2-ylisothiocyanate was prepared as in Example 374 and then condensed with (±)-cis-2-(2-chloro-3-ethoxy-6-fluorophenyl)cyclopropylamine in a manner analogous to Example 370 to give the titled product.

$^1$H-NMR (250 MHz, CDCl$_3$) d 11.25 (br s, 1H), 9.09 (br s, 1H), 7.72 (d, 1H), 7.49 (dd, 1H), 6.94 (t, 1H), 6.84 (dd, 1H), 6.74 (d, 1H) 4.12 (q, 2H), 3.67–3.57 9 (m, 1H), 2.23 (q, 1H), 1.78–1.68 (m, 1H), 1.55 (t, 3H), 1.44–1.36 (m, 1H). 13C-NMR (62.9 MHz, CDCL3) d 180.6, 156.6 (d), 114.2 (d), 112.8, 118.8 (d), 65.0, 32.7, 16.5, 15.7 (d), 14.7. Anal. calcd. for C$_{17}$H$_{16}$Cl$_2$FN$_3$OS: C, 51.01; H, 4.03; N, 10.5. Found C, 50.9; H, 3.9; N, 10.25.

Preparation 3

N-(2-(2–Chloro-3-ethoxy-6-fluorophenethyl)-N'-(2-(5-bromo)pyridyl)-thiourea

The starting material 2-chloro-3-ethoxy-6-fluorophenethylamine was prepared from 2-chloro-3-ethoxy-6-fluorobenzaldehyde in a manner analogous to Example 151 and 2-chloro-3-ethoxy-6-fluorobenzaldehyde was prepared from 2-chloro-4-fluorophenol in a manner analogous to Example 362. 2-Chloro-3-ethoxy-6-fluorophenethylamnine was condensed with the product of Example 392, using the procedure of Example 411 to give the titled product.

$^1$H-NMR (250 MHz, CDCl$_3$): d 11.30 (br s, 1H, NH), 9.35 (s, 1H, NH), 8.08 (d, 1H, pyridine), 7.69 (dd, 1H, pyridine) 6.93–6.76 (m, 3H, phenyl, pyridine), 4.11–4.00 (m, 4H CH$_2$—NH, OCH$_2$CH3), 3.24 (t, 2H, phenyl-CH$_2$), 1.46 (t, 3H, OCH$_2$CH3). $^{13}$C-NMR (250 MHz, CHCl$_3$): 179, 157, 153, 151, 150, 146, 140, 125, 124, 113, 112, 111, 65, 44, 25, 14. Anal. Calcd, for C$_{16}$H$_{16}$BrClFN$_3$OS: C, 44.4; H, 3.7; N, 9.7 Found: C, 44.7; H, 3.9; N, 9.3.

EXAMPLE 1

N-(2-Methoxyphenethyl)-N'-[2-(4-cyano)thiazolyl]urea

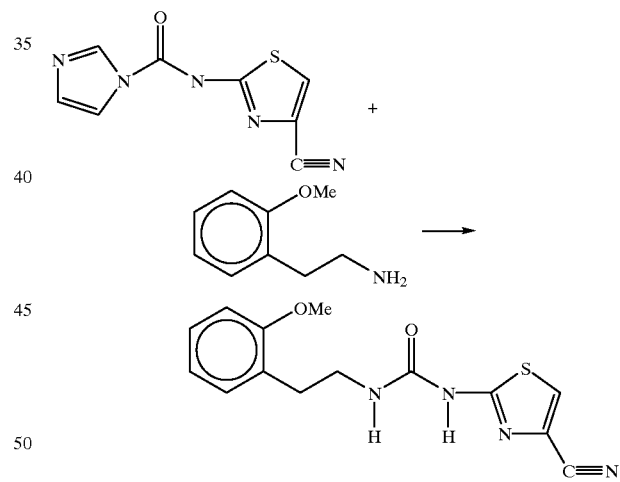

A solution of N-(imidazolyl)-2-amino-4-cyanothiazole (2.0 g, 9.12 mmol) and 2-methbxyphenethylamine (1.4 g, 9.12 mmol, 1.3 mL) in N,N-dimethylformamide (20 mL) was stirred at 90–95° C. After 2 h, the solution was cooled to room temperature, poured into ethyl acetate and washed with 0.1N hydrochloric acid (2×), water (2×), and brine. The organic layer was dried over magnesium sulfate, filtered and concentrated. The solid was recrystallized (50% ethyl acetate/hexames) providing 1.5 g (54%) of the titled product as white solid: mp 174° C.; IR (KBr, cm$^{-1}$) 3379, 3177, 3110, 3049, 2960, 2230, 1680, 1578, 1494, 1450, 1305, 1245, 1125; $^1$H NMR (300 MHZ, DMSO-d$_6$) 10.82 d(s,1H), 8.11 (s, 1 H), 7.19–7.08 (m, 2H), 6.92 (d, J=7 Hz, 1H), 6.83 (t, J=7 Hz, 1H), 6.52 (s, 1H), 3.73 (s, 3H), 3.32–3.27 (m, 2H), 2.69 (t, J=7.5 Hz, 2H); MS (FD) m/e 302 (M+); UV (EtOH) 269 nm (ε=9170), 243nm (ε=9394), 212 nm (ε=35263).

Anal. Calc'd. for $C_{14}H_{14}N_4O_2S$: C, 55.62; H, 4.67; N, 18.53. Found: C, 55.88; H, 4.76; N, 18.28.

EXAMPLE 2

N-(3-Methoxyphenethyl)-N'-[2-(4-ehyl)thiazole]urea

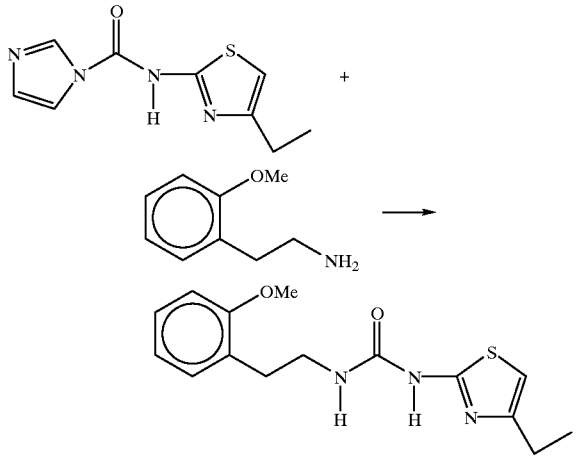

A solution of N-(imidazoyl)-2-amino-4- ethylthiazole (2.1 g, 9.4 mmol) and 3-methoxyphenethylamine (9.4 mmol, 1.4 mL) in N,N-dimethylformamide (20 mL) was stirred at 90–95° C. After 3 h, the solution was allowed to cool to room temperature, was poured into ethyl acetate and washed with 0.1N hydrochloric acid (2x), water (2x), and brine. The organic layer was dried over magnesium sulfate, filtered, and concentrated. The solid was recrystallized (50% ethyl acetate/hexanes) providing 1.5 g (52%) of the titled product as a white solid: mp 88–89° C.; IR (KBr, cm$^{-1}$) 3236, 3011, 2974, 1673, 1563, 1456, 1261, 1155, 1044; $^1$H NMR (300 MHZm CDCl$_3$) d 10.03 (br s, 1H), 7.23–7.17 (m, 1H), 6.83–6.29 (m, 3H), 6.77 (s, 1H), 3.76 (s, 3H), 3.62–3.52 (m, 2H), 2.85 (t, J=6.9 Hz, 2H), 2.59 (q, J=7.4 Hz, 2H), 1.17 (t, J=7.5 Hz, 3H); MS (FD) m/e 305 (M$_+$)' UV (EtOH) 266 nm (=11647), 202 nm (=28250).

Anal. Calc'd. for $C_{15}H_{19}N_3O_2S$:C, 58.99; H, 6.27; N, 13.76. Found: C, 58.93; H, 6.35; N, 13.79.

EXAMPLE 3

N-[3-Methoxyphenethyl]-N'-[2-N-methyl-4-ethyl-thiazolyl]urea

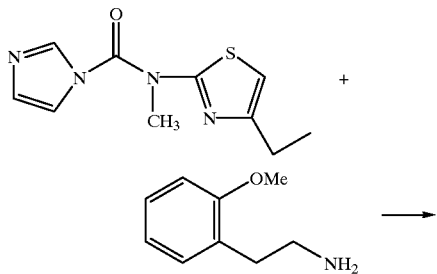

-continued

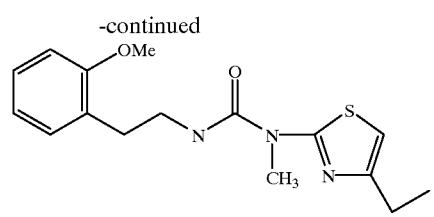

To a solution of 2-N-methyl-4-ethyl thiazole (9.2 g, 64.7 mmol) in 60 mL CH$_3$CN was added 1,1-carbonyldiimidazole (10.5 g, 64.7 mmol) and 40 mL CH$_3$CN. The solution was heated to 60–65_C for two days. The CH3CN was removed in vacuo leaving a brown oil that solidified upon standing. This solid (2.36 g, 10 mmol) was dissolved in DMF (40 mL), treated with 3-methoxyphenethylamine (1.5 9, 10 mmol, 1.46 mL), and stirred at 85° C. overnight. After cooling to room temperature, the reaction was poured into EtOAc and washed with 0.1N HCl (1x), H$_2$O (3x), and brine (1x). The organics were dried over Na$_2$SO$_4$, filtered and concentrated resulting in a yellow oil which solidified upon standing. The solid was purified by flash chromatography on silica gel (30% EtOAc/hexanes) to provide 1.05 g (33%) of the titled product as a yellow oil. IR (KBr, cm–1) 3010, 2975, 1673, 1557, 1512, 1339, 1318, 1260, 1105; $^1$H NMR (300 MHz, CDCl$_3$) d 9.69 (br s,1H), 7.25–7.18 (m, 1H), 6.85–6.73 (m,3H), 6.36 (s, 1H), 3.76 (s, 3H), 3.68–3.62 (m, 2H), 3.38(s, 3H), 2.87 (t, J=7 Hz, 2H), 2.54 (q, J=7.4 Hz, 2H), 1.15 (t, J=7.5 Hz, 3H); MS (FD) m/e 319(M+); UV (EtOH) 267 nm (ε=11892), 202 nm (ε=27796).

Anal. Calc'd. for $C_{16}H_{21}N_3O_2S$: C,60.16; H,6.65 N, 13.16. Found: C, 60.08; H, 6.53; N, 12.95.

EXAMPLE 4

(+,–)-N-(cis-2(2,6-Difluorophenyl)-cyclopropyl)-N'-(5-chloropyrid-2-yl)-urea

N-(cis-2-(2,6-Difluorophenyl)-cyclopropyl)-N'-(d-chloropyrid-2-yl)-thiourea ((20 mg, 0.06 mmol) was dissolved in dioxane (3 ml) and water (0.5 ml); N-bromosuccinimide (40 mg, 0.22 mmol) in dioxane (1 ml) was added at ambient temperature. After 10 minutes the solution was diluted with dichloromethane (10 ml) and washed with dilute aqueous sodium hydroxide solution (5 ml, 15%). The organic phase was dried with sodium sulphate, filtered and evaporated. The residue was purified by flash-chromatography on silica-gel by elution with a mixture of ethyl acetate and n-hexane (1:1) to yield the title compound as a white solid.

N-NMR (250 MHz, CHCl3-MeOD4). d 1.2–1.3 (m, 1H) 1.4–1.5 (m, 1H) 2.1–2.2 (q, 1H) 3.2–3.3 (m, 1H) 6.9–7.0 (m, 3H) 7.2–7.3 (m, 1H) 7.5–7.6 (m, 1H) 7.7–7.8)d, 1H).

EXAMPLE 5

N-(2-Chloro-3-ethoxy-6-fluorophenethyl)-N'-(5-bromopyrid-2-yl) -urea

The title compound was obtained from N-(2–Chloro-3-ethoxy-6-fluorophenethyl)-N'-(5-bromopyrid-2-yl)-thiourea according to the predure in Example 1.

$^1$H-NMR (250 MHz, DMSO-D6). d 1.4–1.5 (t, 3H) 3.0–3.1 (t, 2H) 3.5–3.6 (q, 2H) 4.1–4.3 (q, 2H) 7.0–7.3 (m, 2H) 7.5–7.6 (d, 1H) 7.7–7.8 (m, 1H) 7.9–8.0 (d, 1H) 8.4 (s, 1H) 9.2–9.3 (bs, 1H).

EXAMPLE 6

(+,−)-N-(cis-2-(2-chloro-3-ethoxy-6-fluorophenyl)-cyclopropyl)-N'-(5-chloropyrid-2-yl)-urea The title compound was obtained from N-(cis-2-(2-chloro-3-ethoxy-6-fluorophenyl)-cyclopropyl)-N'-(5-chloropyrid-2-yl)-thiourea according to the procedure in Example 1. 1H-NMR (250 MHz, DMSO-D6). d 1.1–1.2 (m, 1H) 1.4–1.5 (t, 3H) 1.6–1.7 (q, 1H) 2.1–2.2 (q, 1H) 3.3–3.4 (m, 1H) 4.2–4.4 (q, 2H) 7.2–7.3 (m, 2H) 7.4–7.5 (d, 1H) 7.7–7.8 (m, 1H) 7.9 (d, 1H) 8.0–8.1 (bs, 1H) 9.4 (bs, 1H).

EXAMPLE 7

N-(2-(2,6-difluoro)-phenethyl)-N'-(2-(5-chloro)-pyridinyl) urea

To a solution of 2.0 g (11 mmol) 2,6-Difluorocinnamic acid in ethanol (50 ml) was added about 100 mg of 5% of palladium on carbon. The reaction mixture was hydrogenated at atmospheric pressure until 250 ml of hydrogen was absorbed. The mixture was filtered and the solvent evaporated. Careful drying gave 1.87 g of a crude product which was used unpruified in the next step.

To solution of 1.87 g (10 mmol) of the above described crude product in dry toluene (20 ml) was added 1.53 ml (11 mmol) of triethylamine and 2.37 ml (11 mmol) of diphenylphosphoryl azide. The reaction mixture was stirred for 5 hours at room temperature, and then refluxed for 30 minutes. Thereafter, 1.54 g (12 mmol) of 2-amino-5-chloropyridine was added and the reaction mixture was stirred over night at +100° C. After cooling, EtOAc and brine were added. The organic phase was separated and dried over sodium sulfate. Evaporation of the solvent gave 3.75 g of crude product. 1.0 g of this material was purified on a silica gel column using ether 1 and hexanes 1 as the eluent. This procedure gave only a partial purification of the title compound and a final purification was performed on an alumina column which was eluted with THF 1 hexanes 2 followed by MeOH. 129 mg of the title compound was obtained.

Analysis: Calculated: C 53.95, H 3.9, N 13.5. Found: C 53.8, H 3.9, N 13.6 MP: 173.0–175.0° C. 1H-NMR (CDCl$_3$) d 3.00 (t, 2H), 3.62 (q, 2H), 6.80–6.90 (m, 3H), 7.10–7.23 (m, 1H), 7.53 (dd, 1H), 8.01 (d, 1H), 9.17 (broad t, 1H), 9.39 (broad s, 1H). 13C-NMR (DMSO-d$_6$) d 22.91, 38.63, 11;.35 (d, 2C), 112.91, 114.56 (t, 1C), 122.79, 128.85 (t, 1C), 138.03, 145.10, 152.11, 154.50, 161.34 (dd, 2C).

EXAMPLES 8 & 9

N-(2-Phenethyl)-N'-(5-bromopyrid-2-yl)-urea and N-(2-Phenethyl)-N'-(3,5-dibromopyrid-2-yl)-urea.

A solution of 10.0 g (37.3 mmole) of N-(imidazoyl)-2-amino-5-bromopyridine and 4.3 g (35.5 mmole) of phenethylamine in N, N-dimethylformamide (100 ml) was stirred at 90–95° C. for 2.5 hrs. The solution was cooled to room temperature, poured into ethyl acetate, and washed with water (5×), saturated sodium bicarbonate (3×), and brine (1×). The organic layer was dried over sodium sulfate, filtered, and concentrated. The solid was chromatographed over a flash silica gel column (2:1 hexanes/ethyl acetate) o provide isolation of two components. The first component was isolated as a white solid and was found to be the dibromopyridyl urea, 35 mg:

mp 145–147° C.; IR (KBr, cm$^{-1}$) 3400, 3300, 3000, 1683, 1474, 1364, 1285, 1230, 1035, 735, 700; $^1$H NMR (300 MHz, DMSO-d$_6$) δ0 8.45 (br.m. , 1H), 8.40 (d, 1H), 8.25 (d, 1H), 8.00 (br.s, 1H), 7.20–7.40 (m, 5H), 3.45 (q, 2H), 2.80 (t, 2H); MS (FD) m/e 399 (Mt). Anal. Calc'd. for C$_{14}$H$_{13}$Br$_2$N$_3$O H$_2$O; C, 41.65; H, 3.34; N, 10.41. Found: C, 41.62; H, 3.26; N, 10.32.

The second component was isolated as a white solid, filtered with the aid of ethyl ether, and was found to be the monobromopyridyl urea, 4.2 9 (37.5%): mp 164–167° C.; IR (KBr, cm$^{-1}$) 3275, 3200, 3000, 1686, 1540, 1363, 1302, 1230, 830, 701, 513; $^1$H NMR (300 MHz, DMSO-d$_6$) δ 9.30 (br.s., 1H), 8.20 (d, 1H), 7.90 (dd, 1H), 7.70 (br.t., 1H), 7.20–7.38 (m, 5H), 3.40 (q, 2H), 2.80 (t, 2H); MS (FD) m/e 319 (Mt). Anal. Calc'd. for C$_{14}$H$_{14}$BrN$_3$O: C, 52.52; H, 4.41; N, 13.12. Found: C, 52.78; H, 4.56; N, 13.18.

EXAMPLE 10

N-(3-Fluoropyrid-2-yl)eth-2yl-N'-(5-bromopyrid-2-yl)-urea.

A solution of 400 mg (1.13 mmole) of N-(3-fluoropyrid-2-yl)eth-2-yl-N'-(-bromopyrid- 2-yl)-thiourea (see Example 920 of WO93/03022) in 11.5 ml of glacial acetic acid was treated with 0.8 ml (7.83 mmole) of 30% hydrogen peroxide. After stirring 1.5 hrs at room temperature, the solution was concentrated and the residue was partitioned between ethyl acetate and saturated aqueous sodium bicarbonate (1×). The organic layer was back washed with brine (1×) and dried over sodium sulfate. Purification by flash silica gel chromatography (50% ethyl acetate/hexanes) gave 75 mg (19.6%) of the titled compound as a white solid: mp 151–154° C.; IR (KBr, cm$^1$) 3200, 3100, 3000, 1685, 1557, 1467, 1360, 1290, 1230, 839; $^1$H NMR (300 MHz, DMSO-d$_6$) δ 9.30 (br. s., 1H), 8.40 (d, 1H), 8.22 (d, 1h), 7.85 (dd, 1H), 7.79 (br.t., 1H), 7.70 (dz, 1H), 7.45 (d, 1H), 7.30–7.40 (m, 1H), 3.58 (q, 2H), 3.00 (t, 2); MS (FD) m/e 340 (Mt). Anal. Calc'd. for C$_{13}$H$_{12}$BrFN$_4$O: C, 46.04; H, 3.57; N, 16.52. Found: C, 46.25; H, 3.66; N, 16.54.

EXAMPLE 11

(+,−)-n-(cis-2-Phenylcyclopropyl)-N'-(5-Chloropyrid-2-yl)-urea

The titled compound was obtained from (+,−)-N-(cis-2-phenylcyclopropyl)-N'-(5-chloropyrid-2-yl)-thiourea (see Example 372 of WO 93/03022) according to the procedure in Example 10: mp 178–180° C.; IR (KBr, cm$^{-1}$) 3200, 3000, 1709, 1544, 1287, 698; $^1$H NMR (300 MHz, DMSO-d$_6$) δ 9.20 (br.s., 1h), 7.93 (d, 1H), 7.80 (dd, 1H), 7.60 (br.s., 1H), 7.18–7.38 (m, 6H), 3.00–3.10 (m, 1H), 2.20–2.30 (a, 1H9, 1.20–1.30 (q, 1H), 1.00–1.10 (q, 1H) MS (FD) m/e 287 (Mt). Anal. Calc'd. for C$_{15}$H$_{14}$ClN$_3$O: c, 62.61; H, 4.90; N, 14.60. Found: C, 62.35; H, 4.98; N, 14.56.

EXAMPLE 12

N-(2-Cyclohexen-1-yl) ethyl-N'-(5-bromopyrid-2-yl)-urea.

The titled compound was obtained from N-(2-cyclohexen-1-yl)ethyl-N'-(5-bromopyrid-2-yl)-thiourea (see Example 189 of WO 93/03022) according to the procedure in Example 10: mp 128–130° C.; IR (KBr, cm$^{-1}$) 3200, 2930, 1682, 1550, 1364, 1292, 1234, 836; $^1$H NMR (300 MHz, DMSO-d$_6$) δ 9.35 (s, 1H), 8.25 (d, 1H), 7.87 (dd, 1H), 7.60 (br.t., 1H9, 7.45 (d, 1H), 5.43 (br.s., 1H), 3.20 (q, 2H), 2.10 (t, 2H), 1.85–2.00 (m, 4H), 1.45–1.60 (m, 4H); MS (FD) m/e 325 (Mt). Anal. Calc'd. for C$_{14}$H$_{18}$BrN$_3$O: C, 51.86; H, 5.60; N, 12.96. Found: C, 52.07; H, 5.34; N, 12.68.

EXAMPLE 13

N-(2-(2,6-Difluoro-3-methoxyphenethyl)-N'-(5-bromopyrid-2-yl)-urea

The titled compound was obtained from N-(2-(2,6-difluoro-3-methoxyphenethyl)-N'-(5-bromopyrid-2-yl)-thiourea (see Example 411 of WO 93/03022) according to the procedure in Example 10: mp 198–200° C.; IR (KBr, cm$^{-1}$) 3200, 3000, 1686, 1492, 1364, 1223, 1077, 805; $^1$H NM. (300 MHz, DMSO-d$_6$) δ 9.30 (s, 1H), 8.20 (d, 1H), 7.85 (dd, 1H), 7.75 (br. t., 1H), 7.43 (d, 1H), 6.95–7.10 (m, 2H), 3.80 (s, 3H), 3.30 (q, 2H), 2.83 (t, 2H); MS (FD) m/e 385 (Mt). Anal. Calc'd. for C$_{15}$H$_{14}$BrF$_2$N$_3$O$_2$: C, 46.65; H, 3.65; N, 10.88. Found: C, 46.53; H., 3.85; N, 10.64.

EXAMPLE 14

N-(2-(2-Chloro-3-ethoxy-6-fluorophenethyl)-N'-(pyrazo-3-yl)-urea.

The starting material 2-chloro-3-ethoxy-6-fluorophenethylamine was prepared from 2-chloro-3-ethoxy-6-fluorobenzaldehyde as in Example 151 of WO 93/03022 and 2-chloro-3-ethoxy-6-fluorobenzaldehyde was prepared from 2-chloro-4-fluorophenol as in Example 362 of WO 93/03022. The titled compound was prepared from 2-chloro-3-ethoxy-6-fluoro-phenethylamine and N-(imidazoyl)-3-aminopyrazole according to Examples 8 & 9: mp 110–115° C.; IR (KBr, cm$^{-1}$) 3200, 3000, 1683, 1469, 1370, 1232, 1087, 829; $^1$H NMR (300 MHz, DMSO-d$_6$) δ 12.10 (br.s., 1H), 8.70 (s, 1H), 7.50 (br.s., 1H), 7.10–7.20 (m, 1H), 6.90–7.05 (m, 2H), 6.05 (br.s., 1H), 4.07 (q, 2H), 3.30 (q, 2H), 2.93 (br.t., 2H), 1.35 (t, 2H); MS (FD) m/e 326 (Mt). Anal. Calc'd. for C$_{14}$H$_{16}$ClFB$_4$O: C, 51.46; H, 4.94; N, 17.15. Found: C, 51.71; H, 4.81; N, 17.29.

EXAMPLE 15

N-(2-(2,6-Difluorophenethyl)-N'-(5-bromopyrid-2-yl)-urea

The titled compound was prepared from N-(2-2,6-difluorophenethyl)-N'-(5-bromopyrid-2-yl)-thiourea (see Example 340 of WO 93/03022) as in Example 10: mp 185–187° C.; IR (KBr, cm$^{-1}$) 3094, 1680, 1468, 1237, 1000, 830, 775; $^1$H NMR (300 MHz, DMSO-d$_6$) δ 9.30 (s, 1H), 8.20 (d, 1H), 7.86 (dd, 1H), 7.73 (br.t., 1H), 7.45 (d, 1H), 7.30–7.40 (m, 1H), 7.00–7.10 (t, 2H), 3.40 (q, 2H), 2.82 (t, 2H). MS (FD) m/e 355 (Mt). Anal. Calc'd. for C$_{14}$H$_{12}$BrF$_2$N$_3$O: C, 47.21; H, 3.40; N, 11.80. Found: C, 46.93; H, 3.61; N, 11.82.

EXAMPLE 16

N-(2-Phenethyl)-N'-(pyrimid-4-yl)-urea

The titled compound was prepared from N-(imidazoyl)-4-aminopyrimidine and phenethylamine according to the procedure in Examples 8 & 9: mp 162–164° C.; IR (KBr, cm$^{-1}$) 3200, 3113, 3045, 2944, 1680, 1589, 1306, 993, 761; $^1$H NMR (300 MHZ, DMSO-d$_6$) δ 9.60 (s, 1H), 8.65 (s, 1H), 8.45 (d, 1H), 7.75 (t, 1H), 7.50 (d, 1H), 7.20–7.40 (m, 5H), 3.40 (q, 2H), 2.78 (t, 1H); MS (FD) m/e 242 (Mt). Anal. Calc'd. for C$_{13}$H$_{14}$N$_4$O: C, 64.45; H, 5.82; N, 23.13. Found: C, 54.67; H, 6.06; N, 23.24.

EXAMPLE 17

N-(2-Phenethyl)-N'-(5-bromopyrimid-2-yl)-urea

The titled compound was prepared from N-(2-Phenethyl)-N'-(5-bromopyrimid-2-yl)-thiourea (see Example 222 of WO 93/03022) according to the procedure in Example 10: mp 205–208° C.; IR (KBr, cm$^{-1}$) 3309, 3045, 2972, 1692, 1564, 1504, 1415, 1285, 832; $^1$H NMR (300 MHz, DMSO-d$_6$) δ 10.00 (s, 1H), 8.70 (t, 1H), 8.65 (s, 2H), 7.20–7.40 (m, 5H), 3.45 (q, 2H), 2.80 (t, 2H); MS (FD) m/e 320 (Mt). Anal. Calc'd. for C$_{13}$H$_{13}$BrN$_4$O 0.5 H$_2$O: C, 47.30; H, 4.24; N, 16.97. Found: C, 47.10; H, 3.94; N, 16.94.

EXAMPLE 18

N-(2-Phenethyl)-N'-(6-chloropyridaz-3-yl)-urea

The titled compound was prepared from N-(2-Phenethyl)-N'-(6-chloropyridaz-3-yl)-thiourea (see Example 336 of WO 93/03022) as in Example 10: mp 222–225° C.; IR (K]r, cm$^{-1}$) 3341, 2980, 1709, 1554, 1420, 1251, 1140, 696; $^1$H NMR (300 MHz, DMSO-d$_6$) δ 9.80 (s, 1H), 8.05 (d, 1H), 7.75 (d, 1H), 7.10–7.40 (m, 6H), 3.40 (q, 2H), 2.80 (t, 2H); MS (FD) m/e 276 (Mt). Anal. Calc'd. for C$_{13}$H$_{13}$ClN$_4$O 0.25 H$_2$O: C, 55.55; H, 4.80; N, 19.93. Found: C, 55.36; H, 4.67; N, 19.95.

EXAMPLE 19

N-(2-Phenethyl)-N'-(4-bromopyrazo-3-yl)-urea

The titled compound was prepared from N-(imidazoyl)-2-phenethylamine and 3-amino-4-bromo-pyrazole as 4n Examples 8 & 9: mp 132–135° C.; IR(KBr, cm$^{-1}$) 3351, 3271, 1712, 1530, 1386, 1238, 1078, 700; $^1$H NMR (300 MHz, DMSO-d$_6$) δ 8.17 (s, 1H), 7.80 (t, 1H), 7.20–7.30 (m, 5H), 5.40 (s, 2H), 3.45 (q, 2H), 2.83 (t, 2H); MS (FD) m/e 308 (Mt). Anal. Calc'd. for C$_{12}$H$_{13}$BrN$_4$O: C, 46.62; H, 4.24; N, i8.12. Found: C, 46.65; H, 4.14; N, 17.93.

EXAMPLE 20

N[(4-Ethoxy-3-fluoropyrid-2-yl)eth-2-yl]-N'-(5-bromopyrid-2-yl)-urea

20a)

N-[(3-Fluoropyrid-2-yl)eth-2-yl]-2,5-dimethylpyrrole

A mixture of 3.6 g (25.70 mmole) of 2-(2-aminoethyl)-3-fluoropyridine, 3.0 g(26.3 mmole) of 2,5-hexanedione, 0.4 ml of glacial acetic acid, and 100 ml of toluene was refluxed with a Dean-Stark trap for 3 hrs. The mixture was cooled to room temperature and extracted with saturated aqueous sodium bicarbonate (1×) and brine (1×). The organic layer was dried over sodium sulfate, filtered, and concentrated to a solid. Recrystallization from ethyl ether/hexanes provided the titled compound as an off-white solid; 5.0 g (90%): mp 82–84° C.; IR (KBr, cm$^{-1}$) 3075, 2931, 1448, 1407, 1112, 755; $^1$H NMR (300 MHz, DMSO-d$_6$) δ 8.40 (d, 1H), 7.66 (dt, 1H) 7.38 (m, 1H), 5.60 (s, 2H), 4.05 (t, 2H), 3.05 (dt, 2H), 2.10 (s, 6H); MS (FD) m/e 218 (Mt). Anal. Calc'd. for C$_{13}$H$_{15}$FN$_2$: C, 71.53; H, 6.93; N, 12.83. Found: C, 71.73; H, 7.05; N, 13.04.

20b)

N-[(3-Fluoro-4-iodopyrid-2-yl)eth-2-yl]-2,5-dimethyl-pyrrole

A dry 250 ml 3-neck roundbottom flask equipped with a thermometer, rubber septum, magnetic stirrer, and nitrogen inlet was charged with 30 ml of anhydrous tetrahydrofuran and 2.1 ml (14.67 mmole) of dry diisopropylamine. The stirring solution was cooled to −78° C. After which 9.5 ml (15.11 mmole) of 1,6 n-butyllithium in hexanes was added over 10 minutes by syringe. The solution was stirred 30 minutes longer and 3.2 g (14.67 mmole) of N-[(3-Fluoropyrid-2-yl)eth-2-yl]-2,5-dimethylpyrrole in 30 ml of dry tetrahydrofuran was added dropwise via syringe over 30 minutes, keeping the internal temperature below −65° C. After stirring 30 minutes longer, a solution of 4.0 g (15.80 mmole) of iodine in 30 ml of dry tetrahydrofuran was added by canula over 10 minutes. The mixture was warmed to room temperature (a color change, quenching, occurred at −30° C.) and stirred overnight under nitrogen. The solution was diluted to 200 ml with ethyl ether, extracted with aqueous saturated sodium bicarbonate (IX), brine (IX), and dried over sodium sulfate. Filtration and concentration gave a dark solid which was purified by flash silica gel chromatography (20% ethyl acetate in hexanes) to give the titled compound as a white solid, 3,9 g (77%): mp 156–158° C.; IR (KBr, cm$^{-1}$) 3000, 2950, 1574, 1408, 752; $^1$H NMR (300 MHz, DMSO-d$_6$) δ 8.05 (d, 1H) 7.85 (t, 1H), 5.60 (s, 2H), 4.05 (t, 2H), 3.00 (dt, 2H), 2.10 (s, 6H); MS (FD) m/e 344 (Mt). Anal. Calc'd. for C$_{13}$H$_{14}$FIN$_2$: C, 45.37; H, 4.10; N, 8.14. Found: C, 45.07; H, 4.03; N, 8.06.

20c)

N[(4-Ethoxy-3-fluoropyrid-2-yl)eth-2-yl]-2,5-dimethyl-pyrrole

A solution of sodium ethoxide was initially prepared by dissolving 2.0 g (87 mmole) of sodium metal in 300 ml of anhydrous absolute ethanol. To the stirring solution thus prepared was added 3.5 g (10.2 mmole) of N-[(3-Fluoro-4-iodopyrid-2-yl)eh-2-yl]-2,5-dimethyl-pyrrole and the mixture was refluxed under nitrogen for 4 days. The solution was cooled, diluted to 1 liter with water, and extracted with ethyl acetate (2×). The organic layer was dried over sodium sulfate, filtered, and concentrated to a resin. Chromatography over flash silica gel (30% ethyl acetate in hexanes) gave initially 320 mg (8.5%) of N-[(4-Iodo-3-ethoxypyrid-2-yl)-eth-2-yl]-2,5-dimethylpyrrole: $^1$H NMR (300 MHz, DMSC-d$_6$) δ 7.95 (d, 1H), 7.62 (d, 1H), 5 80 (s, 2H), 4.10 (t, 2H), 4.00 (q, 2H), 3.15 (t, 2H), 2.20 (s, 6H), 1.45 (t, 3H), MS (FD) m/e 370 (Mt). Further elution provided the titled compound, 1.7 g (64%): IR (KBr, cm$^{-1}$) 2991, 1608, 1495, 1309, 1075; $^1$H NMR (300 MHz, DMSO-d$_6$) δ 8.22 (d, 1H), 7.15 (t, 1H), 5.60 (s, 2H), 4.20 (q, 2H), 4.10 (t, 2H), 2.98 (dt, 2H), 2.10 (s, 6H), 1.38 (t, 3H): MS (FD) m/e 262 (Mt). Anal. Calc'd. for C$_{15}$H$_{19}$FN$_2$O 0.25 H$_2$O: C, 67.55; H, 7.31; N, 10.50. Found: C, 67.56; H, 7.35; N, 10.46.

20d)

2-(2-Aminoethyl)-4-ethoxy-3-fluoropyridine

A mixture of 825 mg (3.15 mmole) of N-[(4-Ethoxy-3-fluoropyrid-2-yl)eth-2-yl]-2,5-dimethylpyrrole, 1.4 g (20.1 mmole) of hydroxylamine hydrochloride, 700 mg (12.5 mmole) of potassium hydroxide, 20 ml of ethanol, and 8 ml of water was refluxed for 3 days under nitrogen. The solution was cooled to room temperature, concentrated, and partitioned between 50 ml of 2N hydrochloric acid and ethyl acetate (3×). The aqueous layer was basified with 5N sodium hydroxide, extracted with ethyl acetate (3×), dried over sodium sulfate, and concentrated. The resulting red oil was found to be the titled compound with a small amount of 2,5-hexanedione dioxime also present. The oil was used as such for reaction without further purification: IR (KBr, cm$^{-1}$) 2989, 1609, 1495, 1306, 1075; $^1$H NMR (300 MHz, DMSO-d$_6$) δ 8.18 (d, 1$^1$H), 7.05 (t, 1H), 4.20 (q, 2H), 2.60–3.00 (m, 6H), 1.38 (t, 3H); MS (FD) m/e 185 (Mt).

20e)

N-[(4-Ethoxy-3-fluoropyrid-2-yl)eth-2-yl]-N'-(5-bromopyrid-2-yl)-urea

The titled compound was prepared from N-(imidazoyl)-2-amino-5-bromopyridine and 2-(2-aminoethyl)-4-ethoxy-3-fluoropyridine as in Examples 8 & 9: mp 143–145° C.; IR (KBr, cm$^{-1}$) 3221, 2989, 1684, 1475, 1306; $^1$H NMR (300 MHz, DMSO-d$_6$) δ 9.30 (s, 1H), 8.10 (m, 2H), 7.90 (dd, 1H), 7.78 (br.t., 1H), 7.42 (d, 1H), 7.15 (t, 1H), 4.20 (q, 2H), 3.55 (q, 2H), 2.92 (dt, 2H,), 1.35 (t, 3H): MS (FD) m/e 382 (Mt). Anal. Calc'd. for C$_{15}$H$_{16}$BrFN$_4$O$_2$: C, 47.01; H, 4.21; N, 14.62. Found: C, 46.80; H, 4.21; N, 14.41.

EXAMPLE 21

(+,−)-N-(cis-2-(3-Nitrophenyl)-cyclopropyl)-N'-(5-chloropyrid-2-yl)-urea

3-Nitrostyrene (Aldrich) was converted to cis-2-(3-nitrophenyl)cyclopropanecarboxylic acid by the method described in Example 348 (patent application WO 93/03022), with the exception that the separation of cis-isomer was performed at the ethyl ester stage using a silica gel column eluted with hexanes 9 and ethyl acetate 1. The acid was then converted to an isocyanate as described in *J. Org. Chem.*, p. 3511 (1961). The title compound was obtained by reacting the above described isocyanate with 2-amino-5-chloropyridine as described in Example 7. Analysis: Calculated: C 54.1, H 3.9, N 16.8. Found: C 53.7, H 3.9, N 16.5. Mp: 201.0–202.0° C. $^1$H-NMR (250 MHz, CDCl$_3$) 6 1.20–1.29 (m, 1H), 1.49–1.61 (m, 1H), 2.44 (q, 1H), 3.25–3.33 (m, 1H), 6.69 (d, 1H), 7.38–7.5 (m, 2H), 7.61 (d, 1H), 7.77 (d, 1H), 8.03–8.08 (m, 2H), 8.47 (broad s, 1H), 8.90 (broad s, 1H).

EXAMPLE 22

(+,−)-N-(cis-2-(3-Ethynylphenyl)-cyclopropyl)-N'-(5-chloropyrid-2-yl)-urea

3-Bromostyrene (Aldrich) was converted to the ethyl ester of cis-2-(3-bromophenyl)cyclopropanecarboxylic acid in a process similar to the one described in Example 21. The ethyl ester was then reacted with TMS-acetylene in the presence of Pd(II) as described in *Tetrahedron Letters* p.6403–6405 (1993). After deprotection (LiOH), the resulting cis-2-(3-ethynylphenyl)-cyclopropanecarboxylic acid was transformed to the title compound according to the procedure in Example 7.

Analysis: Calculated: C 65.5, H 4.5, N 13.6. Found: C 65.6, H 4.4, N 12.9. Mp: 148.5–149.5° C. $^1$H-NMR (250 MHz, CDCl$_3$) δ 1.07–1.14 (m, 1H), 1.38–1.44 (m, 1H), 2.27–2.38 (m, 1H), 3.04 (s, 1H), 3.23–3.31 (m, 1H), 6.77 (d, 1H), 7.20–7.50 (m, 5H), 7.75 (d, 1H), 8.90 (broad s, 1H), 9.20 (broad s, 1H).

EXAMPLE 23

(+,−)-N-(cis-2-(3-Acetylphenyl)-cyclopropyl)-N'-(5-chloropyrid-2-yl)-urea

A solution of (+,−)-N-(cis-2-(3-Ethynylphenyl)-cyclopropyl)-N'-(5-chloropyrid-2-yl)-urea of Example 22(130 mg, 0.42 mmole), H$_2$SO$_4$ (10 drops), H$_2$O (10 drops) and Hg(OAc)$_2$ (100 mg) in acetic acid (4 mL) was stirred at room temperature for 30 min. The reaction mixture was then poured into an ethyl acetate and saturated $K_2CO_3$ solution. The organic layer was dried ($MgSO_4$) and the solvent was evaporated to give a residue which was purified on silica gel using 1:1 acetone: and hexanes as the eluent providing 43 mg of the title compound.

Analysis: Calculated: C 61.9, H 4.9, N 12.75. Found: C 61.5, H 4.7, N 12.1. Mp: 144.0–145.0° C. $^1$H-NMR (250 MHz, $CDCl_3$) δ 1.15–1.24 (m, 1H), 1.40–1.51 (m, 1H), 2.34–2.47 (m, 1H), 2.55 (s, 3H), 3.23–3.34 (m, 1H), 6.85 (d, 1H), 7.35–7.52 (m, 3H), 7.62 (d, 1H), 7.77–7.90 (m, 2H), 8.90 (broad s, 1H), 9.45 (broad s, 1H).

EXAMPLE 24

(+,-)-N-(cis-2-(3-Aminophenyl)-cyclopropyl)-N'-(5-chloropyrid-2-yl)-urea

Cis-2-(3-nitrophenyl)cyclopropanecarboxylic acid (355 mg, 1.7 mmole), described in Example 21, was dissolved in 50 ml ethanol and 20 mg of $PtO_2$ was added. Hydrogenation at atmospheric pressure for 1 hr. followed by filtration and evaporation of the solvent afforded 288 mg of cis-2-(3-aminophenyl)cyclopropanecarboxylic acid. 177 mg (1 mmole) of cis-2-(3-aminophenyl)cyclo-propanecarboxylic acid was dissolved in water (1 mL), t-BuOH (1 mL) and 2M NaOH (0.5 mL, 1 mmole). 250 µL (1.1 mmole) of di-tert-butyl dicarbonate was then added and the reaction mixture was stirred at room temperature overnight. The reaction mixture was poured into ice and water and acidified with dilute $H_2SO_4$ and extracted with dichloromethane affording 264 mg of pure BOC protected cis-2-(3-aminophenyl)-cyclopropanecarboxylic acid. This acid was transformed to BOC protected title compound according to the Procedure in Example 7. Finally, deprotection with THF 1 and 6M HCl 1 gave the title product. Analysis: Calculated: C 59.5, H. 5.0, N 18.5.

Found: C 59.5, H 4.9, N 17.2. Mp: 177.5–178.2° C. $^1$H-NMR (250 MHz, $CDCl_3$) δ 1.00–1.07 (m, 1H), 1.23–1.37 (m, 1H) 2.24–2.33 (m, 1H), 3.15–3.25 (m, 1H), 3.65 (broad s, 2H), 6.59–6.70 (m, 4H), 6.77 (broad s, 1H), 7.11 (t, 1H), 7.45 (dd, 1H), 7.72 (s, 1H), 8.81 (broad s, 1H).

EXAMPLE 25

N-(3-Methoxyhenethyl)-N'-(5-chloropyrid-2-yl)-urea

Following the condensation procedure described in Example 2 and using N-(imidazoyl)-2-amino-5-chloropyridine inszead of N-(imidazcyl)-2-amino-4-ethylthiazole, resulted in the titled product. $^1$H-NMR (250 MHz, $CDCl_3$) δ 2.89 (t, 2H), 3.65 (q, 2H), 3.79 (s, 3H), 6.78–6.87 (m, 4H), 7.25–7.28 (m, 1H), 7.52 (dd, 1H), 7.99 (d, 1H), 9.05 (broad s, 1H), 9.12 (broad t, 1H).

EXAMPLE 26

(+,-)-N-(cis-2-(2,6-Difluorophenyl)-cyclopropyl)-N'-(5-cyanopyrid-2-yl)-urea 2,6-Difluorobenzaldehyde (Aldrich) was converted to cis-2-(2,6-difluorophenyl)cyclopropylamine according to Example 375 (Patent Application WO 93/03022) and then converted to an isothiocyanate according to Example 374 (Patent Application WO 93/03022). This isothiocyanate was reacted with the anion of 2-amino-5-cyanopyridine to give (+,-)-N-(cis-2-(2,6-Difluorophenyl) cyclopropyl)-N'-(5-cyancpyrid-2-yl)-thiourea. 6 mg of this compound was reacted with NBS as described in Example 4 and a final purification on alumina, resulted in 0.7 mg of the title product. Rf : 0.30 Silica gel eluent: diethyl ether.

EXAMPLE 27

(1R,2S)-N-(cis-2-(2,6-Difluorophenyl)-cyclopropyl)-N'-(5-bromopyrid-2-yl)-urea (1R,2S)-N-(cis-2-(2,6-Difluorophenyl)-cyclopropyl)-N'-(5-bromopyrid-2-yl)-hiourea was prepared according to Examples 422, 424 and 427 (Patent Application WO 93/03022) starting with (+,-)-cis-2-(2,6-difluorophenyl)-cyclopropylamine instead of (+,-)-cis-cyclopropylamine. $[α]D^{22}$ of (1R,2S)-N-(cis-2-(2,6-Difluorophenyl)-cyclopropyl)-N'-(5-bromcpyrid-2-yl)-thiourea was −47.8° (c=0.54, EtOAc). Application of the method described in Example 4 using (1R,2S)-N-(cls-2-(2,6-Difluorophenyl)-cyclopropyl)-N'-(5-bromopyrid-2-yl)-thiourea afforded the title compound. $^1$H-NMR (250 MHz, acetone-$d_6$) δ 1.20–1.30 (m, 1H), 1.40–1.50 (m, 1H), 2.00–2.20 (m, partly hidden by the signals from the solvent, 1H), 3.25–3.35 (m, 1H), 6.95–7.10 (m, 2H), 7.22 (d, 1H), 7.30–7.50 (m, 1H), 7.79 (dd, 1H), 7.95 (d, 1H), 8.28 broad s, 1H), 8.60 (broad s, 1H).

EXAMPLE 28

(1R,2S)-N-(cis-2-(2-chloro-3-ethoxy-6-fluorophenyl)-cyclopropyl)-N'-(5-chloropyrid-2-yv)-urea (1R,2s)-cis-2-(2-chloro-3-ethoxy-6-fluorophenyl) cyclopropylcarboxylic acid was prepared from 2-chloro-3-ethoxy-6-fluorostyrene, using an asymmetric cyclopropanation reaction catalyzed by Cu(I)triflate and a chiral ligand as described by Evans et al. in *J. Am. Chem. Soc.* 1991, 113, 726–728. This acid was transformed to the title compound according to the procedure described in Example 7. Analysis: Calculated: C 53.1, H 4.2, N 10.9. Found: C 53.3, H 4.3, N 11.0.

Mp: 168.5–169.0° C. $[α]D^{22}$−80.00 (c=0.50, $CHCl_3$). $^1$H-NMR (250 MHz, $CDCl_3$) 6 1.27–1.35 (m, 1H), 1.53 (t, 3H), 1.55–1.67 (m, !H), 2.01–2.14 (m, 1H), 3.25–3.29 (m, 1H), 4.09 (q, 2H), 6.72–6.94 (m, 3H), 7.45 (dd, 1H), 7.80 (d, 1H), 8.86 (broad s, 1H), 9.25 (broad s, 1H).

EXAMPLE 29

N-(2-phenethyl)-N'-(thiozol-2-yl)-urea 3.38 g phenyl propanoic acid chloride (mw 169, 20 mmole) was dissolved in 20 ml toluene. A saturated aqueous solution containing $LiN_3$ 1.25 g (mw 48, 25 mmole) was added under vigorous stirring at 0° C. The mixture was heated to 20° C. and stirred for 1 hr. The aqueous phase was separated by means of a silanized filter paper. The organic phase was dried with $Na_2SO_4$ and the solvent removed. The residue was redissolved in 20 ml toluene, and heated to 90° C. for 15 min. The solvent was removed and the raw isocyanate dissolved in 10 ml DMF together with 2 g 2-aminothiazole (mw 100, 20 mmole). This mixture was stirred at 110° C. for 17 hrs. The solvent was removed, and the raw product dissolved in 200 ml ethyl acetate, washed twice with 50 ml 1M hydrochloric acid, and once with 50 ml water. Crystallisation from ethanol gave fine needles, 2.21 g Mu 162° C. $^1$H-NMR (250 MHz, DMSO-$d_6$): 2.86 (t, 2H), 3.00 (t, 2H), 7.25–7.43 (m, 6H), 7.57 (d, 1H).

EXAMPLE 30

N-(2-ethoxy-5,6-difluorophenethyl)-N'-(5-bromopyrid-2-yl)-urea 32.5 g 3,4-difluorophenol (Aldrich) was dissolved in 600 ml acetone. 50 g $K_2CO_3$ and 45 g iodoethane was added, and the mixture stirred at 50° C. overnight. The product 1-ethoxy-3,4-difluorobenzene was purified by distillation, and was then transformed to 2-ethoxy-5,6-difluorobenzaldehyde according to the procedure in Example 362 of WO 93/03022.

The methods described in Example 151 of WO 93/03022 was then used to transform this compound to 2-ethoxy-5,6-difluoro-phenethylamine. The method described in Example 411 of WO 93/03022 was then used to prepare N-(2-ethoxy-5,6-difluorophenethyl)-N'-(5-bromopyrid-2-yl)-thiourea. This product was then oxidised with NBS as Example 4 to provide N-(2-ethoxy-5,6-difluorophenethyl)-N'-(5-bromopyrid-2-yl)-urea. $^1$H-NMR (250 MHz, CDCl$_3$): 1.4 (t, 3H), 3.0 (q, 2H), 3.95 (q, 2H), 6.5 (m, 1H), 6.8 (d, 1H), 6.95 (dd, 1H), 7.68 (dd, 1H), 8.90 (d, 1H) 8.9 (s, 1H), 9.0 (s, 1H).

EXAMPLES 31 & 32

N-(cis-2-(2-ethoxy-5,6-difluorophenyl)-cyclopropyl)-N'-(5-bromopyrid-2-yl)-urea

N-(trans-2-(2-ethoxy-5,6-difluorophenyl)-cyclopropyl)-N'-(5-bromopyrid-2-yl)-urea The 2-ethoxy-5,6-difluorobenzaldehyde prepared as described in Example 30 was converted to a cis/trans mixture of 2-(2-ethoxy-5,6-difluorophenyl)-cyclopropylamines according to the methods described in Examples 375 and 348 of WO 93/03022. This product was then condensed with the product from Example 392 according to the procedure in Example 411 of WO 93/03022 and was then oxidized with NBS as in Example 4 to provide a mixture of the cis and trans N-(2-(2-ethoxy-5,6-difluorophenyl)-cyclopropyl)-N'-(5-bromopyrid-2-yl)-ureas. The two products were separated on a silica-gel column eluted with mixtures of dichloroethane and ethylacetate: N-(cis-2-(2-ethoxy-5,6-difluorophenyl)-cyclopropyl)-N'-(5-bromopyrid-2-yl)-urea: $^1$H-NMR (250 MHz, CDCl$_3$) 1.2–1.3 (m, 1H), 1.35 (t, 3H), 1.5 (m, 1H), 2.0–2.1 (m,1H), 3.2–3.3 (m, 1H), 3.95 (q, 2H), 6.5–6.6 (m,1H), 6.7–6.8 (m, 1H), 7.0 (dd, 1H), 7.55 (dd, 1H), 7.8 (s, 1H), 8.7 (s, 1H), 9.2 (s, 1H).

N-(trans-2-(2-ethoxy-5,6-difluoro-phenyl)-cyclopropyl)-N'-(5-bromopyrid-2-yl)-urea: $^1$H-NMR (250 MHz, CDCl$_3$): 1.2–1.3 (m, 1H), 1.4 (t, 3H), 1.6–1.7 (m, 1H), 2.1–2.2 (m, 1H), 3.2–3.3 (m, 1H), 4.05 (q, 2H), 6.5 (m, 1H), 6.7–6.8 (m, 1H), 7.6–7.8 (m, 2H), 8.2–8.4 (m, 1H), 9.0 (s, 1H), 9.3 (s, 1H)

EXAMPLES 33 & 34

N-(cis-2-(2-chloro-6-fluorophenyl)-cyclopropyl)-N'-(5-cyanopyrid-2-yl)-urea

N-(cis-2-(2-chloro-6-fluorophenyl)-cyclopropyl)-N'-(5-chloropyrid-2-yl)-urea 2-chloro-6-fluorobenzaldehyde (Aldrich), was converted to 2-chloro-6-fluorostyrene according to the method described in Example 377 of WO 93/03022 and then to cis-2-(2-chloro-6-fluorophenyl) cyclopropylisocyanate analogously to the method described in Example 348 of WO 93/03022. This compound was then condensed with 2-amino-5-cyanopyridine of Example 41 in a manner analogous to the method in Example 7 to provide N-(cis-2-(2-chloro-6-fluorophenyl)-cyclopropyl)-N'-(5-cyanopyrid-2-yl)-urea: Mp 189° C. $^1$H -NMR (250 MHz, DMSO-d$_6$): 1.2 (m, 1$^1$H), 1.45–1.55 (m, 1H), 2.2–2.3 (m, 1H), 3.3–3.4 (m, 1H), 7.35–7.6 (m, 4lz), 7.9–8.1 (m, 2H), 9.5 (s, 1).

2-(2-chloro-6-fluorophenyl)cyclopropylisocyanaze prepared as described above was condensed with 2-amino-5-chloropyridine according to the method used in Example 7 to provide N-(cis-2-(2-chloro-6-fluorophenyl)-cyclopropyl)-N'-(5-chloropyrid-2-yl)-urea: $^1$H-NMR (250 MHz, CDCl$_3$): 1.3–1.4 (m, 1H), 1.5–1.6 (m, 1H), 2.0–2.1 (m, 1H), 3.3–3.4 (m, 1H), 6.7–6.8 (m, 1H), 6.9–7.0 (m, 1H), 7.15–7.30 (m, 2H), 7.4–7.5 (m, 1H), 7.7 (m, 1H), 8.8 (s, !H), 9.1 (s, 1H).

EXAMPLE 35

(+,-)-N-(cis-2(2–Chloro-3-ethoxy-6-fluorophenyl) cyclopropyl-N'-(5-acetonyrid-2-yl)-urea To a mixture of acetic acid (2 ml), H$_2$SO$_4$ (5 drops) and H$_2$O (2 drops) was added (+,-)-N-(cis-2(2-Chloro-3-ethoxy-6-fluorophenyl)cyclopropyl-N'-(5-ethynpyrid-2-yl)-urea (40 mg, 0.11 mmole) from Example 62. This mixture was stirred well and mercuric acetate (50 mg, 0.16 mmole) added. After 1 hour, the mixture was partitioned between aqueous KHCO$_3$ and ethyl acetate. The organic layer was dried, concentrated and the residue purified by silica gel chromatography (toluene-acetone, 3:1) to yield the title compound (11.2 mg, 27%). $^1$H-NMR (250 MHz, CDCl$_3$) d 1,35 (m, 1H), 1.50 (t, 3H), 1.64 (m, 1H), 2.13 (dd, 1H), 2.53 (s, 3H), 3.32 (m, 1H), 4.12 (dq, 25 2H), 6.81–6.96 (m, 3H), 8.03 (dd, 1H), 9.41 (broad s, NH), 9.62 (broad s, NH). $^{13}$C-NMR (250 MHz, CDCl$_3$) selected signals d 14 81, 15.12, 15.80, 26.21, 65.57, 111.46, 126.03, 137.62, 147.73, 156.88, 156.73, 195.29.

EXAMPLE 36

N-(2-(Imidazo-4-yl)ethyl)-N'-(5-bromopyrid-2-yl)-urea

To a stirred solution of N-(2-(imidazo-4-yl)ethyl)-N'-(5-bromopyrid-2-yl)-thiourea prepared analogously to Example 328 of WO 93/03022 (50 mg, 0.15 mmole) in dioxane (7 ml) and N$_2$O (1 ml) was added N-bromosuccinimide (100 mg, 0.56 mmole). After 1 hr. the mixture was partitioned between aqueous NaHCO$_3$ and CH$_2$Cl$_2$. The organic layer was dried, concentrated and crystallised from ethanol to give the title compound (22 mg, 46%). MP: 204° C. $^1$H-NMR (250 MHz, CDCl$_3$) d 3.05 (m, 2H), 3.60 (m, 2H), 6.87 (d, 1H), 7.03 (dd, 1H), 7.27 (s, 1H), 7.71 (dd, 1H), 8.29 (d, 1H), 8.39 (d, 1H), 10.48 (broad s, 1H). $^{13}$C-NMR (250 MHz, CDCl$_3$) d 20.32, 38.82, 112.99, 123.18, 125.70, 134.64, 140.44, 145.94, 146.59, 159.85.

EXAMPLE 37

N-[2-(2,6-Difluoro-3-dimethylamino)phenethyl]-N'-[2-(5-chloro)myridyl]-urea

A mixture of 2,4-difluoroaniline (5.0 g, 38.7 mmole) and trimethylphosphate (3.6 a, 25.8 mmole) was refluxed at 180° C. for 2 hrs. After the mixture was cooled to 50° C. NaOH (3.2 g, 80.6 mmole) in 12 ml of H$_2$O was added to it and it was refluxed again for 1 hr. The mixture was cooled, H$_2$O was added to it and it was extracted with diethyl ether, dried over Na$_2$SO$_4$ and evaporated. The crude material was filtrated through Al$_2$O$_3$ column by using diethyl ether as eluent to give 4.4 g (73%) of 1-dimethylamino-2,4-difluorobenzene. This compound was converted to 2,6-difluoro-3-dimethylamino-phenethylamine according to the procedure in Examples 362 and 151 of WO 93/03022, and condensed with the product from Example 392 according to the procedure in Example 411 to give N-[2-(2,6-difluoro-3-dimethylamino)phenethyl]-N'[2-(5-chloro)pyridyl]-thiourea. This compound was converted to the titled compound according to the procedure fin the present Example 4. Mp 135° C. $^1$H NMR 250 MHz, CDCl$_3$) δ 9.64 (s, 1H), 9.21 (br s, 1H), 8.13 (d, 1H), 7.65 (dd, 1H), 6.86–6.75 (m, 3H), 3.63 (q, 2H), 3.01 (t, 21H), 2.75 (s, 6H).

EXAMPLE 38

N-(2-Phenethyl)-N'-[2-(5-chloro)pyridazyl]-urea

NaH, 80 a (0.12 g, 3.86 mmole) was added to a solution of 3-amino-6-chloropyridazine (0.50 g, 3.86 mmole) in THF (40 mL) at 0° C. under nitrogen. The mixture was stirred for 15 min and N,N'-carbonyldiimidazole (0.63 g, 3.86 mmole) in 40 mL of THF added. The temperature of the mixture was allowed to rise to room temperature and it was stirred for 3 hrs. at this temperature, refluxed for 3 hrs., phenethylamine (0.51 mL, 3.86 mmole) was added and the reflux continued for 1 hr. Diethyl ether and NH$_4$Cl (aq) was added to the mixture and the organic phase separated and washed with brine, dried over Na$_2$SO$_4$ and evaporated. The residue was purified by chromatography on silica gel column to yield the titled compound. Mp 204° C. $^1$H NMR (250 MHz, CDCl$_3$) δ 11.32 (br s, 1H), 8.29 (d, 1H), 7.48 (d, 1H), 7.28 (m, 6H), 3.59 (t, 2H), 2.96 (t, 2H).

EXAMPLE 39

(+,–)-N-[cis-2-(6-Chloro-3-ethoxy-2-fluorophenyl) cyclopropyl]-N'-[2-(5-chloro)pyridazyl]-urea The titled compound was obtained starting from 4-chloro-2-fluorophenol which was converted to 6-chloro-3-ethoxy-2-fluorobenzaldehyde according to procedure in Example 362 of WO 93/03022. This aldehyde was converted to 6-chloro-3-ethoxy-2-fluorostyrene according to procedure in Example 375 of WO 93/03022. Styrene (30.7 g, 153 mmole) was dissolved in dichloroethane (400 mL) and CuJ (50 mg) and Pd(OAc)$_2$ (50 mg) added. The temperature of this solution was raised to reflux and diethyl azodicarboxylate (32.2 mL, 306 mmole) in 100 mL of dichloroethane was dropped into it during a period of 2 hrs. The reflux was continued for 1 hr. The reaction mixture was evaporated and the residue purified by chromatography on silica gel column EtOAc/Hexane 2:98–5:95 as eluent to give 4.36 g (10%) of pure (+,–)-cis-2-(6-chloro-3-ethoxy-2-fluorophenyl)-cyclopropylcarboxylic acid ethyl ester which was then hydrolyzed in KOH (2.56 g)—EtOH/H$_2$O (45 mL/5mL) at 100° C. for 24 hrs. The reaction mixture was extracted twice with hexane, made acidic with conc. HCl and extracted with diethyl ether which was dried over Na$_2$SO$_4$ and evaporated to give 3.87 g (98%) of pure acid.

(+,–)-cis-2-(6-Chloro-3-ethoxy-2-fluorophenyl)-cyclopropylcarboxylic acid (1.0 g, 3.87 mmole), diphenyl phosphoryl azide (0.92 mL, 4.26 mmole) and triethylamine (0.59 mL, 4.26 mmole) in 25 mL of toluene was refluxed for 40 min. 3-Amino-6-chloropyridazine (0.55 g, 4.26 mmole) in 20 mL of DMF was added and reflux was continued for 3 hrs. The toluene was evaporated. H$_2$O was added to the residue and extracted with diethyl ether. The precipitate which formed in the H$_2$O phase (a part of the product) was filtrated, the diethyl ether phase was dried over Na$_2$SO$_4$ and evaporated (the other part of the product). The collected crude material (1.2 g) was recrystallized from acetonitrile to give 0.7 g (47%) of the titled compound. Mp 210–211° C. $^1$H NMR (250 MHz, DMSO-d$_6$) 6 9.87 (s, 1H), 8.10 (d, 1H), 7.81 (d, 1H), 7.33 (d, 1H), 7.17 (t, 1H), 7.01 (br s, 1H), 4.16 (q, 2H), 3.33 (m, 1H), 2.13 (q, 1H), 1.58 (q, 1H), 1.41 (t, 3H), 1.22 (m, 1H).

EXAMPLE 40

(+,–)-N-[cis-2-(2-Chloro-3-ethoxy-6-fluorophenyl) cyclopropyl -N'-2-(5-chloro)pyridazyl]-urea The titled compound was obtained starting from 2-chloro-4-fluorophenol and prepared as described in Example 39. Mp 192° C. $^1$H NMR (250 MHz, CDCl$_3$) δ 10.70 (br s, 1H), 8.00 (m, 1H), 7.37 (d, 1H), 6.86 (t, 1H), 6.74 (m, 1H), 4.05 (q, 2H), 3.44 (m, 1H), 2.16 (g, 1H), 1.64 (q, 1H), 1.43 (m, 4H).

EXAMPLE 41

(+,–)-N-[cis-2-(2-Chloro-3-ethoxy-6-fluorophenyl) cyclopropyl]-N'-[2-(5-cyano)pyridyl]-urea Preparation of 2-amino-5-cyanopyridine: A mixture of NiBr$_2$ (2.18 g, 10 mmole), triphenylphosphine (10 a, 38 mmole) and zinc powder (1 g, 15.2 mmole) in 100 mL of acetonitrile was stirred under nitrogen at 60° C. for 1 hr. NaCN (6.3 g, 102 mmole) and 2-amino-5-bromopyridine (17.8 g, 100 mmole) were added to the mixture which was stirred overnight at 60° C. 500 mL of ethyl acetate was added to the mixture and it was filtered and the solvent evaporated. The product was purified on a silica gel column eluted with ethyl acetate. $^1$H NMR (250 MHz, DMSO-d$_6$) δ 8.41 (d, 1H), 7.29 dd, 1H), 7.12 (s, 2H), 6. 58 (d, 1H).

The titled compound was obtained starting from 2-chloro-4-fluorophenol and prepared as described in Example 39. The last step was made using 2-amino-5-cyanopyridine prepared above instead of 2-amino-5-chloropyridazine. Mp 201° C. $^1$H NMR (250 MHz, CDCl$_3$) 6 9.83 (br s, 1H), 9.36 (br s, 1H), 8.14 (d, 1H), 7.71 (dd, 1H), 6.93–6.84 (m, 3H), 4.11 (q, 2H), 3.29 (m, 1H), 2.14 (q, 1H), 1,64 (mr, 1H), 1.53 (t, 3H), 1.33 (m, 1H).

EXAMPLE 42

(+,–)-N-[cis-2-(2-Chloro-3-ethoxy-6-fluorophenyl) cyclopropyl] -N'[5-(4-bromo-3-methyl)pyrazyl]-urea The titled compound was obtained starting from 2-chloro-4-fluorophenol and prepared as described in Example 39. The last step was made using 5-amino-4-bromo-3-methypyrazole hydrobromide instead of 2-amino-5-chloropyridazine. $^1$H NMR (250 MHz, CDCl$_3$) δ 7.30 (m, 1H), 7.01 (br s, 1H), 6.96–6.80 (m, 2H), 5.40 (br s, 1H), 4.07 (q, 2H), 3.30 (m, 1H), 2.14 (m, 1H), 2.00 (s, 3H), 1.65 (q, 1H) 1.44 (m, 4H).

EXAMPLE 43

(+,–)-N-[cis-2-(6-chloro-3-ethoxy-2-fluorophenyl) cyclopropyl]-N'[2-(5-cyano)pyridyl]-urea The titled compound was obtained starting from 4-chloro-2-fluorophenol and prepared as described in Examples 39+41. Mp 211–212° C. $^1$H NMR (250 MHz, DMSO-d$_6$) δ 9.94 (s, 1H), 8.43 (s, 1H), 8.15 (d, 1H), 8.03 (br s, 1H), 7.53 (d, 1H), 7.40 (d, 1H), 7.19 (t, 1H), 4.16 (q, 2H), 3.30 (m, 1H), 2.16 (q, 1H), 1.42 (t, 3H), 1.19 (m, 1H).

EXAMPLE 44

N-[2-(3-Acetyl-6-fluoro-2-methoxy)phenethyl]-N'-[2-(5-chloro)pyridyl]-urea

N-[2-(3-Acetyl-6-fluoro-2-methoxy)phenethyl]-N'-[2-(5-chloro)pyridyl]-thiourea from Example 55 (1.0 g, 2.6 mmole) was dissolved in 20 mL of dioxane/H₂O (10:1) and AgNO₃ dissolved in 5 mL of H₂O was added dropwise to this solution at room temperature. The mixture was stirred for 2 hrs. at room temperature. EtOAc was added to this mixture and it was filtrated through a Celite column EtOAc as eluent. The filtrate was washed with H₂O and brine, dried over NaSO₄ and evaporated. The residue was purified by Silicagel column chromatography EtOAc/hexane 50:50—EtOAc 100 as eluent to give the titled compound. Mp 180° C. ¹H NMR (250 MHz, CDCl₃) δ 9.75 (m, 1H), 8.80 (br s, 1H), 7.63 (d, 1H), 7.54 (t, 1H), 7.10 (d, 1H), 6.88 (t, 1H), 3.80 (s, 3H), 3.58 (q, 2H), 3.01 (t, 2H), 2.57 (s, 3H).

EXAMPLE 45

N-(2-phenethyl)-N'-(2-benzothiazolyl)-urea 2-phenethylamine (0.88 ml, 7 mmole) was added dropwise into the solution of 1,1'-carbonyldimidazole (1.24 g, 7.7 mmole) in dichloromethane (21 ml) at 0° C. After 3 hrs, the react-on mixture was evaporated in vacuo; and the residue was redissolved in dimethylformaldehyde (20 ml). To the solution was added 2-aminobenzothiazole (1.05 g, 7 mmole). The reaction was kept under 100° C. overnight. It was the poured into water (100 ml) and extracted with dichloromethane twice. The organic phase was washed successively with 0.5 N hydrochloric acid solution and water, and subsequently dried in vacuo. The product was crystallized from dichloromethane (1.16 g). Mp 136° C. ¹H NMU (CDCl₃): 7.22 (m, 9H, phenyl and benzo), 3.60 (q, 2H, CH₂NH), 2.75 (t, 2H, CH₂).

EXAMPLE 46

N-(2-phenethyl)-N', N'-methyl-(2-thiazolyl)-urea

Acetic anhydride (10 ml) and formic acid (10 m) were mixed at 0° C., and then heated to 50° C. for 15 min. After cooling to 0° C., a mixture of 2-aminothiazole (2 g, 20 mmole) and formic acid (20 ml) was added to it. The reaction was kept at room temperature overnight. After evaporation and coevaporation with toluene, 2-formamidothiazole was obtained (2.2 g).

2-formamidothiazole (1.6 g, 14 mmole) was dissolved in dry tetrahydrofuran. To the solution was added aluminium hydride (0.8 g, 21 mmole). The reaction mixture was refluxed for 3 hrs, and poured onto ice. It was extracted with dichloromethane three times, and the organic solution was washed with water and evaporated. 2-methylaminothiazole was isolated by alumina column chromatography.

2-phenethylamine (0.38 ml, 3 mmole) was added dropwise into the solution of 1,1'-carbonyldimidazole (0.48 g, 3 mmole) in dichloromethane (15 ml) at 0° C. After 1 hr., the reaction mixture was evaporated in vacuo; and the residue was redissolved in dimethylformaldehyde (10 ml). To the solution was added 2-methylamino thiazole (C.25 g, 2 mmole). The reaction was kept under 100° C. for two hours. It was then poured into water (100 ml) and extracted with dichloromethane twice. The organic phase was washed successively with 0.5 N hydrochloric acid solution and water, and subsequently dried in vacuo. The title product was isolated by silica gel column chromatography (203 mg).

¹H NMR (CDCl₃: 7.27 (m, 6H, phenyl and thiazole), 6.86 (d,

¹H, thiazole), 3.63 (q, 2H, CH₂NH), 3.43 (s, 3H, CH₃) 2.90 (t, 2H, CH₂).

EXAMPLES 47 & 48

N-(cis)-2-(2,5-Dimethoxyphenyl)-cyclopropyl-N'-(5-chloropyrid-2-yl)-urea

N-(trans)-2-(2,5-Dimethoxyphenyl)-cyclopropyl-N'-(5-chloropyrid-2-yl)-urea 2,5-Dimethoxybenzaldehyde (Aldrich) was converted to a cis/trans mixture of 2-(2,5-dimethoxyphenyl)-cyclopropylisocyanates according to the methods described in Examples 375 and 348 of WO 93/03022. This product was then condensed with 2-amino-5-chloropyridine in a manner analogous to the method in Example 7 to provide cis/trans mixture of N-2-(2,5-Dimethoxyphenyl)-cyclopropyl-N'-(5-chloro-pyrid-2-yl)-ureas. The two products were separated on a silica-gel column eluated with mixtures of hexane and ethylacetate: N-(cis)-2-(2,5-Dimethoxy-phenyl)cyclopropyl-N'-(5-chloro-pyrid-2-yl)-urea: Mp 155–157° C. ¹H NMR (250 MHz, CDCl₃) δ 9.81 (br s, 1H), 8.85 (br s, 1H), 7.57 (s, 1H), 7.40 (dd, 1H), 6.92–6.63 (m, 4H), 3.79 (s, 3H)1, 3.70 (s, 3H), 3.29 (m, 1H), 2.41 (q, 1H), 1.39–0.97 (m, 2H).

N-(trans)-2-(2,5-Dimethoxyphenyl)-cyclopropyl-N'-(5-chloropyrid-2-yl)-urea: ¹H NMR (250 MHz, CDCl₃) δ 9.45 (br s, 1H), 8.23 ( s, 1H), 7.62 (d, 1H), 6.89–6.62 (m, 3H), 6.59 (m, 1H), 3.82 (s, 3H), 3.77 (s, 3H), 3.08–2.86 (m, 1H), 2.42–2.29 (m, H) 1.39–1.20 (m, 2H).

EXAMPLE 49

N-(cis)-2-(2,5-Dlmethoxyphenyl)-cyclopropyl-N'-(5-bromopyrid-2-yl)-urea 2-(2,5-Dimethoxyphenyl)-cyclopropylisocyanates prepared as described in the Example above, were condensed with 2-amino-5-bromopyridine according to the method used in Example 7 to provide N-(cis)-2-(2,5-Dimethoxyphenyl)-cyclopropyl-N'-(5-bromopyrid-2-yl)-urea after chromatography on silica gel. Mp 191–192° C. ¹H NMR (250 MHz, CDCl₃) δ 8.79 (br s, ¹H), 7.70 (br s, 1H), 7.55 (dd, ¹H), 6.88–6.62 (m, 4H), 3.81 (s, 3H), 3.72 (s, 3H), 3.29 (m, 2H), 2.40 (q, 2H), 1.4–1.30 (m, 1H), 1.09–0.98 (m, 1H).

EXAMPLE 50

N-(cis)-(3-Ethoxy-2-fluoro-6-methoxyphenyl)-cyclopropyl-N'-(5-bromopyrid-2-yl)-urea A suspension of 2-fluoro-4-methyl acetophenone (10.0 g, 0.059 mol), mCPBA (26.0 g, 0.128 mol) and MgSO₄ (30.0 g) in 500 mL of CHCl₃ was stirred for 12 hrs. at RT. The mixture was then filtrated, washed with 2M NaOH, dried over Na₂SO₄ and concentrated in vacuo to give 1-acetyl-2-fluoro-4-methoxybenzene as a solid (10.7 g, 98%). A solution of the 1-acetyl-2-fluoro-4-methoxybenzene (5.3 g, 0.029 mol) in 100 mL of MeOH and 20 mL of 25% NH₃ (aq) was stirred for 1 hr. at RT. The mixture was then concentrated in vacuo, diluted with water, extracted with EtOAc, dried over Na₂SO₄ and concentrated in vacuo to give 2-fluoro-4-methoxyphenol as an oil (3.85 g, 94%). 2-Ethoxy-1-fluoro-4-methoxybenzaldehyde was prepared according to method described in Example 362 of WO 93/03022 and converted to a cis/trans mixture of 2-(2-ethoxy-1-fluoro-6-methoxyphenyl) cyclopropylisocyanates according to the methods described in Examples 375 and 348 of WO 93/03022. This product was then condensed with 2-amino- 5-bromo-pyridine in a manner analogous to the method in Example 7 to provide cis/trans mixture of N-2-(2-ethoxy-1-fluoro-6-methoxyphenyl)cyclopropyl-N'-(5-bromopyrid-2-yl)-ureas. The two products were separated on a silica-gel column eluated with mixtures of hexane and ethylacetate to yield N-(cis)-(3-ethoxy-2-fluoro-6-methoxyphenyl)-cyclopropyl-N'-(5-bromopyrid-2-yl)-urea: ¹H NMR (250 MHz, CDCl₃) δ 7.88 (s, 1H), 7.55 (dd, 1H), 6.83 (t, 1H),6.58 (dd, 1H), 4.03 (q, 2H), 3.79 (s, 3H), 3.32–3.19 (m, 1H), 1.54–1.20 (m, 2H), 1.46 (t, 3H).

EXAMPLE 51

N-(3-Ethoxy-2-fluoro-6-methoxyphenyl)-N'-(5-chloropyrid-2-yl)-urea

3-Ethoxy-2-fluoro-6-methoxyphenethylamine was prepared from 2-ethoxy-1-fluoro-4-methoxy-benzaldehyde (prepared as described in the Example above) as described in Example 151 of WO 93/03022. 3-Ethoxy-2-fluoro-6-methoxyphenethylamine was reacted with 5-chloropyrid-2-ylisothiocyanate as described in Example 370 of WO 93/03022 to give N-[2-(3-ethoxy-2-fluoro-6-methoxy)-phenethyl] -N'-[2-(5-chloro)pyridyl]-thiourea. The title compound was obtained from N-[2-(3-ethoxy-2-fluoro-6-methoxy)phenethyl]-N'-[2-(5-chloro)pyridyl]-thiourea according to the procedure in Example 4. Mp 194–196° C.; $^1$H NMR (250 MHz, CDCl$_3$) 6 9.20 (br s, 1H), 9.05 (br s, 1H), 8.05 (d, 1H), 7.50 (dd, 1H), 6.82 (d, 1H), 6.74 (d, 1H), 4.00 (q, 2H), 3.73 (s, 3H), 3.59 (dd, 2H), 2.98 (dd, 2H), 1.41 (t, 3H).

EXAMPLE 52

N-(cis)-2-(2-Chloro-3-ethoxy-6-fluorophenyl)-cyclopropyl-N'-(6-bromo-5-hydroxypyrid-2-yl)-urea Starting materials 3-acetyl-6-amino-2-bromopyridine and 2-(2-chloro-3-ethoxy-6-fluorophenyl)-cyclopropylisocyanaze, were prepared in following manner: 5 g of 2-Bromo-3-pyridine (Aldrich) was added to a mixture of 25 ml of conc. H$_2$SO$_4$ and 25 ml of fuming HNO$_3$ at 0° C. The mixture was stirred one hour at that temperature, then added to 350 ml of crushed ice and extracted with CH$_2$C$_{12}$. The extract was dried with Na$_2$SO$_4$ and evaporated in vacuo to yield 4.1 g of a crude product as a mixture of 2-bromo-6-nitro-3-pyridinol and 2-bromo-4,6-dinitro-3-pyridinol. The mixture (0.5 g) was treated with an excess of acetic anhydride at room temperature at 24 hours, then separated on a silica-gel column elueted with mixtures of hexane and ethylacetate to yield 0.28 g of 2-bromo-6- nitro-3-pyridinol as a yellowish solid. 2-Bromo-6-nitro-3-pyridinol was then treated with acetic anhydride at 80° C. at 14 hours under an atmosphere of nitrogen to yield 0.34 g of 3-acetyl-2-bromo-6-nitropyridine as a yellow solid. Hydrogenation of 3-acetyl-2-bromo-6-nitropyridine in ethanol ( Pt on C, 1 atm) gave 3-acetyl-6-amino-2-bromopyridine as a reddish oil. The cis/trans mixture of 2-(2-chloro-3-ethoxy-6-fluorophenyl)cyclopropyliso-cyanates were prepared from 2-chloro-4-fluorophenol (Aldrich) in manner analogous to Examples 362, 375 and 348 of WO 93/03022. This product was then condensed with 3-acetyl-6-amino-2-bromopyridine in a manner analogous to the method in Example 7 to provide cis/trans mixture of N-2-(2-Chloro-3-ethoxy-6-fluorophenyl)-cyclopropyl-N'-(6-bromo-5-hydroxypyrid-2-yl)-ureas. The two products were separated on a silica-gel column elueted with mixtures of hexane and ethylacetate to yield the titled compound as a white solid: $^1$H NMR (250 MHz, CDCl$_3$) δ0 7.85 (d, 1H), 7.55 (br s, 1H), 6.98–6.72 (m, 2H), 4.04 (q, 2H), 3.27–3.04 (m, 1H), 2.18 (q, 1H), 1.74–1.65 H, (m, 1H), 1.43 (t, 3H), 0.92–0.80 (m, 2H).

EXAMPLE 53

N-(cis/trans)-2-(2-Chloro-3-ethyl-6-fluorophenyl)-cyclopropyl-N'-(6-bromo-5-methoxypyrid-2-yl)-urea Starting material -2-amino-6-bromo-5-methoxybromopyridine, was prepared in following manner: 2-bromopyridin-3-ol (Aldrich) was converted to 2-bromo-3-methoxy-6-nitropyridine as described in *J. Med. Chem.* 1981, 24, 39–42. Hydrogenation of 2-bromo-6-nitro-5-methoxypyridine in ethanol (Pt on C, 1 atm) gave the starting material as a reddish oil. This product was then condensed with cis/trans mixture of 2-(2-chloro-3-ethoxy-6-fluorophenyl)cyclopropyliso-cyanates, described in Example 53, in a manner analogous to the method n Example 7 to provide cis/trans (50:50) mixture of N-2-(2-Chloro-3-ethoxy-6-fluorophenyl)-cyclopropyl-N'-(6-bromo-5-hydroxypyrid-2-yl)-ureas. $^1$H NMR (250 MHz, CDCl$_3$) δ 7.62–7.43 (m, 1H), 7.29–7.12 (m, 1H), 6.91–6.67 (m, 2H), 4.10–3.94 (m, 2H), 3.90 and 3.84 (2 s, 3H), 3.38–3.02 (m, 1H) 2.18–2.00 (m, 1H), 1.55–1.30 H (m, 5H), 1.43 (t, 3H), 0.92–0.80 (m, 2H).

EXAMPLE 54

N-(3-Acetyl-2-fluoro-6-methoxyphenyl)-N'-(5-chloropyrid-2-yl)-urea

Starting material 3-acetyl-2-fluoro-6-methoxyphenylamine, was prepared in following manner: A mixture of 2-Fluoro-4-methoxyacetophenone (5 g)(Fluorochem), ethylene glycol (4 ml), and p-toluensulfonic acid (50 mg) in toluene was refluxed 10 hours to give 5.7 g of 2-(2-fluoro-4-methoxyphenyl)-2-methyl-1,3-dioxolane. This was converted to 2-fluoro-6-methoxy-3-(2-methyl-1,3-dioxol-2-yl)-benzaldehyde according to Example 362 of WO 93/03022. This compound was converted to 2-fluoro-6-methoxy-3-(2-methyl-1,3-dioxol-2-yl)-cinnamic acid ethylester according to the methods described in Example 353 of WO 93/03022. 2-Fluoro-6-methoxy-3-(2-methyl- 1,3-dioxol-2-yl)cinnamic acid ethylester was then treated with KOH in dioxane and water to yield 2-fluoro-6-methoxy-3-(2-methyl-1,3-dioxol-2-yl)cinnamic acid. Hydrolysis with aqueous HCl in dioxane gave 3-acetyl-2-fluoro-6-methoxycinnamic acid. N-(3-Acetyl-2-fluoro-6-methoxyphenyl)-N'-(5-chloropyrid-2-yl)-urea was then prepared in a manner analogous to the method in Example 7. $^1$H NMR (250 MHz, CDCl$_3$) δ 9.18 (br s, 1H), 8.97 (br s, 1H), 7.85 (d, 1H), 7.83 (t, 1H), 7.51 (dd, 1H), 6.83 (d, 1H), 6.70 (d, 1H), 3.82 (s, 3H), 3.57 (q, 2H), 3.08–2.92 (m, 2H), 2.51 (d, 3H).

EXAMPLE 55

(+,−)-N-(cis-2-(2-fluoro-5-butoxyvinyl-6-methoxymethoxyph enyl)cyclopropyl)-N'-(5-chloropyrid-2-yl)-urea 3-Fluorophenol (40 ml, 442 mmole) and 2,3-dihydropyrane (45 ml, 500 mmole) were dissolved in dichloromethane and hydrogen chloride in ether (20 ml, 1M) was added. The solution was stirred for 2 hours and was washed with sodium hydroxide in water followed by water. The solution was dried with sodium sulphate, filtered and evaporated. The residue was distilled at 0.5 mm Hg at 85° C. to furnish 50 g of colorless oil. The oil was dissolved in THF under nitrogen and the solution was cooled to −78° C. n-Butyllithium (112 ml, 2,5M) was added. The solution was stirred at −78° C. for 40 minutes. Triethylorthoformate (47 ml, 282 mmole) was added followed by trimethylsilyltriflate (54 ml, 280 mmole). The solution was diluted with hexane and washed with water. The organic phase was dried with sodium sulphate, filtered and evaporated. The residue was purified on silica eluting with ethyl acetate-hexane 1:10. The pure fractions were combined and evaporated to yield 30 g of an oil. The oil was dissolved in THF under nitrogen. The solution was cooled to −78° C. and n-BuLi (44 ml, 2.5 M) was added. The solution was warmed to −30° C. for 20 seconds and was then cooled to −50° C. for 5 minutes and then further cooled to −78° C. for 30 minutes. Iodine (28.1 g, 111 mmole) dissolved in THF was added. The solution was diluted with hexane and washed with water containing a little sodium thiosulphate. The solution was dried with sodium sulphate, filtered and evaporated. The residue was purified by recrystallisation from n-hexane to yield 23.22 g of solid. The solid was dissolved in dioxane and dilute hydrochloric acid was added. The solution was stirred for 60 minutes, diluted with hexane and washed with water. The organic phase was dried with sodium sulphate, filtered and evaporated to yield 13.5 g of solid. The solid was dissolved in dichloromethane and triethylamine (8 ml) and methoxymethylchloride (4.1 ml) was added. The solution was stirred for 60 minutes and was washed with water dried with sodium sulphate, filtered and evaporated. The residue was added to a pre-formed solution of ethylenetriphenylphosphorane (56 mmole) in THF under nitrogen. The solution was stirred for 60 minutes at 60° C. The solution was diluted with hexane, washed with water, dried with sodium sulphate, filtered and evaporated. The residue was purified on silica by elution with ethyl acetate-hexane 1:20. The pure fractions were collected and evaporated to yield 13 g of an oil. The oil was dissolved in dichlorcethane and copper(1) triflate (20 mg) and palladium(2)acetate (20 mg was added) the solution was heated to reflux and ethyldiazoacetate (50 ml) was added slowly. The solution was washed with water and evaporated. The residue was purified on silica by elusion with ethyl acetate-hexane 1:9. The purest fractions containing the cis-isomer were collected and evaporated. The residue was dissolved in methanol and sodium hydroxide in water (ca 15%) was added. The solution was stirred for 60 minutes at 40° C. This treatment hydrolyzed the remaining trans-isomer as well as some other impurity's, but not the wanted cis-ester. The solution was diluted with water and ether, the organic phase washed with water, dried with sodium sulphate, filtered and evaporated to yield 3.3 g pure cis-isomer as an oil. The oil was dissolved in DMF and the solution was degassed 5 mm Hg. Tallium acetate (2.5 g) and n-butylvinylether (5.6 ml) and bis-diphenylphosphinopropane (0.2 g) and palladium acetate (0.1 g) was added under nitrogen. The solution was heated to 90° C. overnight. The solution was diluted with ether, washed with water, dried with sodium sulphate, filtered and evaporated. The residue was purified by on silica by elution with ethyl acetate-hexane 1:9. The pure fractions were collected and evaporated to yield 1.8 g of an oil. The oil was dissolved in methanol and potassium hydroxide (370 mg) was added. The solution was refluxed overnight. The solution was evaporated and co-evaporated 3 times with THF and the solid residue was put onto a freeze drier overnight. 0.5 g of the solid was dissolved in toluene and diphenylphosphorylazide (1 eq.) was added. The solution was refluxed for 20 minutes. 2-Amino-5-chloropyridine (1.2 eq.) was added and the reflux was continued for 40 minutes. The solution was diluted with ethylacetate washed with water, dried with sodium sulphate, filtered and evaporated. The residue was purified on silica by elution with ethylacetate-hexane 1:2. The pure fractions were collected and evaporated to yield 127 mg of the title product. $^1$H-NMR CDCl$_3$ δ 0.9 (t, 3H) 1.3–1.8 (m, 6H) 2.1 (q, 1H) 3.3–3.4 (bs, 1H) 3.5 (s, 3H) 3.8 (t, 2H) 4.3–4.5 (m, 2H) 5.1 (s, 2H) 6.8 (m, 2H) 7.3–7.5 (m, 2H) 7.8 (s, 1H) 9.1 (bs, 1H) 9.8 (bs, 1H).

EXAMPLE 56

(+,−)-N-(cis-2-(5-Acetyl-2-fluoro-6-methoxymethoxy-phenyl)cyclopropyl)-N'-(5-chloropyrid-2-yl)-urea (+,−)-N-(cis-2-(2-fluoro-5-butoxyvinyl-6-methoxymethoxy)-cyclopropyl)-N'-(5-chloropyrid-2-yl)-urea (Example 55) was dissolved in dioxane and a few drops of dilute hydrochloric acid was added. The solution was stirred for 15 minutes, was diluted water and evaporated. The residue was co-evaporated with water to yield the title product as a solid. $^1$H-NMR CDCl$_3$ 1.3 (q, 1H) 1.5 (q, 1H) 2.1 (q, 1H) 2.5 (s, 3H) 3.4 (m, 1H) 3.5 (s, 3H) 5.1 (m, 2H) 6.8 (m, 2H) 7.4–7.6 (m, 2H) 7.8 (d, 1H) 9.1 (bs, 1H) 9.8 (bs, 1H).

EXAMPLE 57

(+,−)-N-(cis-2-(5-Acetyl-2-fluoro-6-hydroxyphenyl)-cyclopropyl)-N'-(5-chloropyrid-2-yl)-urea (+,−)-N-(cis-2-(5-Acetyl-2-fluoro-6-methoxymethoxy)-cyclopropyl)-N'-(5-chloropyrid-2-yl)-urea (Example 56) was dissolved in dioxane and concentrated hydrochloric acid was added. The solution was stirred for 15 minutes, was diluted water and evaporated. The residue was co-evaporated with water to yield the title product as a solid. $^1$H-NMR DMSO-d$_6$ δ 1.2 (m, 1H) 1.3–1.5 (m, 1H) 2.0 (q, 1H) 2.6 (s, 3H) 3.4 (m, 1H) 6.8 (t, 1H) 7.4 (d, 1H) 7.7 (m, 1H) 7.8–8.0 (m, 2H) 9.2 (s, 1H) 11.1 (bs, 1H).

EXAMPLE 58

N-2-(5-Acetyl-2-fluoro-6-hydroxyphenyl)-ethyl)-N'-(5-chloropyrid-2-yl)-urea

4-Fluoro-2-hydroxiacetophenone, (CA registry number: 1481-27-2) (439, 311 mmole) was dissolved in dry THF under nitrogen and benzylbromide (35 ml, 295 mmole) was added followed by sodium hydride, 60% in oil (13 g, 311 mmole). The solution was stirred at 50° C. for 5 hours, diluted with hexane and washed with water. The organic phase was dried with sodium sulphate, filtered and evaporated. The residue was dissolved in a mixture of ethylenglycol (100 ml), dioxane (100 ml) and triethylorthoformate (40 ml). Hydrogen chloride in ether (30 ml, 1M) was added and the solution was stirred for 2 hours The solution was diluted with hexane, washed with water dried with sodium sulphate, filtered and evaporated. The residue was distilled at 140° C. and 5 mm Hg to yield 49 g of an oil. 43 g of the oil was dissolved in dry THF under nitrogen and was cooled to −78° C. and n-BuLi (43 ml, 2, 5M) was added slowly. The solution was stirred for 40 minutes and DMF (30 ml) was added. The solution was diluted with ethyl acetate-water and the organic phase was washed with water, dried with sodium sulphate, filtered and evaporated. The residue was crystallised from hexane to yield 28 g of solid. The solid was dissolved in THF and sodium hydride (5 g, 60% in oil) followed by nitromethane (20 ml) was added. The solution was stirred for 2 hours at 45° C. The solution was diluted with ether, washed with water, dried with sodium sulphate, filtered and evaporated to yield 37 g of an oil. The oil was dissolved in dichloromethane and the solution was cooled to 0° C. Triethylamine (30 ml, 216 mmole) and methanesulphonyl-chloride (9.4 ml, 96 mmole) was added. The solution was stirred at 0° C. for 30 minutes and was then washed with water dried with sodium sulphate, filtered and evaporated to yield 3 g of a solid. The solid was dissolved in THF and LAH (5 g) was added slowly. The solution was refluxed for 30 minutes. Water (15 ml) followed by 15! sodium hydroxide (15 ml) and water again (45 ml) was added slowly and the solution was filtered. The oily residue was dissolved in diethyl ether and was purified by acid-base partitioning (acetic acid-sodium hydroxide). The pure amine was dissolved in ethanol and was hydrogenated over palladium on carbon at atmospheric pressure. The catalyst was added in portions because the amino-group deactivated the catalyst. When 1.2ee hydrogen was consumed the hydrogenation was stopped. The solution was filtered through Celite and was evaporated. The oily product was dissolved in acetonitrile and 5-chloropyrid-2-yl isothiocyanate (5 g) was added. The solution was refluxed for 20 minutes. The product separated on cooling and was collected on a filter to yield 5.6 g of solid. The solid was dissolved in dioxane and dilute hydrochloric acid was added. The solution was stirred for 1 hour and was evaporated to dryness to yield 5.3 g of solid. The solid was dissolved in dioxane containing 156 water. Silver nitrate (25 g) dissolved in water was added. The solution was stirred for 40 minutes, diluted with ethyl acetate, was washed with water dried with sodium sulphate, filtered through Celite and evaporated. The solid was recrystallized from acetonitrile to yield the title product as a solid. $^1$H-NMR DMSO-$d_{6\,8}$6 2.6 (s, 3H) 2.9 (t, 2H) 3.4 (t, 2H) 6.8 (t, 1H) 7.4 (d, 1H) 7.7 (m, 1H) 7.9 (m, 1H) 9.2 (s, 1H) 11.3 (bs, 1H).

EXAMPLE 59

(+, −)-N-(cis-2-(6-chloro-3-ethoxy-2-fluorophenyl)-cyclopropyl)-N'-(5-chloropyrid-2-yl)-urea.

The starting material (+,−)-cis-2-(6-chloro-3-ethoxy-2-fluorophenyl) cyclopropylamine was prepared from 4-chloro- 2-fluorophenol in a manner analogous to Examples 362, 375 and 348 of WO 93/03022. 5–Chloropyrid-2-yl-isothiocyanate was prepared as in Example 374 of WO 93/03022 and then condensed with (+,−)-cis-2-(6-chloro-3-ethoxy-2-fluorophenyl) cyclopropylamine in a manner analogous to Example 370 of WO 93/03022 to give (+,−)-N-(cis-2-(6-chloro-3-ethoxy-2-fluorophenyl) cyclopropyl)-N'-(5-chloropyrid-2-yl)-thiourea. This compound was reacted with NBS according to the procedure in Example 4 0to provide the titled compound. $^1$H NMR (250 MHz, CDCl$_3$) δ1.29–1.38 (m, 1H), 1.45 (t, 1H), 1.57–1.67 (m, 1H), 2.09 (q, 1H), 3.27–3.37 (m, 1H), 4.05 (q, 2H), 6.78–6.85 (m, 2H), 7.14 (dd, 1H) 7.46 (dd, 1H), 7.81 (d, 1H), 9.27 (br s, 1H), 9.47 (br s, 1H)

EXAMPLE 60

(+,−)-N-(cis-2-(2,6-difluoro-3-ethoxyphenyl) cyclopropyl)-N'-(5-chloropyrid-2-yl)-urea The starting material (+,−)-cis-2-(2,6-difluoro-3-ethoxyphenyl)-cyclopropylamine was prepared from 2,4-difluorophenol in a manner analogous to Examples 362, 375 and 348 of WO 93/03022. 5-Chloropyrid-2-yl-isothiocyanate was prepared as in Example 374 of WO 93/03022 and then condensed with (+,−)-cis-2-(2,6-difluoro-3-ethoxyphenyl) cyclopropylamino in a manner analogous to Example 370 of WO 93/03022 to give (+,−)-N-(cis-2-(2,6-difluoro-3-ethoxyphenyl)-cyclopropyl)-N'-(5-chloropyrid-2-yl)-thiourea. This compound was reacted with NBS according to the procedure in Example 4 to provide the titled compound. $^1$H NMR (250 MHz, CDCl$_3$) δ 1.31–1.38 (m, 1H), 1.45 (t, 3H), 1.49–1.58 (m, 1H), 2.06–2.15 (m, 1H), 3.26–3.35 (m, 1H), 4.04 (q, 2H), 6.72–6.85 (m, 3H), 7.48 (dd, 1H), 7.87 (d, 1H), 8.89 (br s, 1H), 9.24 (br s, 1H). Anal. Calc'd. for C$_{17}$H$_{16}$ClF$_2$N$_3$O$_2$: C, 55.52; H, 4.38; N, 11.43. Found: C, 55.2; H, 4.3; N, 11.3.

EXAMPLE 61

(+,−)-N-(cis-2-(3,6-dimethoxy-2-fluorophenyl)-cyclopropyl)-N'-(5-chloropyrid-2-yl)-urea To a solution of 1,4-dimethylbenzene (15.0 g, 0.109 mol) in 300 mL of dry THF was added 2.5 M n-butyllithium (45.6 mL, 0.114 mol) at room temperature under nitrogen. After addition was complete, the solution was stirred for 1 hr. The mixture was cooled to −70° C. and N-fluorobenzenesulfonimide (36.0 g, 0.114 mol) in 150 mL of THF was added slowly, keeping the temperature below −60° C. The solution was allowed to warm to room temperature during the night. 100 mL of NH$_4$Cl (sat) was added and the mixture was extracted with diethyl ether/THF. The organic phase was washed with 1 M NaOH (2×60 mL), dried over MgSO$_4$ and evaporated. Column chromatography (silica gel, n-hexane followed by 1, 5 and 10% EtOAc in n-hexane) provided 11.43 g of a mixture of 1,4-dimethoxy-2-fluorobenzene and 1,4-dimethylbenzene (4.3:1). This mixture was reacted in a manner analogous to Examples 362, 375 and 348 of WO 93/03022 to give (+,−)-cis-2-(3,6-dimethoxy2-fluorophenyl) cyclopropylamine. 5-Chloropyrid-2-ylisothiocyanate was prepared as in Example 374 of WO 93/03022 and then condensed with (+,−)-cis-2-(3,6-dimethoxy-2-fluorophenyl) cyclopropylamine in a manner analogous to Example 370 of WO 93/03022 to give (+,−)-N-(cis-2-(3,6-dimethoxy-2-fluorophenyl)-cyclopropyl)-N'-(5-chloropyrid-2-yl)-thiourea. This compound was reacted with NBS according to the procedure in Example 4 to provide the titled compound. $^1$H NMR (250 MHz, CDCl$_3$) δ 1.23–1.30 (m, 1H), 1.46–1.56 (m, 1H), 1.97–2.07 (m, 1H), 3.21–3.32 (m, 1H), 3.80 (s, 3H), 3.83 (s, 3H), 6.59 (dd, 1H), 6.79–6.92 (m, 2H), 7.46 (dd, 1H), 7.75 (br s, 1H), 8.97 (br s, 1H), 9.20 (br s, 1H).

EXAMPLE 62

N-(2-(3,6-dimethoxy-2-fluorophenyl)ethyl-N'-(5-chloropyrid-2-yl)-urea 1,4-dimethoxy-2-fluorobenzene was prepared as n Example 61 and was reacted in a manner analogous to Examples 362 and 151 of WO 93/03022 to give 3,6-dimethoxy-2-fluorophenethylamine. 5–Chloropyrid-2-ylisothiocyanate was prepared as in Example 374 of WO 93/03022 and then condensed with 3,6-dimethoxy-2-fluorophenethylamine in a manner analogous to Example 370 of WO 93/03022 to give N-(2-(3,6-dimethoxy-2-fluorophenyl)ethyl)-N'-(5-chloro-pyrid-2-yl)-thiourea. This compound was reacted with NBS according to the procedure in Example 4 to provide the titled compound. Anal. Calc'd. for C$_{16}$H$_{17}$ClFN$_3$O$_3$: C, 54.32; H, 4.84; N. 11.88. Found: C, 53.8; H, 4.55; N, 11.65. $^1$H NMR (250 MHz, CDCl$_3$) δ 2.97–3.03 (m, 2H), 3.60 (q, 2H), 3.74 (s, 3H), 3.83 (s, 3H), 6.53 (dd, 1H), 6.79 (t, 1H), 6.88 (d, 1H), 7.52 (dd, 1H), 8.02 (d, 1H), 9.07 (br s, 1H), 9.51 (br s, 1H).

EXAMPLE 63

(+,−)-N-(cis-2-(2-chloro-3-ethoxy-6-fluorophenyl)-cyclopropyl)-N'-methyl-N'-(5-chloropyrid-2-yl)-urea 5-Chloro-2-methylaminopyrrdine was prepared as described by Katritzky et al. in *J. Chem. Soc. Perkin. Trans. I.* 1987, 799–809. The titled compound was obtained starting from 2-chloro-4-fluorophenol according to the procedure in Example 39. The last step was made using cis-2-(2-chloro-3-ethoxy-6-fluorophenyl)cyclopropylcarboxylic acid and 5-Chloro-2-methylaminopyridine. $^1$H NMR (250 MHz, CDCl$_3$) δ 1.20–1.28 (m, 1H), 1.55 (t, 1H), 1.57–1.66 (m, 1H), 2.00–2.09 (m, 1H), 3.21–3.31 (m, 1H), 3.30 (s, 3H), 4.11 (q, 2H), 6.76–6.93 (m, 3H), 7.53 (dd, 1H), 7.86 (d, 1H), 10.0 (br s, 1H).

EXAMPLE 64

(+,−)-N-(cis-2-(2-chloro-3-hydroxy-6-fluorophenyl)-cyclopropyl)-N'-(5-chloropyrid-2-yl)-urea The titled compound was obtained starting from (+,−)-N-(cis-2-(2-chloro-3-ethoxy-6-fluorophenyl)-cyclopropyl)-N'-

(5-chloropyrid-2-yl)-urea (Example 6) and BBr$_3$ using the procedure in *Org. Synth., Coll Vol V*, 1973, 412. $^1$H NMR (250 MHz, DMSO-D$_6$) δ 1.10–1.18 (m, 1H), 1.54–1.62 (m, 1H), 2.10–2.20 (m, 1H), 3.20–3.30 (m, 1H), 6.99–7.16 (m, 2H), 7.32 (d, 1H), 7.84 (dd, 1H), 8.00 (d, 1H), 8.15 (br.s, 1H), 9.56 (br.s, 1H).

EXAMPLE 65

(+,−)-N-(cis-2-(2-hydroxy-3-ethoxy-6-fluoropnenyl)-cyclopropyl)-N'-(5-chloropyrid-2-yl)-urea 5'-Fluoro-2'-hydroxyacetophenone (9.38 g, 61 mmole), iodoethane (7.3 ml, 91 mmole) and K$_2$CO$_3$ (12.6 g, 91 mmole) in acetone (100 ml) was stirred at 60° C. overnight. The mixture was filtered, evaporated, dissolved in hexane/ethyl acetate, washed with 2M NaOH (2×20 ml) and water, dried (MgSO$_4$) and evaporated to give 2'-ethoxy-5'-fluoroacetophenone. A solution of mCPBA )19.3 g, 112 mmole) in CH$_2$Cl$_2$ (500 ml) was dried with MgSO$_4$. 2'-Ethoxy-5'-fluoro-acetophenone (10.2 g, 56 mmole) was added and the mixture was stirred for 3 days. More mCPBA (5 g, 29 mmole) and MgSO$_4$ was added and stirring was continued for 2 days. The mixture was filtered, diluted with ethyl acetate, washed with 2 M NaOH (2×70 ml), NH$_4$Cl (sat, 50 ml), dried (MgSO$_4$) and evaporated. The residue (10.45 g,) was dissolved in ethanol (100 ml). KOH (8.9 g, 160 mmole) was dissolved in water (50 ml). The solutions were combined and stirred for 1 h. The mixture was washed with diethyl ether/hexane 2×(50+25 ml), acidified with HCl (konc), extracted with ethyl acetate (3×100 ml), dried (MgSO$_4$) and evaporated. The residue (8.22 g) was dissolved in CH$_2$Cl$_2$ (100 ml). Triethylamine 11.7 ml, 84 mmole) and bromomethyl methyl ether (6.45 ml, 79 mmole) were added and the solution was refluxed for 2 hrs. More triethylamine 11.7 ml, 84 mmole) and bromomethyl methyl ether (6.45 ml, 79 mmole) were added and refluxing was continued overnight. The solution was evaporated, CH$_2$Cl (200 ml) was added and the solution was washed with water, 2M NaOH and NH$_4$Cl. Drying (MgSO$_4$) and evaporation provided 4.0 g of 1-ethoxy-4-fluoro-2-methoxymethoxybenzene. This compound was reacted in a manner analogous to Example 39 to give (+,−)-N-(cis-2-(3-ethoxy-6-fluoro-2-methoxymethoxyphenyl)-cyclopropyl)-N'-(5-chloropyrid-2-yl)-urea. Finally deprotection with 2 M HCl in dioxane gave the titled compound. $^1$NMR (250 MHz, DMSO-D$_6$) δ 1.04–1.14 (m, 1H), 1.41–1.56 (m+t, 4H), 1.96–2.06 (m, 1H), 3.05–3.15 (m, 1H), 4.06–4.19 (m, 2H), 6.64 (t, 1H), 6.94 (dd, 1H), 7.19 (d, 1H), 7.82 (dd, 1H), 8.10 (d, 1H), 8.61 (br.s, 1H), 9.08 (br.s, 1H), 9.57 (br.s, 1H).

EXAMPLE 66

(+,−)-N-[cis-2-(2-Chloro-3-ethoxy-6-fluorophenyl) cyclopropyl]-N'-[2-(5-ethynyl)pyridyl]-urea Preparation of the intermediate, 2-Amino-5-ethynylpyridine. 2-Amino-5-bromopyridine (8.65 g, 50.0 mmole) and bis-trimethyl-silylacetamide (36.76 mL, 150.0 mmole) was stirred at 100° C. overnight. The mixture was purified by distillation to give 10.41 g (85%) of the protected amine. 2-Trimethylsilylamlno-5-bromopyridine (4.90 g, 20.0 mmole), bis(triphenylphosphine)palladium-(II) chloride (0.70 g, 1.00 mmole) and trimethylsilylacetylene (5.65 mL, 40.0 mmole) in piperidine (2 mL) was stirred under nitrogen at 80° C. overnight. Diethyl ether and NH$_4$Cl (aq) was added to the mixture and the organic phase was separated, dried over Na$_2$SO$_4$ and evaporated. Tetrabutylammonium chloride (50.0 mL, 100.0 mmole) and THF (250 mL) was added to remove the protection groups and the mixture was stirred overnight. THF was evaporated. The residue was purified by silica gel column chromatography (EtOAc/Hexane, 40:60) to give 2.36 g, (61%) of the titled compound. $^1$H NMR (250 MHz, CDCl$_3$) δ 3.05 (s, $^1$H), 4.65 (br s, 2H), 6.45 (d, 1H), 7.50 (dd, 1H), 8.25 (d, 1H).

(+,−)-cis-(2-Chloro-3-ethoxy-6-fluorophenyl)-cyclopropylcarboxylic acid (0,39 g, 1.5 mmole) which was made from 2-chloro-4-fluorophenol according to the procedure in Example 39, was refluxed n toluene with diphenylphosphoryl azide (0.36 mL, 1.7 mmole) and triethylamine (0.23, 1.7 mmole) for 40 min. 2-Amino-5-ethynylpyridine (0.20 g, 1.7 mmole) was added in DMF (10 mL) and reflux was continued for 3 hrs. Toluene was evaporated. The residue was dissolved in EtOAc and washed with HCl (0.1 M) and water. The organic phase was dried over Na$_2$SO$_4$ and evaporated. The residue was purified by silica gel column chromatography (EtOAc/Hexane, 40:60–60:40) to give 0.16 (28%) of the titled compound. Mp 197–198° C. $^1$H NMR (250 MHz, CDCl$^3$) δ 1.2–1.8 (m, 5H), 2.1 (m, 1H), 3.1 (s, 1H), 3.3 (m, 1H), 4.1 (m, 2H), 6.7–7.0 (m, 3H), 7.6 (dd, 1H), 8.0 (d, 1H), 9.2 (s, 1H), 9.5 (br s, 1H).

EXAMPLE 67

(+,−)-N-[cis-2-(2-Chloro-3-ethoxy-6-fluorophenyl) cyclopropyl]-N'-N'-[2-(5-carboxy)pyridyl]-urea (+,−)-cis-(2-Chloro-3-ethoxy-6-fluorophenyl)-cyclopropylcarboxylic acid (See Example 66), (0.26 g, 1.0 mmole) which was made from 2-chloro-4-fluorophenol according to the procedure in Example 39, was refluxed in toluene with diphenylphosphoryl azide (0.24 mL, 1.1 mmole) and triethylamine (0.15, 1.1 mmole) for 40 min. 6-Aminonicotinic acid (0.15 g, 1.1 mmole) in DMF (10 mL) was added and reflux was continued for 3 h. Toluene was evaporated. NaOH(aq) was added and the mixture was washed with EtOAc. It was then made acidic with conc HCl and extracted with EtOAc. The organic phase was washed with water, dried over Na$_2$SO$_4$ and evaporated to give 0.055 g (14%) of the titled compound. Mp 237–238° C. $^1$H NMR (250 MHz, DMSO) δ 1.20 (m, 1H), 1.50 (m, 3H), 1.60 (m, 1H), 2.20 (m, 1H), 3.25 (m, 1H), 3.40 (s, 1H), 4.20 (q, 2H), 7.20 (m, 3H), 8.15 (dd, 1H), 8.40 (s, 1H), 8.80 (br s, 1H), 9.85 (s, 1H).

EXAMPLE 68

(+,−)-N-[cis-2-(2-Chloro-3-ethoxy-6-fluorophenyl) Cyclopropyl]-N'-[2-(5-vinyl)pyridyl]-urea Preparation of the intermediate, 2-Amino-5-vinylpyridine. Vinyltributyltin (3.1 mL, 10.5 mmole) was added dropwise to a mixture of 2-trimethylsilyl-amino-5-bromopyrdine (2.45 g, 10.0 mmole) from Example 66, LiCl (1.27 g, 30.0 mmole) and tris-(dibenzylidene-acetone) dipalladium (0.18 g, 0.2 mmole) in DMF (20 mL). The mixture was stirred overnight under nitrogen at 80° C. KF(aq) and EtOAc was added and the organic phase was separated, dried over Na$_2$SO$_4$ and evaporated. The residue was purified by silica gel chromatography (EtOAc/Hexane, 40: 60) to give 0.12 g (29%) of the titled compound. $^1$H NMR (250 MHz, CDCl$_3$) δ 4.70 (br s, 2H), 5.10 (d, 1H), 3.55 (d, 1H), 6.40–6.65 (m, 2H), 7.55 (dd, 1H), 8.05 (s, 1H).

(+,−)-cis-(2-Chloro-3-ethoxy-6-fluorophenyl)-cyclopropylcarboxylic acid (0.39 g, 1.5 mmole) which was made from 2-chloro-4-fluorophenol according to the procedure in Example 39, was refluxed in toluene with diphenylphosphoryl azide (0.36 mL, 1.7 mmole) and triethylamine (0.23mL, 1.7 mmole) for 40 min. 2-Amino-5-vinylpyridine (0.20 g, 1.7 mmole) in DMF (10 mL) was added and reflux was continued for 3 h. Toluene was evaporated. The residue was dissolved in EtOAc and the solution was washed with HCl (0.1M) and water, dried over $Na_2SO_4$ and evaporated. The residue was purified by silica gel column chromatography (EtOAc/Hexane, 40: 60–60:40) and recrystallized from acetonitrile to give 0.12 g (21%) of the titled compound. $^1$H NMR (250 MHz, $CDCl_3$) δ 1.40 (m, 1H), 1.50 (t, 3H), 1.65 (m, 1H), 2.10 (m, 1H), 3.45 (m, 1H), 4.10 (q, 2H), 5.25 (d, 1H), 5.60 (d, 1H), 6.50–6.95 (m, 4H), 7.60 (dd, 1H), 7.70 (s, 1H), 8.90 (s, 1H), 9.50 (br s, 1H).

EXAMPLE 69

(+,-)-N-[cis-2-(2-Chloro-3-ethoxy-6-fluorophenyl) cyclopropyl]-N'-[2-(5-bromo)pyrazyl]-urea Preparation of the Intermediate 2-Amino-5-bromopyrazine. $Br_2$ (0.61 mL, 12.0 mmole) was added dropwise to 2-aminopyrazine (0.95 g, 10.0 mmole) in pyridine (10 mL). The mixture was stirred at 30° C. for 1 h and at 70° C. for 45 min. $CH_2Cl_2$ was added and the mixture was washed with water and NaOH (1M), filtered, dried over $Na_2SO_4$ and evaporated. The residue was purified by silica gel column chromatography (EtOAc/Hexane, 30:70–40:60) to give 0.50 g (29%)of the titled compound. $^1$H NMR (250 MHz, DMSO) δ 6.80 (s, 2H), 7.80 (s, 1H), 8.15 (s, 1H).

(+,-)-cis-(2-Chloro-3-ethoxy-6-fluorophenyl)-cyclopropylcarboxylic acid (0.52 g, 2.0 mmole) which was made from 2-chloro-4-fluorophenol according to the procedure in Example 39, was refluxed in toluene with diphenylphosphoryl azide (0.47 mL, 2.2 mmole) and triethylamine (0.30 mL, 2.2 mmole) for 30 min. 2-Amino-5-bromopyrazine (0.38 g, 2.2 mmole) was added in DMF (10 mL) and reflux was continued overnight. The mixture was then stirred without heat for another 24 hrs. Toluene was evaporated. The residue was dissolved in EtOAc and the solution was washed with HCl (0.1M) and water, dried over $Na_2SO_4$ and evaporated. The residue was filtered using EtOAc as eluent. The filtrate was evaporated and the residue was further purified by recrystallization in acetonitrile to give 0.088a (10%) of the titled compound. $^1$H NMR (250 MHz, $CDCl_3$) δ 1.30 (m, 1H), 1.55 (m, 3H), 1.65 (m, 1H), 1.30 (m, 1H), 3.25 (m, 1H), 4.10 (q, 2H), 6.75–6.95, (m, 2H), 7.90 (s, 1H), 8.10 (s, 1H), 9.25 (s, 1H).

EXAMPLE I

N-(2-(2.6-Difluorophenethyl)-N'-(5-bromopyrid-2-yl)-guanidinium hydrochloride

To a solution of 5.0 g (32.65 mmole) of 2,6-difluorophenylacetonitrile in 25 ml of anhydrous tetrahydrofuran at room temperature under nitrogen was added 33.0 ml (33.0 mmole) of 1.0 molar boranetetrahydrofuran complex by syringe. The mixture was stirred 4 hours, cooled in an ice bath, and quenched under nitrogen with a solution of 10.7 ml of concentrated hydrochloric acid in 22 ml of water. The mixture was heated to re flux, stirred I hr., and the tetrahydrofuran was removed by downward distillation. The milky white suspension was diluted with 22 ml of toluene and stirred 5 minutes longer. The layers were separated and the aqueous was extracted with 20 ml of hot toluene. The aqueous layer was cooled to 0° C., 50 ml of methylene chloride and 10 ml of 50% sodium hydroxide was added, and the layers were separated. The aqueous layer was extracted with methylene chloride (2×) and the combined organics were dried over sodium sulfate. Concentration gave 2.8 g (55%) of 2,6difluorophenethylamine as a light yellow liquid; $^1$H NMR (300 MHz, $CDCl_3$) δ 7.10–7.30 (m, 1H), 6.80–7.00 (t, 2H), 2.80–3.00 (m, 2H), 2.70–2.80 (m, 2H), 1.35 (s, 2H)

The amine prepared as above (2,6 g, 16.56 mmole) was dissolved in 50 ml of anhydrous ethyl ether and cooled with stirring in an ice water bath. 1.19 (10.3 mmole) of cyanogen bromide dissolved in 15 ml of ethyl ether was added by dropping funnel and the mixture was stirred 1 hr. The resulting solid (2,6 difluorophenethylamine hydrobromide) was filtered off. Concentration of the filtrate gave 1.5 g (50%) of 2,6-difluorophenethyl cyanoacetamide as a yellow off: $^1$H NMR (300 MHz, DMSO-$d_6$) δ 7.20–7.40 (m,1H), (6.80–7.00 (m, 2H), 4.00 (s, 1H), 3.26 (q, 2H), 3.00 (t, 2H).

5.0 g (28.8 mmole) of 2-amino-5-bromopyridine was dissolved in 50 ml of ethanol and cooled to 0° C. with stirring. Hydrogen chloride (g) was bubbled in until the solution was saturated, the ethanol was concentrated to a small volume, ethyl ether was added, and the resulting solid was filtered and dried to give 4.0 g (66%) of 2-amino-5-bromopyridine hydrochloride: $^1$H NMR (300 MHz, DMSO-$d_6$ δ 8.20 (s, 1H), 8.00 (d, 1H), 7.00 (d, 1H), 3.50–5.50 (br, 3H).

750 mg (4.12 mmole) of 2,6-difluorophenethyl cyanoacetamide and 865 mg (4.12 mmole) of 2-amino-5-bromopyridine hydrochloride prepared as above in 20 ml of chlorobenzene was heated at 125° C. under nitrogen for 3.5 hrs. The solution was cooled to room temperature and the resulting solid was filtered. Recrystallization from ethanol/ethyl ether gave 540 mg (33.5%) of the titled compound as a white solid: mp 209–211° C.; IR (KBr, $cm^{-1}$) 3094, 1680, 1627, 1468, 1236, 1000, 829, 775; $^1$H NMR (300 MHz, DMSO-$d_6$) δ 11.45 (br.s., 1H), 9.30 (br.s., 1H), 8.60 (br.s., 2H), 8.30 (d, 1H), 8.10 (dd, 1H), 7.30–7.45 (m, 1H), 7.00–7.20 (m, 3H), 3.60 (q, 2H), 2.95 (t, 2H); MS (FD) m/e 356 (Mt, free base). Anal. Calc'd. for $C_{14}H_{13}BrF_2N_4$ HCl 0.25 $H_2O$: C, 42.45; H, 3.66; N, 14.14. Found: C, 42.53; H, 4.04; N, 14.02.

EXAMPLE II

N-(3-Fluoropyrid-2-yl)eth-2yl-N'-(5-bromopyrid-2-yl)-quanidine

A mixture of 500 mg (3.03 mmole) of N-(3-fluoropyrid-2-yl) eth-2-yl-cyanamide (prepared from N-2-(3-fluoropyrid-2-yl)ethylamine as in Example I), 635 mg (3.03 mmole) of 2-amino-5-bromopyridine hydrochloride (prepared as in Example I), and 15 ml of chlorobenzene was heated at 125° C. under nitrogen for 4 hrs. The mixture was cooled to room temperature, stirred overnight, and concentrated to dryness. The resin was dissolved in 40 ml of IN hydrochloric acid and extracted with ethyl acetate (IX). The aqueous layer was basified with 2N sodium hydroxide and extracted with ethyl acetate (2×). The organic layer was dried over sodium sulfate, concentrated to a resin, and purified by flash silica gel chromatography (methylene chloride/methanol/ammonium hydroxide-46:3:1) to give a yellow oil. Crystallization from ethyl ether gave the titled compound as a pale yellow solid, 200 mg (19.5%): mp 134–137° C.; IR (KBr, $cm^{-1}$) 3400, 3070, 1679, 1573, 1450, 1127, 827, 710; $^1$H NMR (300 MHz, DMSO-$d_6$) δ 8.40 (d, 1H), 8.07 (d, 1H), 7.70–7.90 (m, 2H), 7.30–7.50 (m, 3H), 6.80–7.00 (br, 1H), 6.60 (d, 1H), 3.60 (br.q., 2H), 3.00 (dt, 2H)f; MS (FD) m/e 337 (Mt). Anal. Calc'd. for $C_{13}H_{13}BrFN_5$: C, 46.17; H, 3.88; N, 20.71. Found: C, 46.13; H, 3.68; N, 20.92.

EXAMPLE III

N-(2-(2-Chloro-3-ethoxy-6-fluorophenethyl)-N'-(5-bromopyrid-2-yl)-guanidine

A solution of 380 mg (1.81 mmole) of 2-amino-5-bromopyridine hydrochloride and 440 mg (1.81 mmole) of N-(2-(2-chloro-3-ethoxy-6-fluorophenethyl) cyanamide (prepared as in Example 1) in 15 ml of chlorobenzene was heated at 125° C. for 4 hrs, under nitrogen. The mixture was cooled to room temperature, stirred overnight, and concentrated to dryness. The residue was partitioned between 40 ml of IN hydrochloric acid and ethyl acetate (IX). The organic layer was extracted with 2N sodium hydroxide (IX), dried over sodium sulfate, and concentrated to an orange oil. Purification over a flash silica gel column (methylene chloride/methanol/ammonium hydroxide-92:7:1) provided a yellow oil. Crystallization from ethyl ether gave the titled compound as an off-white solid, 100 mg (13%): mp 169–172° C.; IR (KBr, cm$^{-1}$) 3400, 3100, 1668, 1568, 1465, 1243, 1072, 826, 805; $^1$H NMR (300 MHz , DMSO-d$_6$) δ 8.10 (d, 1H), 7.60 (dd, 1H), 7.35 (br, 2H), 7.10–7.20 (m, 1H), 7.00–7.05 (m, 1H), 6.70–6.90 (br, IH), 6.60 (d, 1H), 4.05 (q, 2H), 3.40 (m, 2H), 3.00 (t, 2H), 1.35 (t, 3H); MS (FD) m/e 416 (Mt). Anal. Calc'd. for $C_{16}H_{17}BrClFN_4O$: C, 46.23; H, 4.12; N, 13.48. Found: C, 46.41; H, 4.18; N, 13.32.

EXAMPLE IV

N-(2-Phenethyl)-N'-(5-bromopyrid-2-yl)-guanidinium hydrochloride

The titled compound was prepared from N-(2-phenethyl) cyanamide and 2-amino-5-bromopyridine hydrochloride as in Example I: mp 176–178° C.; IR (KBr, cm$^{-1}$) 3252, 3100, 1677, 1628, 1586, 1468, 1365, 1235, 826, 705; $^1$H NMR (300 MHz, DMSO-d$_6$) δ 11.5 (br, 1H), 9.30 (br, 1H), 8.55 (br, 2H), 8.35 (d, 1H), 8.06 (dd, 1H), 7.20–7.40 (m, 5H), 7.05 (br.d., 1H), 3.60 (q, 2H), 2.90 (t, 2H); MS (FD) m/e 320 (Me) Anal. Calc'd. for $C_{14}H_{15}BrN_4$ HCl: C, 47.28; H, 4.53; N, 15.75. Found: C, 47.48; H, 4.63; N, 15.81.

EXAMPLE V

N-(2-(2-Fluorophenethyl)-N'-(5-bromopyrid-2-yl)-guanidirlium hydrochloride

The titled compound was prepared from N-(2-(2-fluorophenethyl) cyanamide and 2-amino-5-bromopyridine hydrochloride according to Example I: mp 175–177° C.; IR (KBr, cm$^{-1}$) 3090, 2933, 1679, 1622, 1471, 1227, 833, 759, 635; $^1$H NMR (300 MHz, DMSO-d$_6$) δ 11.48 (br, 1H), 9.30 (br, 1H), 8.55 (br.s., 2H), 8.35 (d, 1H), 8.10 (dd, 1H), 7.40–7.50 (dt, 1H), 7.25–7.38 (m, 1H), 7.20 (t, 2H), 7.06 (br.d., 1H.), 3.62 (q, 2H), 2.86 (t, 2H); MS (FD) m/e 336 (Mt). Anal. Calc'd. for $C_{14}H_{14}BrFN_4$ HCl: C, 45.00; H, 4.05; N. 14.99. Found: C, 45.20; H, 4.03; N, 15.04.

EXAMPLE VI

N-(2-(2-Pyridylethyl)-N'-(5-bromopyrid-2-yl) quanidine

The titled compound was prepared from N-(2-(2-pyridylethyl) cyanamide and 2-amino-5-bromopyridine hydrochloride as in Example II: mp 139–141° C.; IR (KBr, cm$^{-1}$) 3600, 3082, 1681, 1566.

EXAMPLE VII

N-Cyano-{N'-2-phenethyl-N"-[2-(5-chloro)pyridyl]} guanidine

A mixture of Na$_2$NCN (95%, 0.25 g, 2.78 mmole) and Et$_3$N HCl (0.38 g, 2.78 mmole) in EtOH (5 mL) was stirred at room temperature overnight. 2-(5-chloro)pyridyl isothiocyanate (0.48 g, 2.78 mmole), the product of Example 374 of WO 93/03022, was added to the reaction mixture and it was stirred for 1 hr. at room temperature. The solvent was evaporated and 5 mL of DMF and phenethylamine (0.42 mL, mL, 3.34 mmole) added to the residue. The mixture was stirred for 3 min. at room temperature, 1-(3-dimethylaminopropyl)-3-ethylcarbodiimide HCl (0.64 g, 3.34 mmole) was added to it and stirring was continued for 0.5 hr. at room temperature. 30 mL of EtOAc was added to the mixture and it was washed once with 10 mL of 1N HCl and three times with 10 mL of H$_2$O. The collected water phase was made alkaline with 15% NaOH (aq) and extracted with EtOAc which was dried over Na$_2$SO$_4$ and evaporated to yield the titled product. Mp 189–19° C. $^1$H NMR (250 MHz, CDCl$_3$) δ 10.08 (s, 1H), 9.04 (s, 1H), 7.93 (d, 1H), 7.60 (dd, 1H), 7.34–7.21 (m, 6H), 3.69 (q, 2H), 2.92 (t, 2H).

EXAMPLE VIII (+,−)-N-(cis-2-phenylcyclopropyl)-N'-[2-(5-bromo)Pyridyl]guanidine (+,−)-N-(cis-2-phenylcyclopropyl)-N'-[2-(5-bromo)pyridyl]-thiourea (0.2 g, 0.57 mmole), the product of Example 373 of WO 93/03022, and silver triflate (0.22 g, 0.86 mmole) were dissolved in 20 mL of CH$_2$Cl$_2$ at −20° C. NH$_3$ (g) was introduced to this solution at the same temperature. The mixture was stirred and the temperature was allowed to rise slowly to room temperature. Stirring was continued overnight. The mixture was filtrated and the filtrate was evaporated. The residue was stirred with 4N HCl and filtrated. The filtrate was made alkaline and extracted with CH$_2$Cl$_2$ which was dried over Na$_2$SO$_4$ and evaporated to give the titled product. $^1$H NMR (250 MHz, CDCl$_3$) δ 7.82 (br s, 1H), 7.49 (dd, 1H), 7.35–7.22 (m, 6H), 6.66 (d, H), 2.91 (m, 1H), 2.40 (q, 1H), 1.42 (m, 1H), 1.18 (m, 1H).

We claim:

1. A method for treating HIV which comprises administering to a patient in need thereof, an effective anti-HIV amount of a compound of the formula

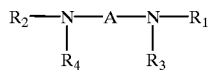

(1A)

wherein A

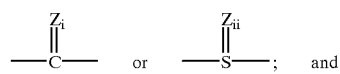

$Z_i$ is O, Se, NR$^a$ or C(R$^a$)$_2$, and $Z_{ii}$ is —O or (=0)$_2$; and wherein R$^a$ is H, OR$^b$, CN, NO$_2$, N(R$^b$)$_2$, SR$^b$, SO$_2$R$^b$, SO$_2$NZ(R$^b$)$_2$, COR$^b$, CO$_2$R$^b$, CON(R$^b$)$_2$, PO(R$^b$)$_2$, PO(OR$^b$)$_2$, PO(NR$^b$)$_2$,wherein R$^b$ is hydrogen, C$_1$–C$_6$ alkyl, C$_1$–C$_6$ substituted alkyl, $C_2$–$C_6$ alkenyl, $C_2$–$C_6$ substituted alkenyl, $C_2$–$C_8$ alkynyl, $C_2$–$C_8$ substituted alkynyl, $C_1$–$C_6$ alkoxy, $C_1$–$C_6$ substituted alkoxy, $C_{4-10}$ aralkyl, $C_{1-10}$ alkaryl, $C_{1-10}$ alkylthio, $C_{4-10}$ aralkylthio, $C_{1-10}$ alkylsulfinyl, $C_{4-10}$ alkylsulfinyl, $C_{1-10}$ alkylsulfonyl, $C_{4-10}$ aralkylsulfonyl, carboxy, $C_{1-10}$ alkylthiocarbonyl, $C_{4-10}$ aralkylcarbonyl, $C_{4-10}$ aralkylthiocarbonyl, $C_{4-10}$ aralkoxycarbonyl, $C_{4-10}$ aralkoxycarbonyl, $C_{1-4}$ alkyl, $C_{4-10}$ aralkoxy, $C_{1-12}$ dialkylamino-$C_{1-6}$ aralkanoylamino $C_{4-10}$ aralkylamino or $C_1$–$C_4$ alkanoyloxy;

$R_1$ is a stable saturated or unsaturated, substituted or unsubstituted, 6 membered organic monocyclic ring having 2 to 4 N atoms;

$R_2$ is a group of the formula

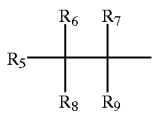

wherein $R_5$ is a stable, saturated or unsaturated, substituted or unsubstituted 3 to 8 member organic monocyclic ring having 0 to 4 heteroatoms selected from S, O and N; or $R_5$ is a stable, saturated or unsaturated, substituted or unsubstituted 7 to 10 membered organic bicyclic ring having 0 to 5 heteroatoms selected from S, O or N;

$R_6$, $R_7$, $R_8$, and $R_9$ are independently $C_3$–$C_8$ cycloalkyl, hydrogen, $C_1$–$C_6$ alkyl, $C_2$–$C_6$ alkenyl, $C_2$–$C_6$ alkynyl, substituted $C_2$–$C_6$ alkyl, substituted $C_2$–$C_6$ alkenyl, or substituted $C_2$–$C_6$ alkynyl, $C_1$–$C_6$ substituted alkoxy, halo, amino, nitro, cyano, $C_1$–$C_5$ alkoxy, hydroxy, carboxy, hydroxymethyl, aminomethyl, carboxymethyl, $C_1$–$C_4$ alkylthio, $C_1$–$C_4$ alkanoyloxy, carbamoyl, or a halo substituted $C_1$–$C_6$ alkyl; or two of which, along with the carbons to which they are attached, combine to form a stable, saturated or unsaturated, substituted or unsubstituted, 3 to 7 membered organic monocylic ring having 0 to 4 hetero atoms selected from S, O, or N;

$R_3$ and $R_4$ are independently hydrogen, hydroxy, $C_1$–$C_6$ alkyl, $C_2$–$C_6$ alkenyl, $C_2$–$C_6$ alkynyl, substituted $C_1$–$C_6$ alkyl, substituted $C_2$–$C_6$ alkenyl, or substituted $C_2$–$C_6$ alkynyl, substituted alkoxy, amino, cyano, nitro, $C_1$–$C_6$ alkoxy, $C_1$–$C_6$ substituted alkoxy, carboxy, hydroxymethyl, aminomethyl, carboxymethyl, $C_1$–$C_4$ alkylthio, $C_1$–$C_4$ alkanoyloxy, halo-substituted $(C_1$–$C_6)$alkyl, or carbamoyl; or a pharmaceutically acceptable salt thereof.

2. The method of claim 1 wherein $R_5$ is selected from the group consisting of cyclo($C_3$–$C_8$)alkyl, cyclo ($C_3$–$C_8$) alkenyl, isothiazolyl, substituted isothiazolyl, tetrazolyl, substituted tetrazolyl, triazolyl, substituted triazolyl, pyridyl, substituted pyridyl, imidazolyl, substituted imidazolyl, phenyl, substituted phenyl, naphthyl, substituted naphthyl, benzoxazolyl, substituted benzoxazolyl, benzimidazolyl, substituted benzimidazolyl, thiazolyl, substituted thiazolyl, oxazolyl, substituted oxazolyl, benzothiazolyl, substituted benzothiazolyl, pyrazinyl, substituted pyrazinyl, pyridazinyl, substituted pyridazinyl, thiadiazolyl, substituted thiadiazolyl, benzotriazolyl, substituted benzotriazolyl, pyrrolyl, substituted pyrrolyl, indolyl, substituted indolyl, benzothienyl, substituted benzothienyl, thienyl, substituted thienyl, benzofuryl, substituted benzofuryl, furyl, substituted furyl, quinolinyl, substituted quinolinyl, isoquinolinyl, substituted isoquinolinyl, pyrazolyl, and substituted pyrazolyl.

3. The method of claim 1, wherein $R_1$ is pyrazinyl, substituted pyrazinyl, pyrimidinyl, substituted pyrimidinyl, pyridazinyl, or substituted pyridazinyl.

4. The method as recited in claim 1 further comprising administering at least one other anti-HIV agent with said HIV.

5. The method of claim 1, wherein $Z_i$ is O.

6. The method of claim 1 wherein $R_3$ and $R_4$ are hydrogen:

$R_1$ is (6-chloro)pyrazinyl, (6-bromo)pyrazinyl, 3-(6-bromo)pyridazinyl, (5-cyano)pyrazinyl, (6-cyano) pyrazinyl, 3-(6cyano)pyridazinyl, (5chloro)pyrazinyl, (5-bromo)pyrazinyl, (6-chloro)pyridazinyl, 2-(3-[6-bromo]pyridazinyl), 2-(3-[6-chlorolpyridazinyl), 2-(3-[6-cyano]pyridazinyl), 3-(6-methoxy)pyridazinyl, 4-(6-aminopyrimidinyl), 4pyrimidinyl, 2-(3pyddazinyl), 2-(3-[6-methyl]pyridazinyl), 2-pyrazinyl, 2-(5methyl)pyrazinyl;

$R_2$ is

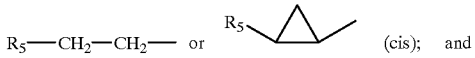

$R_5$ is phenyl, 2-methoxyphenyl, 3-methoxyphenyl, 4methoxyphenyl, 2-ethoxyphenyl, 2-methylphenyl, 3-methylphenyl, 2-fluorophenyl, 2,6-difluorophenyl, 2-fluoro-6-methoxyphenyl, 2-fluoro-6-ethoxyphenyl, 2,3,5,6-tetrafluorophenyl, 2-chlorophenyl, 3-chlorophenyl, 1-cyclohexenyl, 2-naphthyl, 2,5-dimethoxyphenyl, 2-azidophenyl, 2,3,4-trifluorophenyl, 2-fluoro-6chlorophenyl, 2,6-dimethoxyphenyl, 2,3,6-trichlorophenyl, 2,6-dichlorophenyl, 2,3,5-trichlorophenyl, 3,5dichlorophenyl, 3-fluorophenyl, 2,4-dimethoxyphenyl, 2-pyridyl, 2-(6-methoxy)pyridyl, 2-(6-ethoxy)pyridyl, 2-(6-fluoro)pyridyl, 2-(5-fluoro) pyridyl, 2-(4-fluoro)pyridyl, 2-(3-fluoro)pyridyl, 2-(6-chloro)pyridyl, 2-(5-chloro)pyridyl, 2-(4-chloro) pyridyl, 2-(3-chloro)pyridyl, 2-(5-methoxy-6-fluoro) pyridyl, 2-(3-methoxy-4-fluoro)pyridyl, 2-(6-methoxy-3-fluoro)pyridyl, 2-(5-methoxy-6-fluoro)pyridyl, 2-(3-methoxy6-fluoro)pyridyl, 2-(6-ethoxy-3-fluoro) pyridyl, 2-(5,6-difluoro)pyridyl, 2-(3,6difluoro)pyridyl, 2-(5,6-dichloro)pyridyl, 2-(3,6-dichloro)pyridyl, 2-(6-methoxy)pyridyl, 2-(6-ethoxy)pyridyl, 2-(1,3-pyrimidyl), 2-pyrazinyl, 3-pyridazinyl, 2,6-difluoro-3-methoxyphenyl, 2,6-difluoro-3-ethoxyphenyl, 2,6-difluoro-4-methoxyphenyl, 2,6difluoro-4-ethoxyphenyl, 2-(3-ethoxy)pyridyl, 2-(3-methoxy) pyridyl, 2,6-difluorophenyl, 2,6-difluoro-3-N-methylcarboxamidephenyl, 2-fluoro-6-chlorophenyl, 3-bromo-6-methoxyphenyl, 3-ethoxyphenyl, 3-bromo-6thoxyphenyl, 3-(2-fluoro)pyridyl, (2-vinyl)phenyl, (3-vinyl)phenyl, (3-methoxycarbonyl)phenyl, 5,6-dimethylbenzotriazolyl, 2,3fluoro-6-methoxyphenyl, 2,6-difluoro-3-cyanophenyl, 3-ethynylphenyl, or 2,5diethoxyphenyl.

7. The method as recited in claim 6 wherein said agent is selected from ddI, ddC, or AZT.

8. A compound having the formula

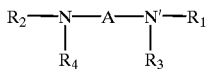

(1A)

wherein A is

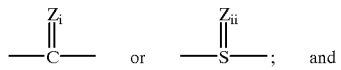

$Z_i$ is O, Se, $NR^a$ or $C(R^a)_2$, and
$Z_{ii}$ is —O or (=O)$_2$;
and wherein $R^a$ is H, $OR^b$, CN, $NO_2$, $N(R^b)_2$, $SR^b$, $SO_2R^b$, $SO_2N(R^b)_2$, $COR^b$, $CO_2R^b$, $CON(R^b)_2$, $PO(R^b)_2$, $PO(OR^b)_2$, $PO(NR^b)_2$, wherein $R^b$ is hydrogen, $C_1$–$C_6$ alkyl, $C_1$–$C_6$ substituted alkyl, $C_2$–$C_6$ alkenyl, $C_2$–$C_6$ substituted alkenyl, $C_2$–$C_6$ alkynyl, $C_2$–$C_6$ substituted alkynyl, $C_1$–$C_6$ alkoxy, $C_1$–$C_6$ substituted alkoxy, $C_{4-10}$ aralkyl, $C_{1-10}$ alkaryl, $C_{1-10}$ alkylthio, $C_{4-10}$ aralkylthio, $C_{1-10}$ alkylsulfinyl, $C_{4-10}$ alkylsulfonyl, $C_{1-10}$ alkylsulfonyl, $C_{4-10}$ aralkylsulfonyl, carboxy, $C_{1-10}$ alkylthiocarbonyl, $C_{4-10}$ aralkylcarbonyl, $C_{4-10}$ aralkylthiocarbonyl, $C_{4-10}$ aralkoxycarbonyl, $C_{4-10}$ aralkoxycarbonyl, $C_{1-4}$ alkyl, $C_{4-10}$ aralkoxy, $C_{1-12}$ dialkylamino-$C_{1-6}$ aralkanoylamino $C_{4-10}$ aralkylamino or $C_1$–$C_4$ alkanoyloxy; and wherein $R_1$ is pyrazinyl, substituted pyrazinyl, pyridazinyl, substituted pyndazinyl, pyrimidyl, substituted pyrimidyl, and wherein the substituted $R_1$ groups have 1 to 8 substituents independently selected from halo, $C_1$–$C_6$ alkyl, $C_1$–$C_5$ alkoxy, $C_2$–$C_6$ alkenyl, $C_2$–$C_8$ alkynyl, $C_2$–$C_8$ alkenoxy, amino, nitro, cyano, carboxy, hydroxymethyl, aminomethyl, carboxymethyl, $C_1$–$C_4$ alkylthio, hydroxy, $C_1$–$C_4$ alkanoyloxy, carbamoyl, halo-substituted $C_1$–$C_6$ alkyl, $C_1$–$C_6$ alkoxy-substituted $C_1$–$C_6$ alkyl, a group of the formula

wherein $R_x$ is $C_1$–$C_6$ alkyl or amino; or a group of the formula

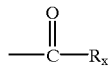

wherein $R_x$ is as defined above;
$R_2$ is a group of the formula

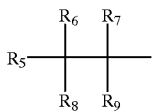

wherein $R_5$ is a stable, unsaturated, substituted or unsubstituted i) 3 to 8 membered monocyclic ring having 0 to 4 hetero atoms or ii) a 7 to 10 membered bicyclic ring having 0 to 5 hetero atoms, said hetero atoms being selected from S, O and N; and two of $R_6$, $R_7$, $R_8$ and $R_9$ are independently $C_3$–$C_8$ cycloalkyl, hydrogen, $C_1$–$C_6$ alkyl, $C_2$–$C_6$ alkenyl, $C_2$–$C_6$ alkynyl, substituted $C_1$–$C_6$ alkyl, substituted $C_2$–$C_6$ alkenyl, or substituted $C_2$–$C_6$ alkynyl, $C_1$–$C_6$ substituted alkoxy, halo, amino, nitro, cyano, $C_1$–$C_5$ alkoxy, hydroxy, hydroxymethyl, aminomethyl, carboxymethyl, $C_1$–$C_4$ alkylthio, $C_1$–$C_4$ alkanoyloxy, carbamoyl, or a halo substituted $C_1$–$C_6$ alkyl; and the other two of which, along with the carbons to which they are attached, combine to form a stable, saturated or unsaturated, substituted or unsubstituted, 3 to 7 membered organic monocylic ring having 0 to 4 hetero atoms selected from S, O, or N; R3 and R4 are independently hydrogen, hydroxy, $C_1$–$C_6$ alkyl, $C_2C_6$ alkenyl, $C_2$–$C_6$ alkynyl, substituted $C_1$–$C_6$ alkyl, substituted $C_2$–$C_6$ alkenyl, or substituted $C_2$–$C_6$ alkynyl, substituted alkoxy, amino, cyano, nitro, $C_1$–$C_6$ alkoxy, $C_1$–$C_8$ sustituted alkoxy, carboxy, hydroxymethyl, aminomethyl, carboxymethyl, $C_1$–$C_4$ alkylthio, $C_1$–$C_4$ alkanoyloxy, halo-substituted ($C_1$–$C_6$) alkyl, or carbamoyl; or a pharmaceutically acceptable salt thereof.

9. The compound of claim 8, wherein $R_1$ is (6-chloro) pyrazinyl, (6-bromo) pyrazinyl, 3-(6-bromo) pyridazinyl, (5yano)pyrazinyl, (6-cyano)pyrazinyl, 3-(6cyano) pyridazinyl, (5-chloro) pyrzinyl, (5-bromo) pyrazinyl, (6-chloro) pyridazinyl, 2-(3-[6-bromo]pyridazinyl), 2-(3-[6-chloro]pyridazinyl), 2-(3-[6-cyano]pyridazinyl), 3-(6-methoxy) pyridazinyl, 4-(6-aminopyrimidinyl), 4pyrimidinyl, 2-(3-pyridazinyl), 2-(3-(6-methyl) pyridazinyl, 2-pyrazinyl, or 2-(5-methyl) pyrazinyl.

10. The compound of claim 8, wherein $R_3$ and $R_4$ are hydrogen.

11. The compound of claim 8, wherein $R_2$ is $R_5$—(cis)-cyclopropyl.

12. The compound of claim 8, wherein R5 is cyclo $(C_3$–$C_8)$alkenyl, thiazolyl, substituted thiazolyl, tetrazolyl, substituted tetrazolyl, triazolyl, substituted triazolyl, pyridyl, substituted pyridyl, imidazolyl, substituted imidazolyl, phenyl, substituted phenyl, naphthyl, substituted naphthyl, benzoxazolyl, substituted benzoxazolyl, benzimidazolyl, substituted benzimidazolyl, thiazolyl, substituted thiazolyl, oxazolyl, substituted oxazolyl, benzothiazolyl, substituted benzothiazolyl, pyrazinyl, substituted pyrazinyl, pyridazinyl, substituted pyridazinyl, thadaizolyl, substituted thadiazolyl, benzotriazolyl, substituted benzotriazolyl, pyrrolyl, substituted pyrrolyl, indolyl, substituted indolyl, benzothienyl, substituted benzothienyl, thienyl, substituted theinyl, benzofuryl, substituted benzofuryl, furyl, substituted furyl, quinolinyl, substituted quinolinyl, isoquinolinyl, substituted isoquinolinyl, pyrazolyl, or substituted pyrazolyl.

13. The compound of claim 12, wherein $R_5$ is phenyl, 2-methoxyphenyl, 3-methoxyphenyl, 4-methoxyphenyl, 2-ethoxyphenyl, 2-methylphenyl, 3-methylphenyl, 2-fluorophenyl, 2,6-difluorophenyl, 2-fluoro-6-methoxyphenyl, 2-fluoro-6-ethoxyphenyl, 2,3,5,6-tetrafluorophenyl, 2-chlorophenyl, 3-chlorophenyl, 1-cyclohexenyl, 2-naphthyl, 2,5-dimethoxyphenyl, 2-azidophenyl, 2,3,4-trifluorophenyl, 2-fluoro-67-chlorophenyl, 2,6-dimethoxyphenyl, 2,3,6-trichlorophenyl, 2,6-dichlorophenyl, 2,3,5-trichlorophenyl, 3,5-dichlorophenyl, 3-fluorophenyl, 2,4-dimethoxyphenyl, 2-pyridyl, 2-(6-methoxy)pyridyl, 2-(6-ethoxy)pyridyl, 2-(6-fluoro)pyridyl, 2-(5-fluoro)pyridyl 2-(4-fluoro)pyridyl, 2-(3-fluoro)pyridyl, 2-(6-chloro)pyridyl, 2-(5-chloro)pyridyl, 2-(2-(4-chloro)pyridyl, 2-(3-chloro)pyridyl, 2-(5-methoxy-6-fluoro)pyridyl, 2-(3-methoxy-6-fluoro)pyridyl, 2-(6-methoxy-3-fluoro)pyridyl, 2-(5-ethoxy-6-fluoro)pyridyl, 2-(3-ethoxyl-6-fluoro)pyridyl, 2-(6-ethoxy-3-fluoro)pyridyl, 2-(5,6-difluoro)pyridyl, 2-(3,6-difluoro)pyridyl, 2-(5,6-dichloro)pyridyl, 2-(3,6-dichloro)pyridyl, 2-(6-methoxy)

pyridyl, 2-(6-ethoxy)pyridyl, 2-(1,3-pyrimidyl), 2-pyrizinyl, 3-pyridazinyl, 2,6-difluoro-3-methoxyphenyl, 2,6-difluoro-3-ethoxylphenyl, 2,6-difluoro-4-methoxyphenyl, 2,6-difluoro-4-ethoxyphenyl, 2-(3-ethoxy)pyridyl, 2-(3-methoxy)pyridyl, 2,6-difluorophenyl, 2,6-difluoro-4-ethoxyphenyl, 2-(3-ethoxy)pyridyl, 2-(3-methoxy)pyridyl, 2,6-difluorophenyl, 2,6-difluoro-3-N-methylcarboxamidephenyl, 2-fluoro-6-chlorphenyl, 3-bromo-6-methoxyphenyl, 3-ethoxyphenyl, 3-bromo-6-ethoxyphenyl, 3-(2-fluoro)pyridyl, (2-vinyl)phenyl, (3-vinyl)phenyl, (3-methoxycarbonyl)phenyl, 5,6-dimethylbenzotriazolyl, 2,3-difluoro-6-methoxyphenyl, 2,6-difluoro-3-cyanophenyl, 3-ethynylphenyl, or 2,5-diethoxyphenyl.

14. A pharmaceutical formulation comprising an effective amount of a compound as defined in claim 8; and a pharmaceutically acceptable carrier diluent therefor.

15. The composition according to claim 14, further comprising at least one other therapeutic agent.

16. A pharmaceutical formulation according to claim 15, wherein said agent is selected from ddI, ddC or AZT.

17. The compound of claim 1, wherein the N' linkage to $R_1$ is at the 2 position relative to a heteroatom in said pyrazinyl, substituted pyrazinyl, pyridazinyl, substituted pyridazinyl, pyrimidine or substituted pyrimidine.

18. A method for treating or inhibiting HIV, comprising administering to a patient suffering from HIV infection an amount of a compound of claim 17 effective for treating or inhibiting HIV.

19. The compound of claim 8, wherein $Z_i$ is O.

20. A compound having the formula

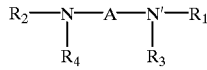

(1A)

wherein A is

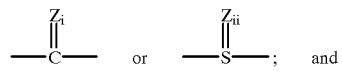

and $Z_i$ is O, Se, $NR^a$ or $C(R^a)_2$, and
$Z_{ii}$ is —O or (═O)$_2$;
and $R^a$ is H, $OR^b$, CN, $NO_2$, $N(R^b)_2$, $SR^b$, $SO_2R^b$, $SO_2N(R^b)_2$, $COR^b$, $CO_2R^b$, $CON(R^b)_2$, $PO(R^b)_2$, $PO(OR^b)_2$, $PO(NR^b)_2$, wherein $R^b$ is hydrogen, $C_1$–$C_6$ alkyl, $C_1$–$C_6$ substituted alkyl, $C_2$–$C_6$ alkenyl, $C_2$–$C_6$ substituted alkenyl, $C_2$–$C_8$ alkynyl, $C_2$–$C_8$ substituted alkynyl $C_1$–$C_6$ alkoxy, $C_1$–$C_6$ substituted alkoxy, $C_{4-10}$ aralkyl, $C_{1-10}$ alkaryl, $C_{1-10}$ alkaryl, $C_{1-10}$ alkylthio, $C_{4-10}$ aralkylthio, $C_{1-10}$ alkylsulfinyl, $C_{4-10}$ alkylsulfinyl, $C_{1-10}$ alkylsulfonyl, $C_{4-10}$ aralkylsulfonyl, carboxy, $C_{1-10}$ alkylthiocarbonyl, $C_{4-10}$ aralkoxycarbonyl, $C_{4-10}$ aralkoxycarbonyl, $C_{1-4}$ alkyl, $C_{4-10}$ aralkoxy, $C_{1-12}$ dialkylamino-$C_{1-6}$ aralkyanoylamino $C_{4-10}$ aralkylamino or $C_{1-4}$ alkanoyloxy; $R_3$ and $R_4$ are independently hydrogen, hydroxy, $C_1$–$C_6$ alkyl, $C_2$–$C_6$ alkenyl, $C_2$–$C_8$ alkynyl, substituted $C_1$–$C_6$ alkyl, substituted $C_2$–$C_6$ alkenyl, or substituted $C_2$–$C_6$ alkynyl, substituted alkoxy, amino, cyano, nitro, $C_1$–$C_6$ alkoxy, $C_1$–$C_6$ substituted alkoxy, carboxy, hydroxymethyl, aminomethyl, carboxymethyl, $C_1$–$C_4$ alkylthio, $C_1$–$C_4$ alkanoyloxy, halo-substituted ($C_1$–$C_6$)alkyl, or carbamoyl; $R_1$ is a substituted or unsubstituted 6 membered organic monocyclic ring having 2–4 N atoms wherein the substituted $R_1$ groups have substituents independently selected from halo, $C_1$–$C_6$ alkyl, $C_1$–$C_5$ alkoxy, $C_2$–$C_6$ alkenyl, $C_2$–$C_8$ alkynyl, $C_2$–$C_8$ alkenoxy, amino, nitro, cyano, carboxy, hydroxymethyl, aminomethyl, carboxymethyl, $C_1$–$C_4$ alkylthio, hydroxy, $C_1$–$C_4$ alkanoyloxy, carbamoyl, halo-substituted $C_1$–$C_6$ alkyl, $C_1$–$C_6$ alkoxy-substituted $C_1$–$C_6$ alkyl, a group of the formula

wherein $R_x$ is $C_1$–$C_6$ alkyl or amino; or a group of the formula

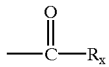

wherein $R_x$ is as defined above;
$R_2$ is a group of the formula

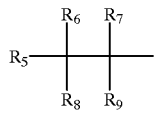

wherein $R_5$ is a stable, unsaturated, substituted or unsubstituted 3 to 8 membered monocyclic ring having 0 to 4 hetero atoms or ii) a 7 to 10 membered bicyclic ring having 1 to 5 hetero atoms, said hetero atoms being selected from S, O and N; $R_3$ and $R_4$ are independently hydrogen, hydroxy, $C_1$–$C_6$ alkyl, $C_2$–$C_6$ alkenyl, $C_2$–$C_6$ alkynyl, substituted $C_1$–$C_6$ alkyl, substituted $C_2$–$C_6$ alkenyl, or substituted $C_2$–$C_6$ alkynyl, substituted alkoxy, amino, cyano, nitro, $C_1$–$C_6$ alkoxy, $C_1$–$C_6$ substituted alkoxy, carboxy, hydroxymethyl, aminomethyl, carboxymethyl, $C_1$–$C_4$ alkylthio, $C_1$–$C_4$ alkanoyloxy, halo-substituted ($C_1$–$C_6$)alkyl, or carbamoyl; and $R_6$, $R_7$, $R_8$ and $R_9$ are independently $C_3$–$C_8$ cycloalkyl, hydrogen, $C_1$–$C_6$ alkyl, $C_2$–$C_6$ alkenyl, $C_2$–$C_6$ alkynyl, substituted $C_1$–$C_6$ alkyl, substituted $C_2$–$C_6$ alkenyl, or substituted $C_2$–$C_6$ alkyny $C_1$–$C_6$ substituted alkoxy, halo, amino, nitro, cyano, $C_1$–$C_5$ alkoxy, hydroxy, hydroxymethyl, aminomethyl, carboxymethyl, $C_1$–$C_4$ alkylthio, $C_1$–$C_4$ alkanoyloxy, carbamoyl, or a halo substituted $C_1$–$C_6$ alkyl; or a pharmaceutically acceptable salt thereof; with the provisos that:

a) if $R_3$, $R_4$ and $R_6$–$R_9$ are all hydrogen, then the following combinations are excluded:

| $Z_i$ | $R_1$ | $R_5$ |
|---|---|---|
| NH | pyrimidin-2yl | phenyl |
| NH | imidazol-2-yl | phenyl or substituted phenyl. |

21. The compound according to claim 20, wherein $R_1$ is pyrazinyl, substituted pyrazinyl, pyrimidinyl, substituted pyrimidinyl, pyridazinyl, or substituted pyridazinyl.

22. The compound according to claim 20, wherein $R_1$ is (6-chloro) pyrazinyl, (6-bromo) pyrazinyl, 3-(6-bromo) pyridazinyl, (5-cyano)pyrazinyl, (6-cyano)pyrazinyl, 3-(6-cyano)pyridazinyl, (5-chloro) pyrazinyl, (5-bromo) pyrazinyl, (6-chloro) pyridazinyl, 2-(3-[6-bromo] pyridazinyl), 2-(3-[6-chloro]pyridazinyl), 2-(3-[6-cyano] pyridazinyl), 3-(6-methoxy) pyridazinyl, 4-(6- aminopyrimidinyl), 4-pyrimidinyl, 2-(3-pyridazinyl), 2-(3-(6-methyl) pyridazinyl, 2-pyrazinyl, 2-(5-methyl) pyrazinyl.

23. The compound of claim 20, wherein $R_3$ and $R_4$ are hydrogen.

24. The compound of claim 20, wherein $Z_i$ is O.

25. The compound of claim 20, wherein the N' linkage to R1 is at the 2 position relative to a said N atom of said organic monocyclic ring.

26. A method for treatment of HIV infection, comprising administration of a compound of claim 20 effective for treating HIV infection.

27. The compound of claim 20, wherein $R_5$ is cyclo ($C_3$–$C_8$)alkenyl, thiazolyl, substituted thiazolyl, tetrazolyl, substituted tetrazolyl, triazolyl, substituted thiazolyl, pyridyl, substituted pyridyl, imidazolyl, substituted imidazolyl, phenyl, substituted phenyl, thiazolyl, substituted thiazolyl, oxazolyl, substituted oxazolyl, pyrazinyl, substituted pyrazinyl, pyridazinyl, substituted pyridazinyl, thiadiazolyl, substituted thiadiazolyl, pyrrolyl, substituted pyrrolyl, thienyl, substituted thienyl, furyl, substituted furyl, pyrazolyl, and substituted pyrazolyl.

28. The compound of claim 27, wherein $R_5$ is phenyl, 2-methoxyphenyl, 3-methoxyphenyl, 4-methoxyphenyl, 2-ethoxyphenyl, 2-methylphenyl, 3-methylphenyl, 2-fluorophenyl, 2,6-difluorophenyl, 2-fluoro-6-methoxyphenyl, 2-fluoro-6-ethoxyphenyl, 2,3,5,6-tetrafluorophenyl, 2-chlorophenyl, 3-chlorophenyl, 1-cyclohexenyl, 2,5-dimethoxyphenyl, 2-azidophenyl, 2,3,4-trifluorophenyl, 2-fluoro-6-chlorophenyl, 2,6-dimethoxyphenyl, 2,3,6-trichlorophenyl, 2,6-dichlorophenyl, 2,3,5-trichlorophenyl, 3,5-dichlorophenyl, 3-fluorophenyl, 2,4-dimethoxyphenyl, 2-pyridyl, 2-(6-methoxy)pyridyl, 2-(6-ethoxy)pyridyl, 2-(6-fluoro)pyridyl, 2-(5-fluoro)pyridyl, 2-(4-fluoro)pyridyl, 2-(3-fluoro)pyridyl, 2-(6-chloro)pyridyl, 2-(5-chloro)pyridyl, 2-(4-chloro)pyridyl, 2-(3-chloro)pyridyl, 2-(5-methoxy-6-fluoro)pyridyl, 2-(3-methoxy-6-fluoro)pyridyl, 2-(6-methoxy-3-fluoro)pyridyl, 2-(5-ethoxy-6-fluoro)pyridyl, 2-(3-ethoxy-6-fluoro)pyridyl, 2-(6-ethoxy-3-fluoro)pyridyl, 2-(5,6-difluoro)pyridyl, 2-(3,6-difluoro)pyridyl, 2-(5,6-dichloro)pyridyl, 2-(3,6-dichloro)pyridyl, 2-(6-methoxy)pyridyl, 2-(6-ethoxy)pyridyl, 2-(1,3-pyrimidyl), 2-pyrazinyl, 3-pyridazinyl, 2,6-difluoro-3-methoxyphenyl, 2,6-difluoro-3-ethoxyphenyl, 2,6-difluoro-4-methoxyphenyl, 2,6-difluoro-4-ethoxyphenyl, 2-(3-ethoxy)pyridyl, 2-(3-methoxy)pyridyl, 2,6-difluorophenyl, 2,6-difluoro-3-N-methylcarboxamidephenyl, 2-fluoro-6-chlorophenyl, 3-bromo-6-methoxyphenyl, 3-ethoxyphenyl, 3-bromo-6-ethoxyphenyl, 3-(2-fluoro)pyridyl, (2-vinyl)phenyl, (3-vinyl)phenyl, (3-methoxycarbonyl)phenyl, 2,3-difluoro-6-methoxyphenyl, 2,6-difluoro-3-cyanophenyl, 3-ethynylphenyl, and 2,5-diethoxyphenyl.

29. A pharmaceutical composition comprising an effective anti-HIV amount of a compound of claim 20; and a pharmaceutically acceptable carrier or diluent.

30. The composition according to claim 29, further comprising at least one other therapeutic agent.

31. A pharmaceutical composition according to claim 30, wherein said at least one other therapeutic agent is ddI, ddC or AZT.

* * * * *